US005892112A

United States Patent [19]
Levy et al.

[11] Patent Number: 5,892,112
[45] Date of Patent: Apr. 6, 1999

[54] PROCESS FOR PREPARING SYNTHETIC MATRIX METALLOPROTEASE INHIBITORS

[75] Inventors: Daniel E. Levy, Alameda, Calif.;
Damian Grobelny, Watsonia North, Australia; Cho Tang, Moraga, Calif.;
Kevin R. Holme, Alameda, Calif.;
Richard E. Galardy, Guilford, Conn.;
Gregory S. Schultz, Gainesville, Fla.;
Asaad Nematalia, Alameda; John H. Musser, San Carlos, both of Calif.

[73] Assignees: Glycomed Incorporated, Alameda, Calif.; The University of Florida, Gainesville, Fla.

[21] Appl. No.: 184,727

[22] Filed: Jan. 21, 1994

Related U.S. Application Data

[63] Continuation-in-part of Ser. No. 44,324, Apr. 7, 1993, and a continuation of Ser. No. 881,630, May 12, 1992, Pat. No. 5,270,326, which is a continuation of Ser. No. 616,021, Nov. 20, 1990, Pat. No. 5,114,953, said Ser. No. 44,324, is a continuation-in-part of Ser. No. 817,039, Jan. 7, 1992, Pat. No. 5,268,384, which is a continuation of Ser. No. 747,751, Aug. 20, 1991, Pat. No. 5,239,078, and Ser. No. 747,752, Aug. 20, 1991, Pat. No. 5,189,178, which is a continuation-in-part of Ser. No. 615,798, Nov. 21, 1990, Pat. No. 5,183,900, said Ser. No. 747,751, is a continuation-in-part of Ser. No. 615,798.

[51] Int. Cl.[6] .......................... C07B 57/00; C07C 227/18; C07C 235/16; C07D 209/20
[52] U.S. Cl. .......................... 564/133; 564/134; 564/138; 564/144; 562/401; 562/402; 562/433; 562/512; 562/553; 562/554; 562/561; 562/565; 562/621; 562/623; 548/497; 548/498
[58] Field of Search .................... 548/497, 498; 562/433, 401, 402, 512, 561, 553, 554, 565, 621, 623; 564/123, 138, 144

[56] References Cited

U.S. PATENT DOCUMENTS 4,558,034  12/1985  Galardy et al. ................. 514/7
4,599,361  7/1986  Dickens et al. ................. 514/575
4,743,587  5/1988  Dickens et al. ................. 514/575

(List continued on next page.)

FOREIGN PATENT DOCUMENTS

| 0 236 872 B1 | 2/1987 | European Pat. Off. . |
| 0 236 872 | 9/1987 | European Pat. Off. . |
| 0 445 206 B1 | 11/1989 | European Pat. Off. . |
| 446 257 A | 9/1991 | European Pat. Off. ...... C07C 327/32 |
| 0 574 758 A1 | 12/1993 | European Pat. Off. ...... C07D 209/48 |
| 0 575 844 A2 | 12/1993 | European Pat. Off. ...... C07C 259/06 |

(List continued on next page.)

OTHER PUBLICATIONS

Ogita et al. (1992) *J. Antibiot*, 45(11), 1723–1732.
Tanzawa et al, (1992) *J. Antibiot*., 45(11), 1733–1737.
Lundt, et al., Int.J. Peptide Protein Res. (1978) 12:258–268.
Masui et al., Bull. Chem. Soc. Jpn. 53:464–468 (1980).
Kortylewicz et al., J. Med. Chem. (1990) 33:(1):263–273.
Dean, J.Chem. Soc. (1965) 6655–6659.
Mata, et al., Tetrahedron Letters, 29:(52):6893–6896 (1988).
Bodanszky, et al., J. Peptide Protein Res. (1984) 23:565–572.
McMurry et al., Synthetic Communications 2(6), 389–394 (1972).
Landini et al., J. Org. Chem. (1982) 47:154–155.
Tozuka et al., J. of Antibiotics (Mar. 1983) 36(3):276–282.
Wang et al., Am. J. Physiol. (1990) 259:R645–R650.

(List continued on next page.)

*Primary Examiner*—Johann Richter
*Assistant Examiner*—Jane C. Oswecki
*Attorney, Agent, or Firm*—Lyon & Lyon LLP

[57] ABSTRACT

Synthetic mammalian matrix metalloprotease inhibitors are disclosed that are useful for treating or preventing diseases wherein said diseases are caused by unwanted mammalian matrix metalloprotease activity and include skin disorders, keratoconus, restenosis, rheumatoid arthritis, wounds, cancer, angiogenesis and shock.

14 Claims, 14 Drawing Sheets

U.S. PATENT DOCUMENTS

| | | | |
|---|---|---|---|
| 4,996,358 | 2/1991 | Handa et al. | 562/621 |
| 5,114,953 | 5/1992 | Galardy et al. | 514/323 |
| 5,183,900 | 2/1993 | Galardy et al. | 548/495 |
| 5,189,178 | 2/1993 | Galardy et al. | 548/495 |
| 5,239,078 | 8/1993 | Galardy et al. | 546/201 |
| 5,240,958 | 8/1993 | Campion et al. | 514/445 |
| 5,268,384 | 12/1993 | Galardy | 514/419 |
| 5,270,326 | 12/1993 | Galardy et al. | 514/323 |

FOREIGN PATENT DOCUMENTS

| | | | |
|---|---|---|---|
| WO 90/05716 | 5/1990 | WIPO . | |
| WO 90/05719 | 5/1990 | WIPO | C07C 323/62 |
| WO 90/02716 | 3/1991 | WIPO . | |
| 9117982 | 11/1991 | WIPO . | |
| WO 93/20047 | 10/1993 | WIPO | C07C 317/44 |
| WO 93/21942 | 11/1993 | WIPO | A61K 37/02 |
| WO 93/23075 | 11/1993 | WIPO | A61K 37/64 |

OTHER PUBLICATIONS

Chaudry et al., Am. Jour. Surg. (1993) 165:2A(Suppl) 595–675.
Lindner et al, J. Clin.Invest. (1992) 90:2044–2049.
Wang et al. J.Surg.Res. (1991) 50:163–169.
Wang et al. J.Surg.Res. (1990) 48:464–470.
Gijbels, et al., Journal of Neuroimmunology (1992) 41:29–34.
Teba, et al., Circulatory Shock (1992) 91:121–129.
Galardy, Drugs of the Future (1993) 18(12):1109–1111.
Bird et al. (1994) J.Med.Chem. 37:158–169.
Chapman et al. (1993) J.Med.Chem. 36:4293–4301.
Beszant et al. (1993) J.Med.Chem. 36:4030–4039.
Naito et al. (1993) Agents Actions 39:182–186.
G. S. Schultz et al., "Treatment of Alkali–Injured Corneas With a Synthetic Inhibitor of Matrix Metalloprotease" *Investigation Ophthalmology & Visual Science*, vol. 33, No. 12, pp. 3325–3331, Nov. 1992.

PROCESS FOR PREPARING SYNTHETIC MATRIX METALLOPROTEASE INHIBITORS

This is a continuation-in-part of application Ser. No. 08/044,324, filed Apr. 7, 1993, which is a continuation-in-part of application Ser. No. 07/817,039, filed Jan. 7, 1992, now U.S. Pat. No. 5,268,384, which is a continuation-in-part of application Ser. No. 07/747,751, filed Aug. 20, 1991, now U.S. Pat. No. 5,239,078, and Ser. No. 07/747,752 filed Aug. 20, 1991, now U.S. Pat. No. 5,189,178, both of which are continuations-in-part of application Ser. No. 07/615,798, filed Nov. 21, 1990, now U.S. Pat. No. 5,183,900; and a continuation of application Ser. No. 07/881,630, filed May 12, 1992, now U.S. Pat. No. 5,270,326, which is a continuation of application Ser. No. 07/616,021, filed Nov. 20, 1990, now U.S. Pat. No. 5,114,953.

This invention was made with government support under grant DAMD17-91-C-1-95 awarded by the U.S. Department of the Army. The government has certain rights in the invention.

TECHNICAL FIELD

The invention relates to synthetic compounds that are inhibitors of matrix metalloproteases, and certain medical applications thereof.

RELEVANT ART

There are a number of enzymes which effect the breakdown of structural proteins and which are structurally related metalloproteases. These include human skin fibroblast collagenase, human skin fibroblast gelatinase, human neutrophil collagenase and gelatinase, and human stromelysin. These are zinc-containing metalloprotease enzymes, as are the angiotensin-converting enzymes and the enkephalinases.

Collagenase and related enzymes are important in mediating the symptomology of a number of diseases, including rheumatoid arthritis (Mullins, D. E., et al., *Biochim Biophys Acta* (1983) 695:117–214); the metastasis of tumor cells (ibid., Broadhurst, M. J., et al., EP application 276436 (1987), Reich, R., et al., *Cancer Res* (1988) 48:3307–3312); and various ulcerated conditions. Ulcerative conditions can result in the cornea as the result of alkali burns or as a result of infection by *Pseudomonas aeruginosa*, Acanthamoeba, Herpes simplex and vaccinia viruses. Other conditions characterized by unwanted matrix metalloprotease activity include periodontal disease, epidermolysis bullosa and scleritis.

In view of the involvement of collagenase in a number of disease conditions, attempts have been made to prepare inhibitors to this enzyme. A number of such inhibitors are disclosed in EP applications 126,974 (published 1984) and 159,396 (published 1985) assigned to G. D. Searle. These inhibitors are secondary amines which contain oxo substituents at the 2-position in both substituents bonded to the amino nitrogen.

More closely related to the compounds of the present invention are those disclosed in U.S. Pat. Nos. 4,599,361 and 4,743,587, also assigned to G. D. Searle. These compounds are hydroxylamine dipeptide derivatives which contain, as a part of the compound, a tyrosine or derivatized tyrosine residue or certain analogs thereof.

Other compounds that contain sulfhydryl moieties as well as residues of aromatic amino acids such as phenylalanine and tryptophan are disclosed in PCT application WO 88/06890. Some of these compounds also contain i-butyl side chains.

EP application 498,665, inventors Beckett, R. P. et al describes the process for preparation of hydroxamic acid derivatives and uses thereof.

PCT application WO 92/21360, inventors Sahoo, S. et al, describes substituted N-carboxyalkylpeptidyl derivatives and applications of these compounds for treating certain diseases including osteoarthritis, rheumatoid arthritis, certain cancers and corneal ulceration.

EP application 497,192, inventors Lobb, R. et al, presents peptide collagenase inhibitors with pharmacological properties.

U.S. Pat. No. 4,681,894, inventors Murray, W. et al, presents hydroxamic acids and esters that are useful anti-inflammatory agents.

U.S. Pat. No. 4,943,587, inventors Cetenko et al., describe hydroxamate derivatives of selected nonsteroidal anti-inflammatory acyl residues. Medical applications of the compounds are also shown.

U.S. Pat. No. 4,918,105, inventors Cartwright, T. et al., presents compounds with collagenase-inhibiting activity. Certain medical applications are described including arthritis, ulceration, and tumor invasion.

EP application 574,758, inventors Broadhurst, M. J. et al, presents hydroxamic acids derivatives as collagenase inhibitors for treatment and prevention of degenerative joint disease, invasive tumors, atherosclerosis and multiple sclerosis.

PCT application WO 93/23075, inventors Liang, C. et al, describes the use of matrix metalloproteinase inhibitors for the treatment of vascular leakage syndrome and collagenase induced disease.

Inhibitors have also been disclosed for the related protease, thermolysin. These include hydroxamic peptide derivatives described by Nishino, N., et al., *Biochemistry* (1979) 18:4340–4347; Nishino, N., et al., *Biochemistry* (1978) 17:2846–2850. Tryptophan is also known to be therapeutic in various conditions, some of which may involve collagenase (see, for example, JP 57/058626; U.S. Pat. Nos. 4,698,342; 4,291,048). Also, inhibitors of bacterial collagenases have been disclosed in U.S. Pat. No. 4,558,034.

It has now been found that the compounds described below have superior inhibiting activity with respect to matrix metalloproteases. The invention compounds add to the repertoire of agents available for the treatment of conditions and diseases which are characterized by unwanted activity by the class of proteins which destroy structural proteins and designated "matrix metalloprotease" herein.

Compounds of the invention are also useful for treating diseases that have as one component unwanted angiogenesis. Angiogenesis is defined as the growth of new blood vessels, in particular, capillaries. The ingrowth of such capillaries and ancillary blood vessels is essential for tumor growth and is thus an unwanted physiological response which encourages the spread of malignant tissue and metastases. Inhibition of angiogenesis is therefore envisioned as a component of effective treatment of malignancy. Neovascularization of the eye is a major cause of blindness. One form of this condition, proliferative diabetic retinopathy, results from diabetes; blindness can also be caused by neovascular glaucoma. Inhibition of angiogenesis is useful in treating these conditions also.

PCT application WO 91/11193, published 25 Jan. 1991 describes the isolation of a collagenase inhibitor from cartilage which inhibits the formation of blood vessels. This composition, designated cartilage-derived inhibitor (CDI), is reported to inhibit tumor-induced angiogenesis in the rabbit corneal pocket assay and to inhibit capillary tube formation. It is further speculated that other collagenase inhibitors such as peptides or antibodies immunoreactive with collagenase will also have the ability to inhibit blood vessel formation.

In addition, EP application 424,193 published 24 Apr. 1991, describes the activity of actinonin as an angiogenesis inhibitor. Actinonin is an antibiotic produced by a particular strain of Streptomyces and is a modified peptide structure.

As disclosed in the two foregoing applications, unwanted levels of angiogenesis are present not only in association with tumor growth, but also are the cause of blindness resulting from diabetic retinopathy and other ocular pathologies.

Compounds of the invention are also useful for treating a certain form of shock, hypovolemic shock and related syndromes. In general, hypovolemic shock can be described as widespread hypoperfusion of cells and tissue due to reduction in blood volume or cardiac output or redistribution of blood resulting in an inadequate effective circulating volume.

Hypovolemic shock, and models for studying this condition are described by Chaudry and Ayala in "Immunological Aspects of Hemorrhage" (R. G. Landes Co., Austin, Tex., 1992). Generally, hypovolemic shock due to reduced blood flow associated with blood loss results in "sludging" of the blood and capillary "plugging" by erythrocytes, platelets and neutrophils. This in turn leads to the insufficient delivery of oxygen and nutrients to cells and tissues, deficient clearance of other metabolites, and to activation of neutrophils and platelets. This oxidant stress (Hypoxia) and release of other factors from the endothelium and macrophages stimulates the arachidonic acid cascade and the production of chemoattractant and inflammation mediators, leading to further neutrophil infiltration. The activation of neutrophils, platelets, macrophages and the complement cascade leads to the release of numerous biologically active agents including cytokines. These factors stimulate expression of adhesion molecules on the surface of the endothelium, neutrophils and leukocytes which permit binding and ultimately migration of the neutrophils and leukocytes through the extracellular matrix (ECM) and basement membrane of blood vessels and capillaries. This migration or extravasation is attributed to the action of a number of extracellular matrix degrading enzymes including matrix metalloproteinases, serine proteases and endoglycosidases (i.e. heparanases), which are released by activated neutrophils, leukocytes and/or platelets. The damage to the ECM and basement membrane results in increased vascular permeability, and infiltration of organs by neutrophils and leukocytes.

An analogous series of events is associated with septic shock except, and most critically, the key mediators of the inflammatory response are unlikely to be the same as those that cause hypovolemic shock. The initial blood volume reduction in septic shock occurs as a result of blood pooling after endotoxin stimulate neutrophil activation and the release of inflammation mediating cytokines (TNF, IL-1 and IL-6, IL-10, TGF-β etc.).

It is important to keep in mind that hypovolemic and septic shock are distinct diseases. Hypovolemic shock is a general collapse of the circulatory system that can be caused by many events including any trauma to the circulatory system (e.g. gun shot wound, automobile injury, burns, stabbing, and so on). Septic shock, on the other hand, is caused by bacterial infection. Thus, as mentioned above, the causes of these diseases are highly likely to be distinct.

Ischemia/reperfusion injury (I/RI) is another instance where inflammation mediated cell and organ damage result after a reduced blood flow state (ischemia).

The vascular damage associated with hypovolemic shock, and the resulting infiltration of neutrophils and leukocytes into the various organs leads to tissue damage and ultimately multiple organ failure (MOF) and acute respiratory distress syndrome (ARDS). The destructive agents and mediators are numerous and include cytokines, enzymes and various other inflammatory agents. MOF and ARDS can occur in severe shock and often result in death. For therapeutic agents to be effective in shock, they must protect the microvasculature and various organs (liver, kidney, heart, spleen and gut) from failure. The importance of protecting or restoring gut function and intestinal function in hemorrhagic shock and I/R injury has been reported, and correlates with reduced septic complications, and long-term survival.

DISCLOSURE OF THE INVENTION

The methods and compositions of the invention are preferably utilized for preventing or treating certain diseases that have as their underlying cause the activation and/or the expression of unwanted matrix metalloprotease activity. Such diseases include skin disorders, keratoconus, restenosis, hypovolemic shock, wounds, ulcers, particularly of the cornea or mouth or skin, or those disease states that are benefitted by uncontrolled angiogenesis, reproductive diseases or conditions such as premature cervical dilation, anti fertility, benign prostatic hypertrophy, and endometriosis. Regarding the latter, the invention is directed to a method for treating cancer, preferably by inhibiting angiogenesis which facilitates or is required for the growth and spread of cancer throughout a patients body. Further diseases that are prevented or treatable by the invention compounds include those mediated by unwanted lymphocyte infiltration into tissues or organs, such as that which occurs during and is responsible for organ rejection.

Some members of the class of matrix metalloprotease inhibitors are known in the art; others are described and claimed in U.S. Ser. No. 07/747,751, filed 20 Aug. 1991; Ser. No. 07/747,752, filed 20 Aug. 1991; Ser. No. 07/615,798, filed 21 Nov. 1990; U.S. Pat. No. 4,996,358; EP 0497192; WO 92/09565; and EP 0498665, the disclosures of which are incorporated herein by reference.

All patents, patent applications and publications discussed or cited herein are understood to be incorporated by reference to the same extent as if each individual publication or patent application was specifically and individually set forth in its entirety.

A summary of the art-known synthetic matrix metalloprotease inhibitors is found in EP application 423,943 published 24 Apr. 1991. This application assembles the structures of the synthetic matrix metalloproteases known in the art and claims their use in the treatment of demyelinating diseases of the nervous system. The present invention is directed to the use of these compounds, as well as those disclosed in the above-referenced U.S. applications, for the above described uses, and other uses set forth below.

Another object of the present invention is the description of improved, efficient and cost effective methods for the synthesis of matrix metalloprotease inhibitors, prodrugs of the inhibitors, derivatives and analogues thereof.

FIGURES

Figure 3:
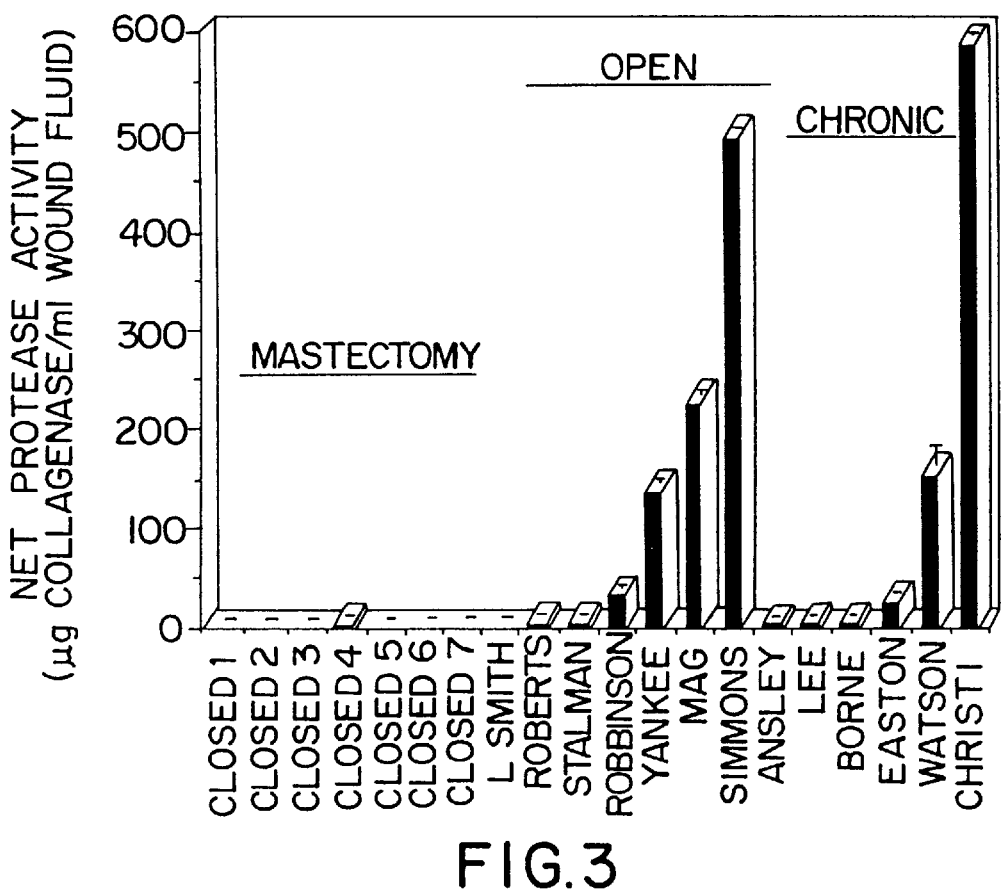

FIG. 3 compares the protease levels present in mastectomy wound fluids collects from closed (collected on different days post operation), open, or chronic wounds. Note that closed wounds exhibited marginal protease activity, while open wound fluid contained an average protease level of 199±59 μg/ml, and fluids collected from chronic wounds contained an average protease level of 125±95 μg/ml.

Figure 4:
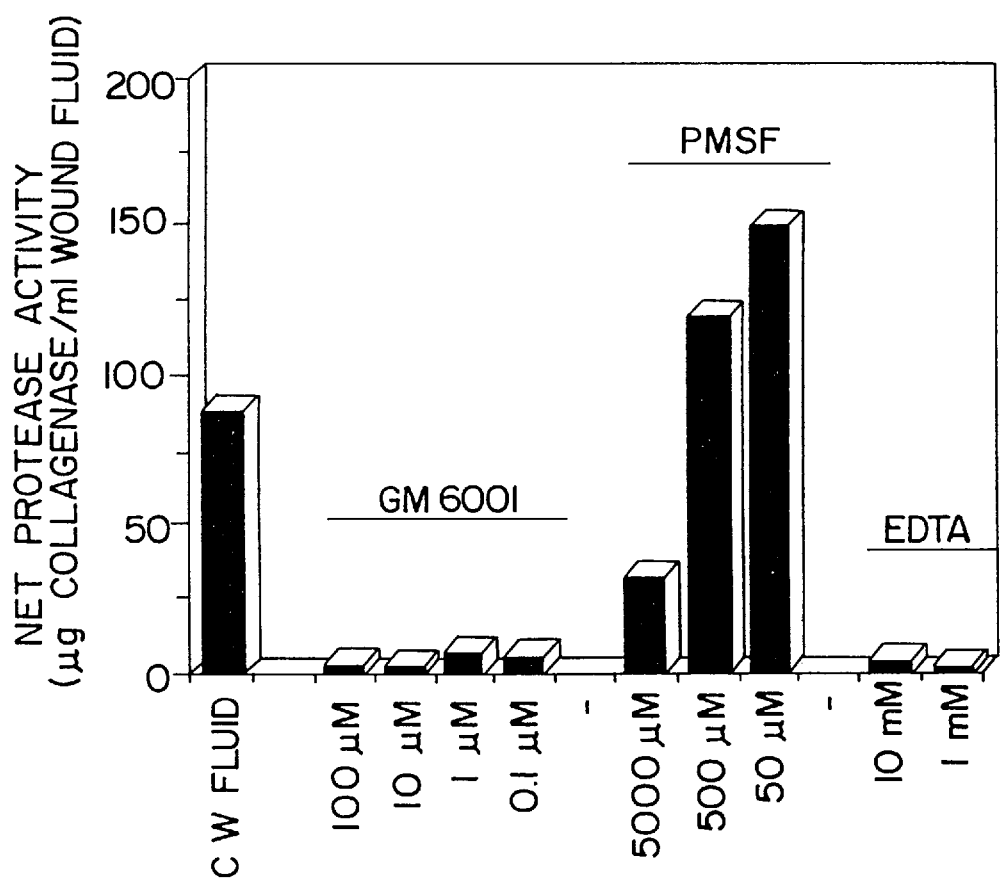

FIG. 4 shows the effect of three protease inhibitors on the protease activity of chronic wound fluid. Compound 5A very effectively inhibited proteolytic degradation of Azocoll (approximately 96% of initial proteolytic activity) at final concentrations of 40 μg/ml (100 μM) or 4 μg/ml (10 μM). EDTA, a nonspecific inhibitor of metalloproteinases, also effectively reduced protease activity, approximately 96%. PMSF, a nonspecific inhibitor of serine proteases, reduced proteolytic activity approximately 65% at a concentration of 500 μM.

Figure 5:
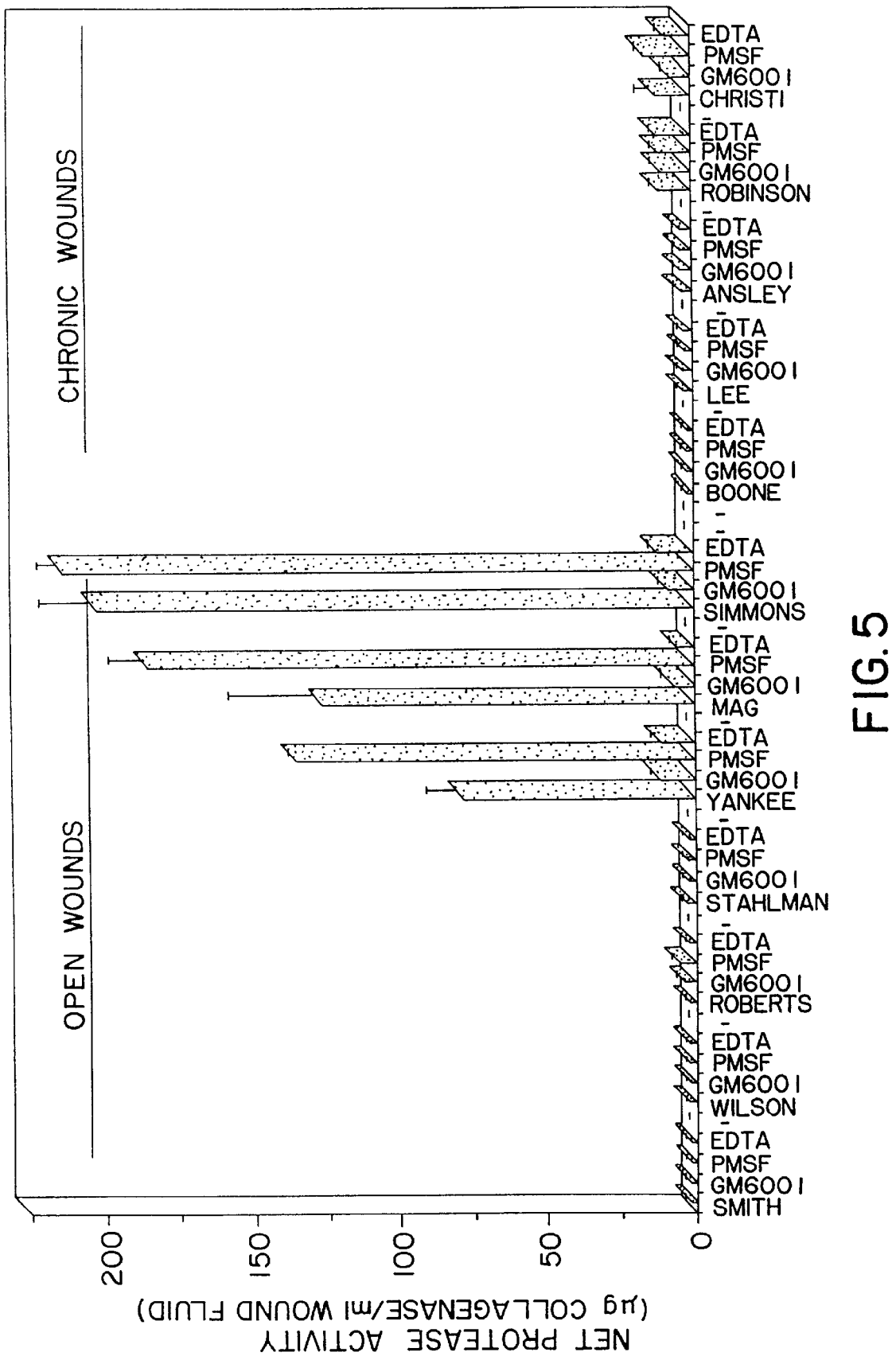

FIG. 5 shows the effects of the inhibitors, compound 5A, PMSF and EDTA on protease activity present in open and chronic wounds. Compound 5A and EDTA were very effective inhibitors while PMSF did not significantly reduce the proteolytic activity of the wound fluids.

Figure 6:
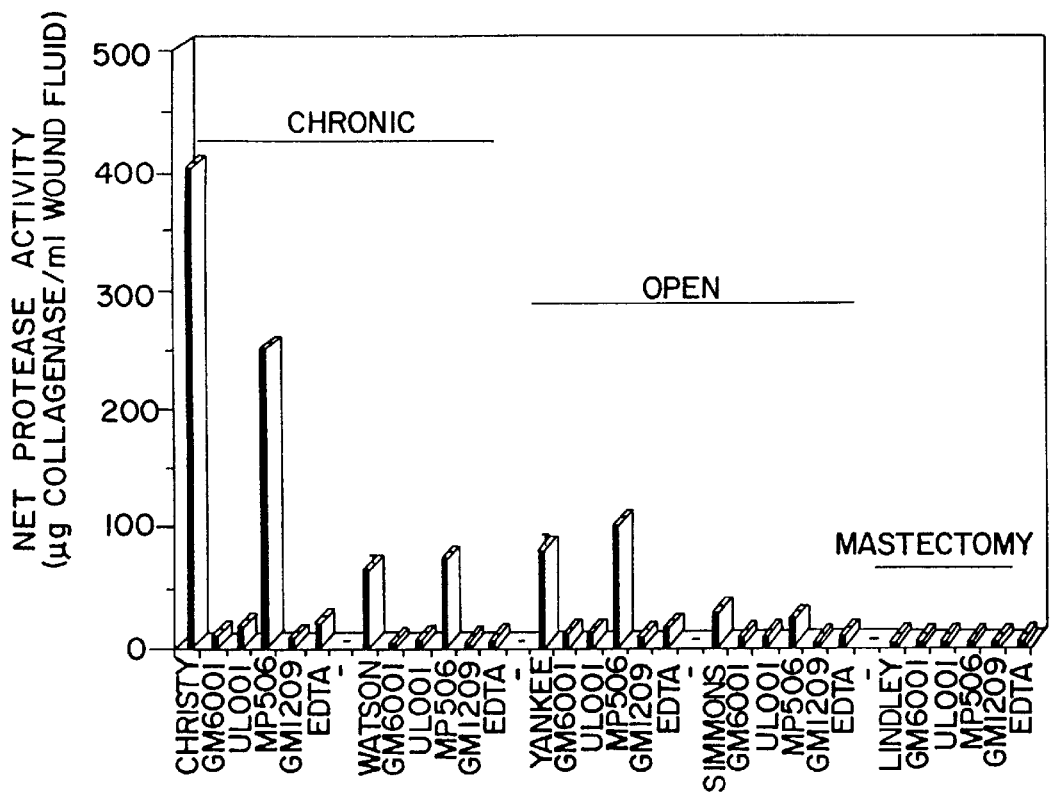

FIG. 6 shows the effects of compound 5A, S1209, UL001, MP506, and EDTA on the proteolytic degradation of Azocoll by wound fluids.

Figure 7:
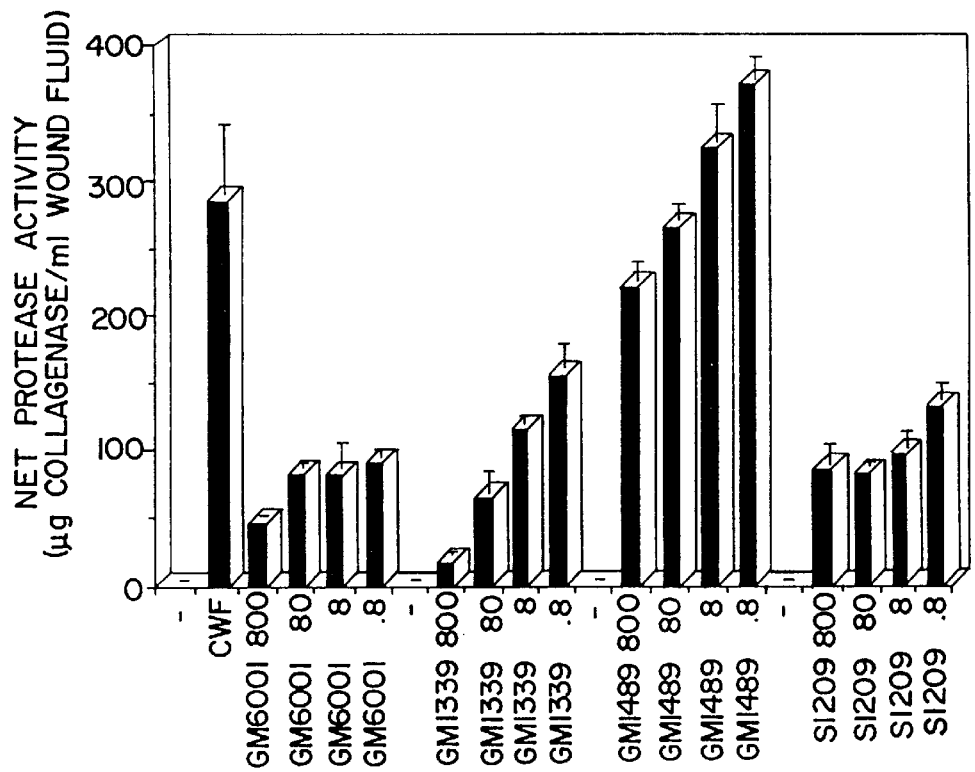

FIG. 7 shows the effects of the inhibitors compounds 5A, 21A, 39A and S1209 on protease activity present in chronic wound fluid.

Figure 8:
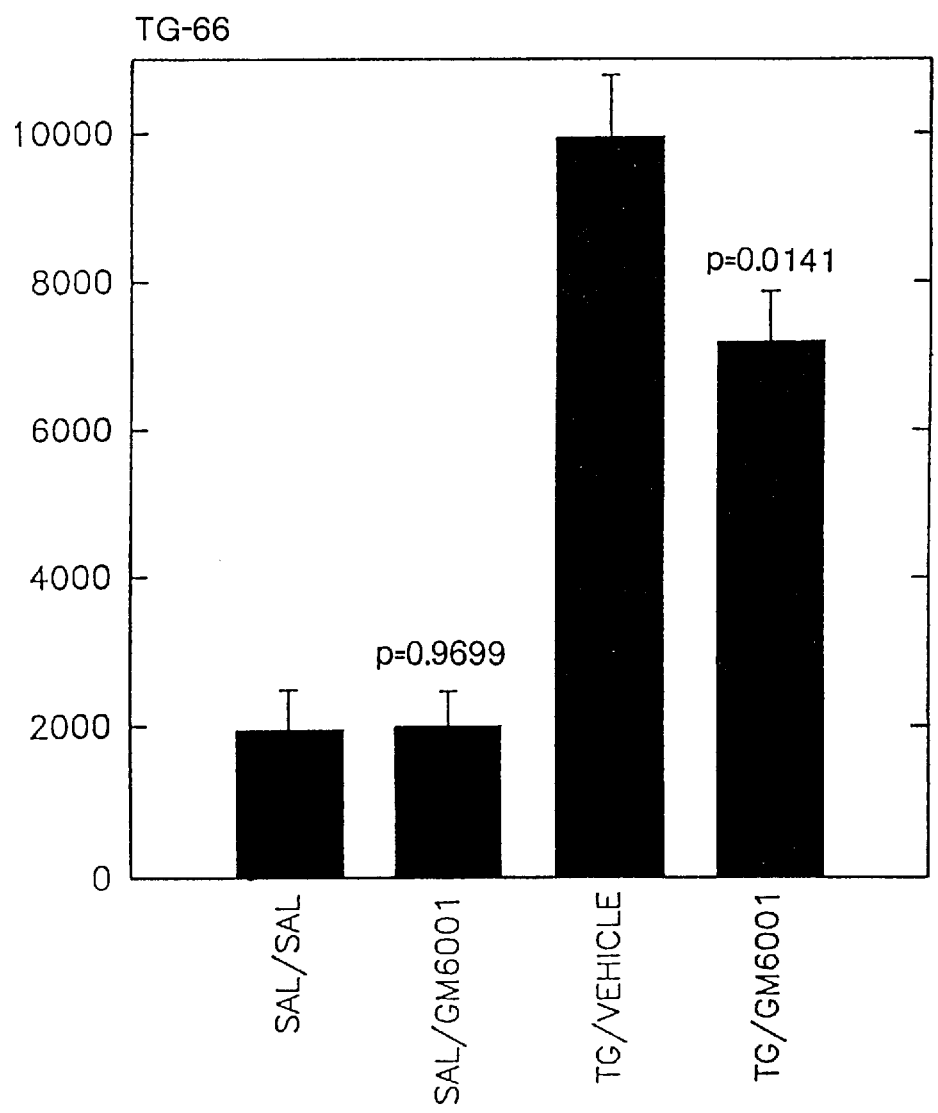

FIG. 8 shows the effects of the inhibitor compound 5A on thioglycollate induced peritonitis.

Figure 9:
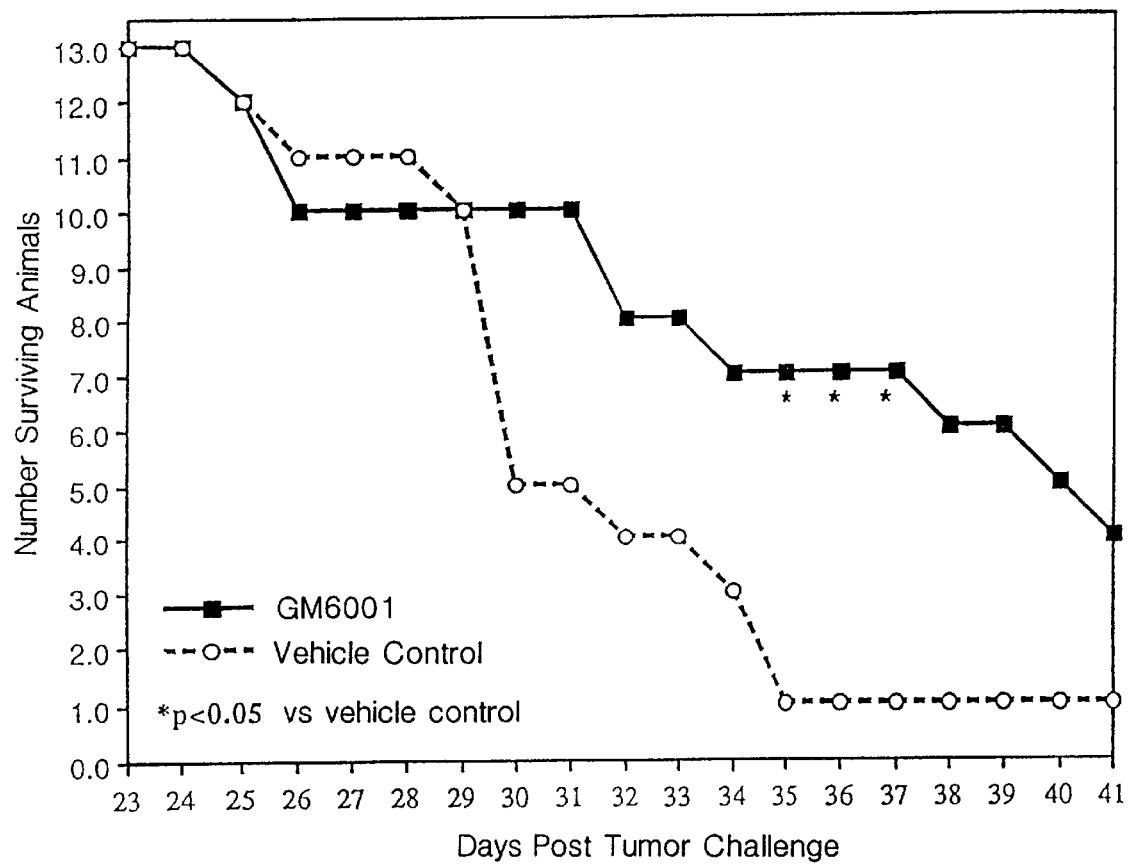

FIG. 9 shows the antimetastatic effect of compound 5A in a murine melanoma (B16-F10) model.

Figure 10A:
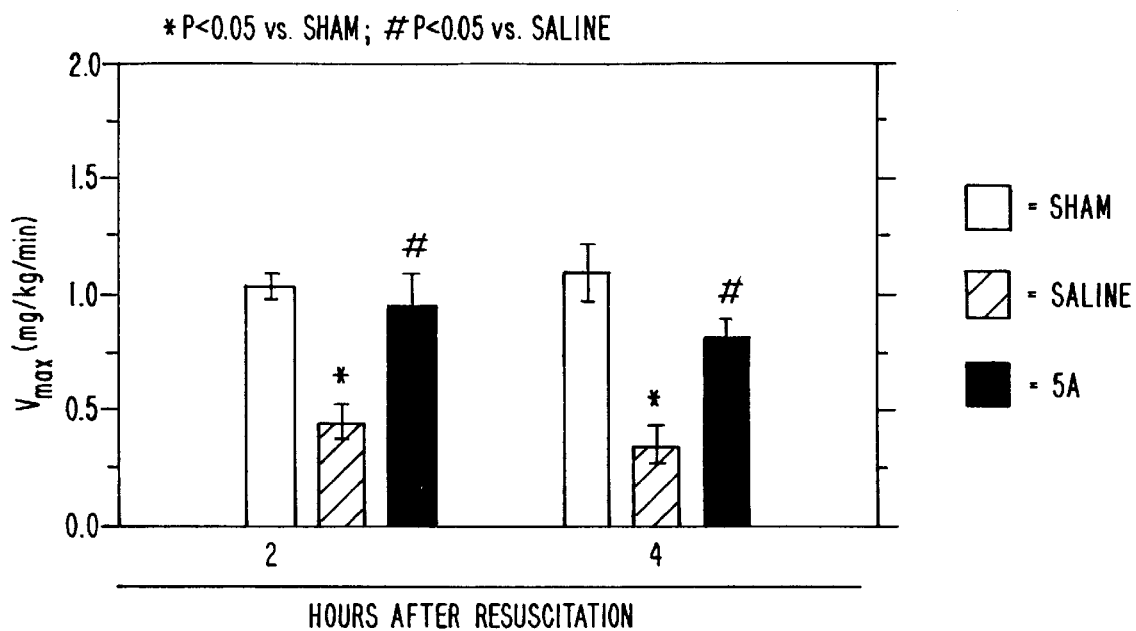

FIG. 10A is a bar graph showing changes in maximal velocity ($V_{max}$) of the clearance of indocyanine green (ICG) (active transport process) in sham-operated (Sham), normal saline-treated (Saline), and 5A treated rats at 2 and 4 h after the initiation of crystalloid resuscitation following hemorrhage. There were 6 animals in each group. The trauma-hemorrhage and resuscitation protocol and 5A infusion procedure is described in Example 51. Data are presented as means±SE and compared by one-way ANOVA and Tukey's test. *$P<0.05$ as compared with sham-operated group; #$P<0.05$ as compared with saline-treated group.

Figure 10B:
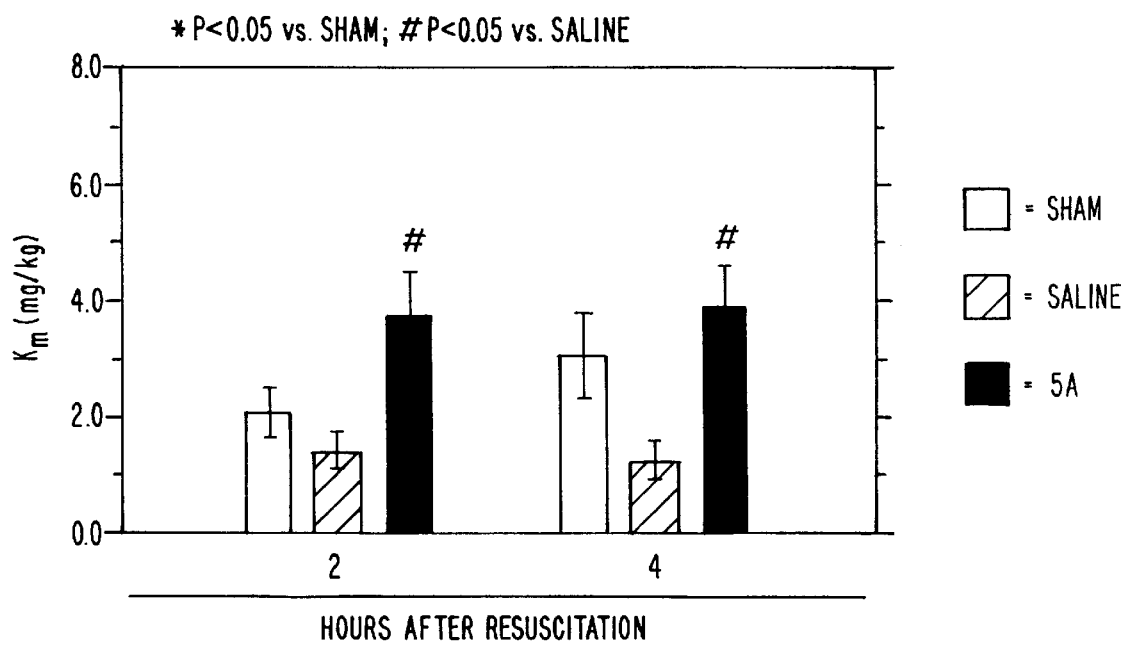

FIG. 10B is a bar graph showing changes in the efficiency ($K_m$) of the indocyanine green (ICG) transport in sham-operated (Sham), normal saline-treated (Saline), and 5A treated rats at 2 and 4 h after the initiation of crystalloid resuscitation. See the legend to FIG. 10A for further details.

Figure 11A:
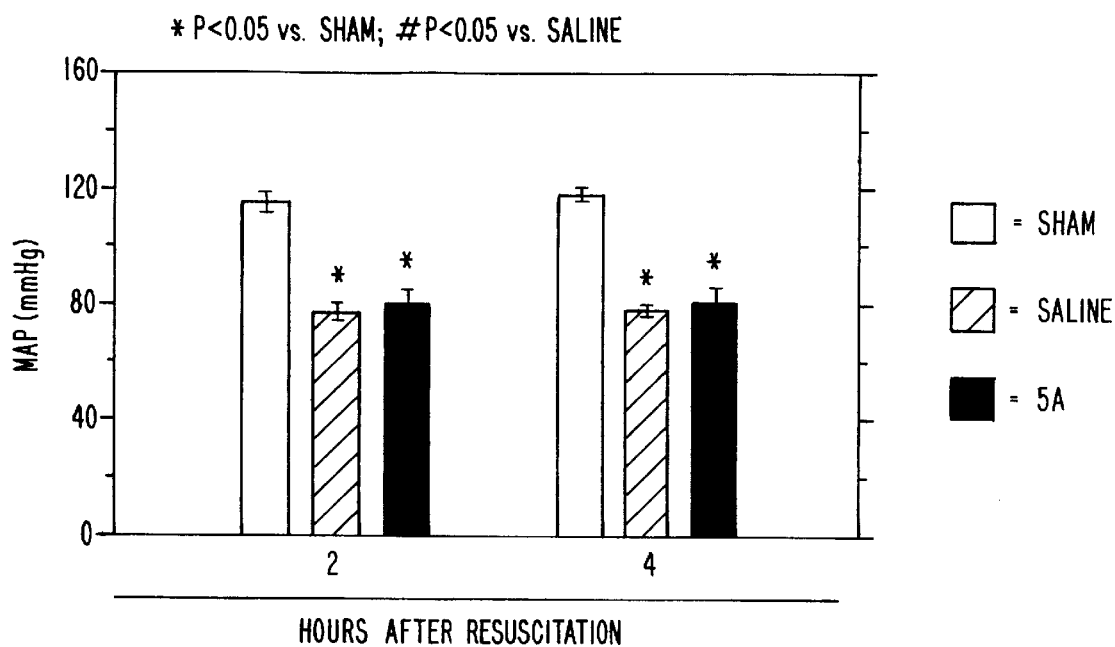

FIG. 11A is a bar graph showing changes in mean arterial pressure (MAP) in sham-operated (Sham), normal saline-treated (Saline), and 5A treated rats at 2 and 4 h after the initiation of crystalloid resuscitation. See the legend to FIG. 10A for further details.

Figure 11B:
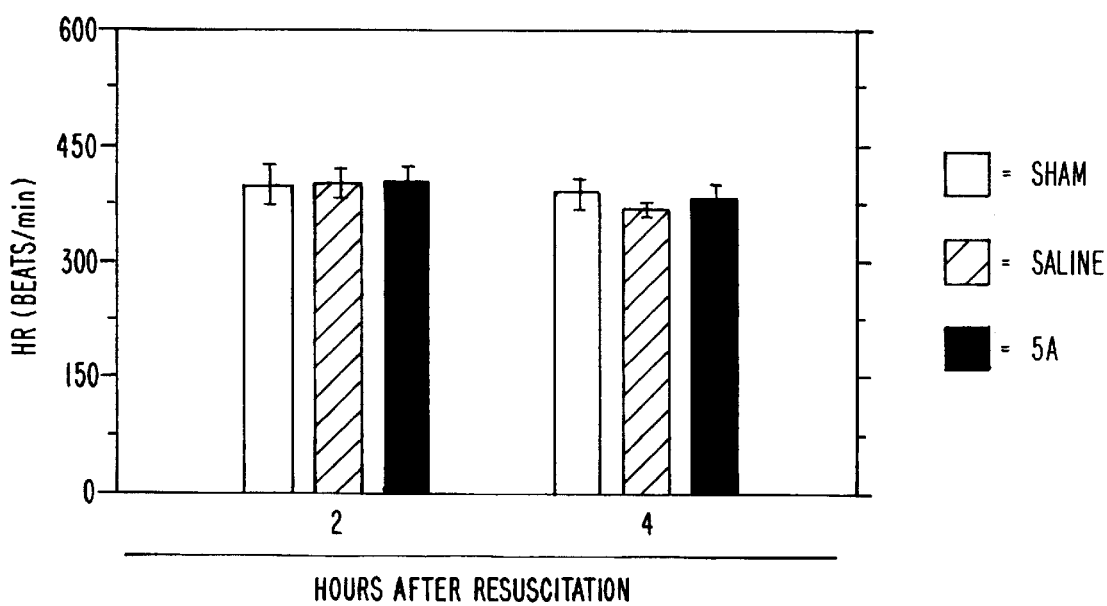

FIG. 11B is a bar graph showing changes in heart rate (HR) in sham-operated (Sham), normal saline-treated (Saline), and 5A treated rats at 2 and 4 h after the initiation of crystalloid resuscitation. See the legend to FIG. 10A for further details.

Figure 12A:
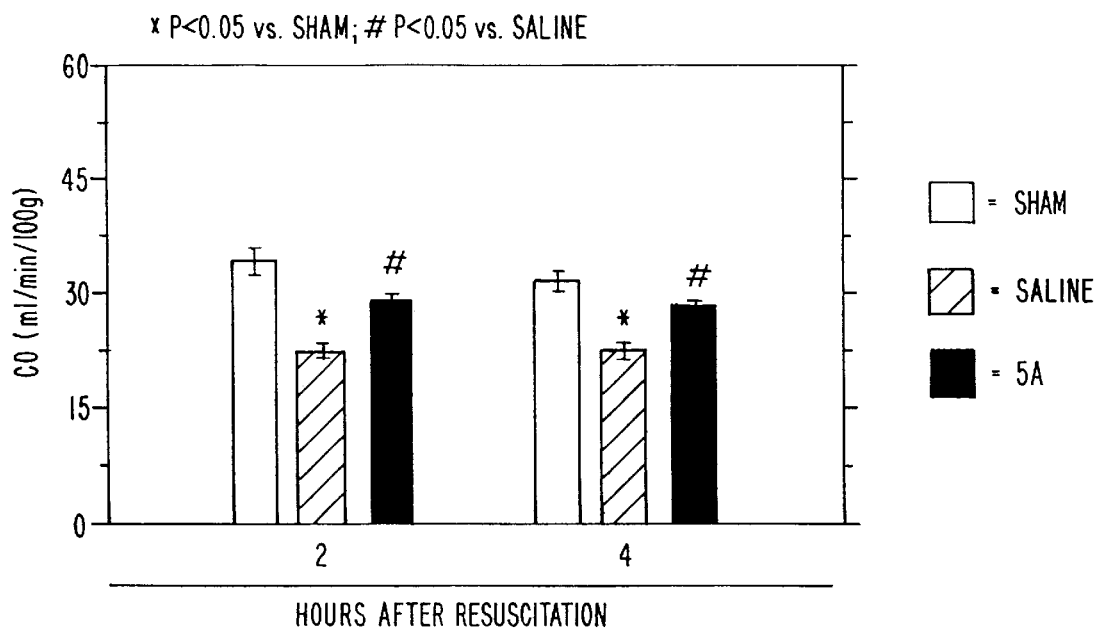
Figure 12B:
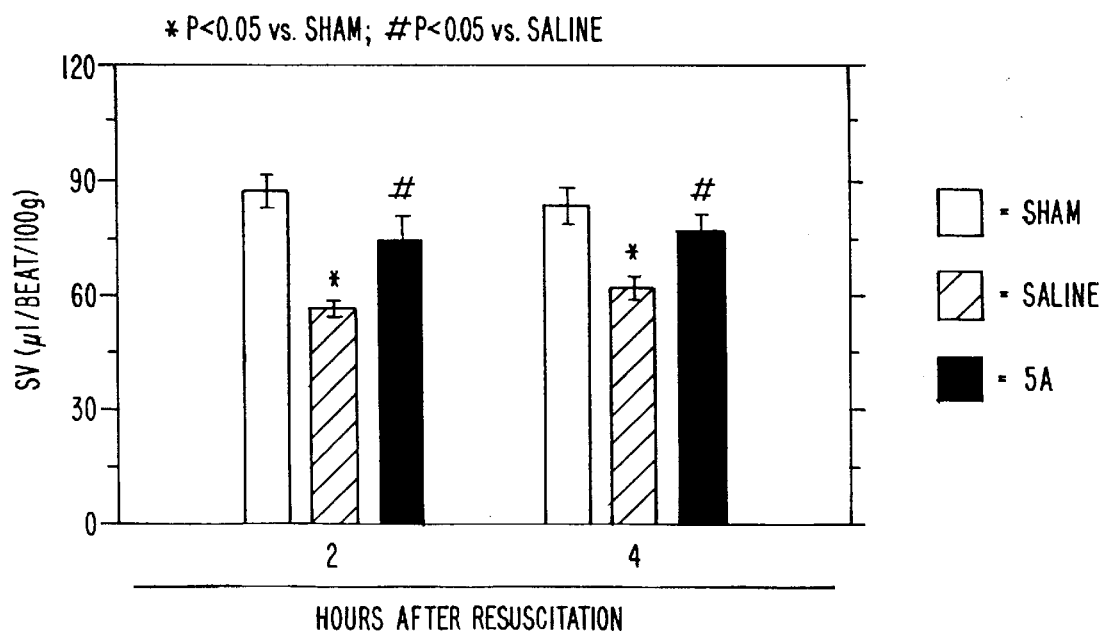
Figure 12C:
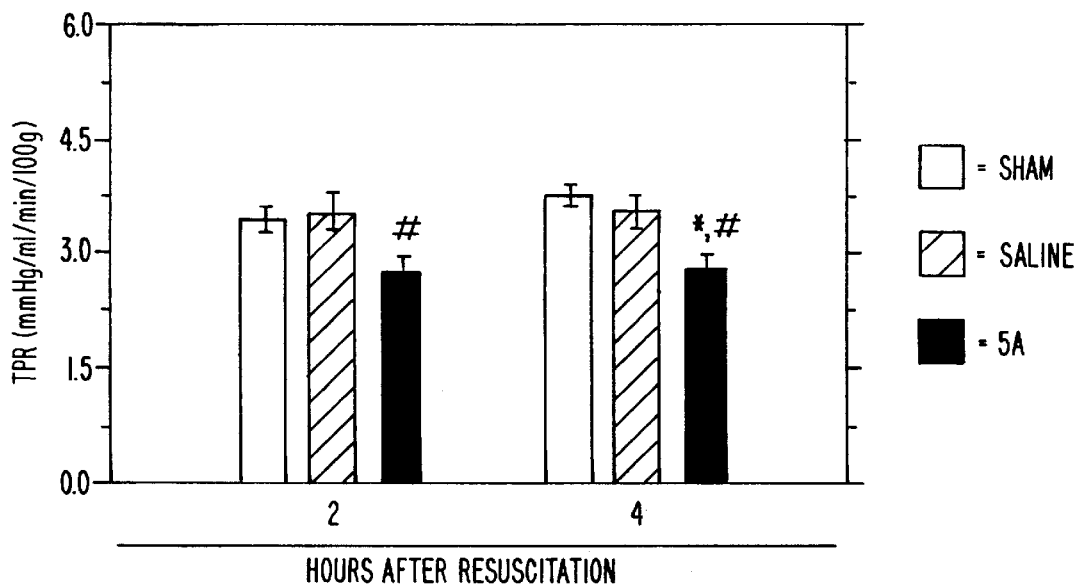

FIG. 12 includes graphs A, B and C showing changes in cardiac output (CO, A), stroke volume (SV, B), and total peripheral resistance (TPR, C) in sham-operated (Sham), normal saline-treated (Saline), and 5A treated rats at 2 and 4 h after the initiation of crystalloid resuscitation. See the legend to FIG. 10A for further details.

FIG. 13 includes graphs A, B, C and D showing changes in organ surface microvascular blood flow (MBF) in the liver (A), Kidney (B), spleen (C), and small intestine (D) in sham-operated (Sham), normal saline-treated (Saline), and 5A treated rats at 2 and 4 h after the initiation of crystalloid resuscitation. See the legend to FIG. 10A for further details.

Figure 14:
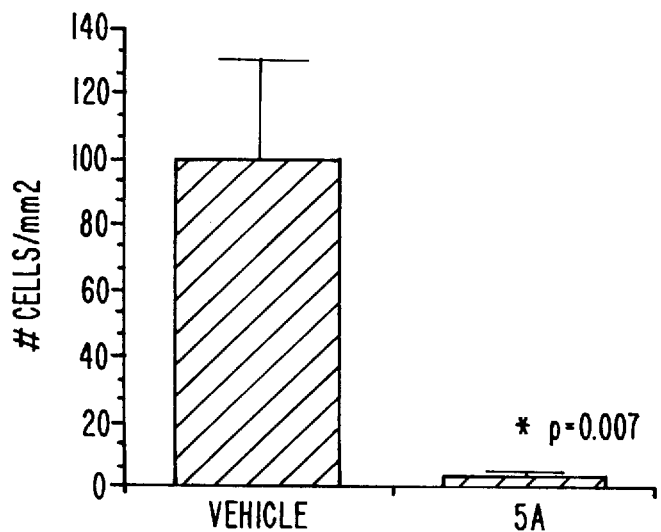

FIG. 14 shows the effects of the inhibitor 5A in the anti-restenotic assay (4 day). Administration of 5A caused a significant decrease in number of cells per unit area when compared to CMC treated controls.

Figure 15:
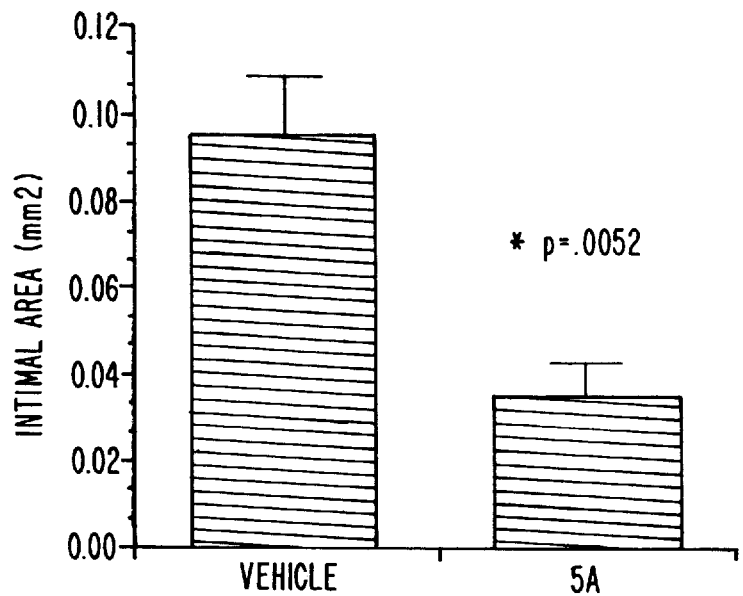

FIG. 15 shows the effects of the inhibitor 5A in the anti-restenotic assay (10 day). Administration of 5A caused a significant decrease in intimal cross-sectional area when compared to CMC treated controls.

MODES OF CARRYING OUT THE INVENTION

The inhibitory compounds of the invention are synthetic inhibitors of mammalian matrix metalloproteases. Matrix metalloproteases include without limitation human skin fibroblast collagenase, human skin fibroblast gelatinase, human neutrophil collagenase and gelatinase, and human stromelysin. These are zinc-containing metalloprotease enzymes, as are the angiotensin-converting enzymes and the enkephalinases. As used herein, "mammalian matrix metalloprotease" means any zinc-containing enzyme found in mammalian sources that is capable of catalyzing the breakdown of collagen, gelatin or proteoglycan under suitable assay conditions.

Appropriate assay conditions can be found, for example, in U.S. Pat. No. 4,743,587, which references the procedure of Cawston, et al., *Anal Biochem* (1979) 99:340–345, use of a synthetic substrate is described by Weingarten, H., et al., *Biochem Biophys Res Comm* (1984) 139:1184–1187. Any standard method for analyzing the breakdown of these structural proteins can, of course, be used. The matrix metalloprotease enzymes referred to in the herein invention are all zinc-containing proteases which are similar in structure to, for example, human stromelysin or skin fibroblast collagenase.

The ability of candidate compounds to inhibit matrix metalloprotease activity can, of course, be tested in the assays described above. Isolated matrix metalloprotease enzymes can be used to confirm the inhibiting activity of the invention compounds, or crude extracts which contain the range of enzymes capable of tissue breakdown can be used.

Specifically, assay of inhibition activity can be conducted as follows. Inhibitors may be assayed against crude or purified human skin fibroblast collagenase, or purified human gingival fibroblast collagenase using the synthetic thiol ester substrate at pH 6.5 exactly as described by Kortylewicz & Galardy, *J Med Chem* (1990) 33:263–273, at a collagenase concentration of 1–2 nM. The candidate inhibitors are tested for their ability to inhibit crude collagenase and gelatinase from human skin fibroblasts, crude collagenase and gelatinase from purulent human neutrophils in this assay. The results may be set forth in terms of Ki, i.e., the calculated dissociation constant for the inhibitor complex with enzyme. Ki values for effective inhibitors are ≦500 nM for purified enzyme in this assay. For purified human skin collagenase, excellent inhibitors show Ki values of ≦10 nM. Assays for inhibition of human stromelysin are conducted as described by Teahan, J., et al., *Biochemistry* (1989) 20:8497–8501.

Assay of inhibition activity can be conducted using a fluorogenic substrate developed by Knight et al., *FEBS Letters* (1992) 296:263. This method uses a fluorometer to determine the rate of substrate hydrolysis in a 96 well plate format. Reaction rates are determined at several substrate concentrations, and multiple inhibitor levels. The data are analyzed by Lineweaver-Burk, Dixon and Henderson plot analyses (*Enzyme Kinetics* (1975) Irwin Segal (John Wiley & Sons, Inc., publishers), and as described by Henderson, *Biochem J.* (1972) 127:321). The substrate levels range from 10–30 μM. The inhibitor levels are chosen to give 0–90% inhibition (0–500 nM). Inhibitors may be assayed against purified 72 kD gelatinase, 92 kD gelatinase, neutrophil collagenase, stromelysin or other proteases as appropriate. The enzymes are activated at 37° C. with APMA (4-aminophenylmercuric acetate), and the assays are carried out at room temperature.

The synthetic compounds that are successful in these assays for mammalian matrix metalloprotease inhibition are generally small molecules containing at least one amide bond and have a variety of sidechain substituents. Examples of such compounds known in the art are given in EP application 423,943 as set forth below in formulae I–XIV.

U.S. Pat. No. 4,263,293 (Squibb) describes compounds of formula (I):

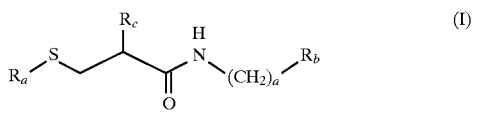

wherein $R_a$ is hydrogen, $C_{2-10}$ alkanoyl or arylcarbonyl; $R_b$ is 1-pyrrolidinyl, 1-piperidinyl, 4-morpholinyl, 1-piperazinyl or 4-alkyl-1-piperazinyl; $R_c$ is $C_{3-8}$ alkyl, $C_{3-7}$ cycloalkyl, aryl or aralkyl; and a is an integer of 1 to 20.

Compounds of formula (I) are described as effective in inhibiting mammalian collagenase and for use in reducing the adverse effects of collagenase in a mammal host.

U.S. Pat. No. 4,595,700 (Searle) describes compounds of formula (II):

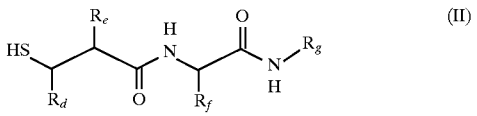

wherein $R_d$ represents lower alkyl, phenyl or phenyl lower alkyl; $R_e$ and $R_g$ represent lower alkyl; and $R_f$ represents lower alkyl, benzyloxy $C_{1-6}$ alkyl, $C_{1-6}$ alkoxybenzyl or benzyloxybenzyl.

Compounds of formula (II) are described as collagenase inhibitors having utility in the treatment of rheumatoid arthritis and related diseases in which collagenolytic activity is a contributing factor.

International Patent Application WO88/06890 (Research Corp. Technologies Inc.) describes compounds of formula (III):

wherein $R_h$ is hydrogen, $C_{1-10}$ alkyl, $C_{2-10}$ alkanoyl or $C_{7-11}$ aroyl; $R_i$ is hydrogen or $C_{1-6}$ alkyl; $R_j$ is hydrogen, $C_{2-10}$ alkyl, $C_{3-6}$ cycloalkyl, aryl or arylalkyl, wherein the aryl moiety has from 6 to 10 carbon atoms; $AA_1$ is a hydrophobic amino acid; $AA_2$ is an amino acid selected from alanine, glycine, leucine, isoleucine and phenylalanine; $AA_3$ is any amino acid; B is $-NH_2$, $-OH$, $-OCH_3$ or $-OCH_2CH_3$; b is 0 or 1; and c is 0, 1 or 2.

Compounds of formula (III) are described as effective inhibitors of mammalian collagenase activity which may be employed in the treatment of any mammalian disease in which collagenase has been implicated as a causative factor.

European Patent Publication No. 273689 (Beecham) describes compounds of formula (IV):

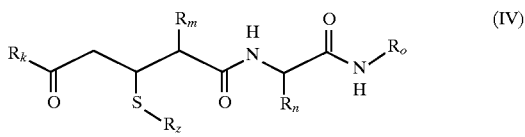

wherein $R_k$ is hydroxy, alkoxy, aryloxy, aralkyloxy, $-NR_pR_q$ where $R_p$ and $R_q$ are hydrogen or alkyl, or $R_p$ and $R_q$ together with the nitrogen atom to which they are bonded form a 5- to 7-membered ring optionally including a further heteroatom, $-NHCH(R_r)COR_s$
where $R_r$ is hydrogen, alkyl optionally substituted by hydroxy, alkoxy, $-NR_pR_q$ guanidine, $-CO_2H$, $-CONH_2$, $-SH$, $-S$-alkyl or $-CH_2-A_r$ where $A_r$ is optionally substituted aryl, and $R_s$ is hydroxy, alkoxy or $-NR_pR_q$; $R_2$ is hydrogen, alkanoyl or aroyl; $R_m$ is $C_{3-6}$ alkyl; $R_n$ is hydrogen, alkyl, $-CH_2R_t$ where $R_t$ is optionally substituted phenyl or heteroaryl, or $R_n$ is a group $-CH-(R_u)O-R_v$ where $R_u$ is hydrogen or alkyl and $R_v$ is hydrogen, alkyl or $-CH_2Ph$ where Ph is optionally substituted phenyl; $R_o$ is hydrogen, alkyl, or $-CH(R_w)COR_x$ where $R_w$ is hydrogen or alkyl and $R_x$ is hydroxy, alkoxy or $-NR_pR_q$.

European Patent Publication No. 322184 (Beecham) describes compounds of formula (IV) wherein $R_k$ is hydrogen, alkyl or optionally substituted aryl and variables $R_l$, $R_m$, $R_n$ and $R_o$ are as hereinbefore defined for compounds of formula (IV) in European Patent publication No. 273689.

Compounds of formula (IV) are described as collagenase inhibitors having utility in the treatment of disorders resulting from collagenolytic activity.

European Patent Publication No. 358305 (corresponding to U.S. patent application Ser. No. 367961) (Beecham) describes compounds of formula (V):

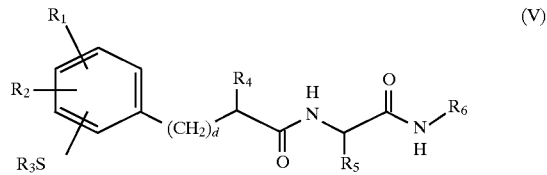

Wherein $R_1$ and $R_2$ are independently hydrogen, alkyl, alkoxy, halogen or $CF_3$; $R_3$ is hydrogen, alkanoyl, aroyl in which the aryl moiety is optionally substituted, or a group R—S— where R is an organic residue such that the group R—S— provides an in vivo-cleavable disulphide bond; $R_4$ is $C_{3-6}$ alkyl, $R_5$ is hydrogen, alkyl, $-CH_2R_7$ where $R_7$ is optionally substituted phenyl or heteroaryl, or $R_7$ is a group $-CH(R_8)OR_9$ where $R_8$ is hydrogen or alkyl, and $R_9$ is hydrogen, alkyl, or $-CH_2Ph$ there Ph is optionally substituted phenyl; $R_6$ is hydrogen, alkyl, $-CH(R_{10})COR_{11}$ where $R_{10}$ is hydrogen or alkyl and $R_{11}$ is hydroxy, alkoxy, or $-NR_{12}R_{13}$ where each of $R_{12}$ and $R_{13}$ is hydrogen or alkyl, or $R_{12}$ and $R_{13}$ together with the nitrogen atom to which they are bonded form a 5-, 6- or 7-membered ring with an optional oxygen, sulphur or optionally substituted nitrogen atom in the ring; or $R_5$ and $R_6$ joined as $-(CH_2)_e-$ where e is an integer from 4 to 12; and d is an integer from 1 to 3.

Compounds of formula (V) are described as collagenase inhibitors having utility in the treatment of disorders resulting from collagenolytic activity.

U.S. Pat. No. 4,599,361 (Searle) and European Patent Publication No. 214639 (Searle) describe compounds of formula (VI):

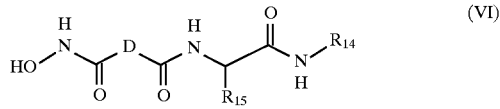

wherein $R_{14}$ is $C_{1-6}$ alkyl; $R_{15}$ is $C_{1-6}$ alkyl, benzyl, benzyloxybenzyl, ($C_{1-6}$ alkoxy)benzyl or benzyloxy($C_{1-6}$ alkyl); and D is a group —(CHR$_{16}$–CHR$_{17}$)— or —(CR$_{16}$–CR$_{17}$)— where $R_{16}$ is hydrogen, $C_{1-6}$ alkyl, phenyl or phenyl($C_{1-6}$ akyl) and $R_{17}$ is hydrogen, ($C_{1-6}$ alkyl), phenyl($C_{1-6}$ alkyl), cycloalkyl or cycloalkyl($C_{1-6}$ alkyl).

Compounds of formula (VI) are described as inhibitors of mammalian collagenase having utility in the treatment of rheumatoid arthritis and related diseases in which collagenolytic activity is a contributing factor.

European Patent Publication No. 274453 (Laboratoire Roger Bellon) describes compounds of formula (VII):

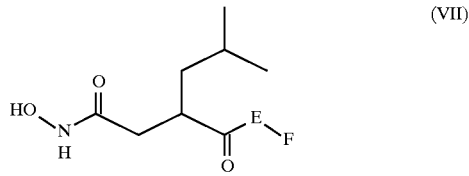

Wherein E represents an amino acid residue selected from valine, lysine, norleucine or methionine and F represents amino or $C_{1-2}$ alkylamino in which the alkyl moiety is substituted by phenyl or trifluoromethylphenyl.

Compounds of formula (VII) are described as inhibitors of collagenase having utility in the treatment of disorders implicated in the destruction of collagen by collagenase.

European Patent Publication No. 231081 (ICI Americas Inc.) describes compounds of formula (VIII):

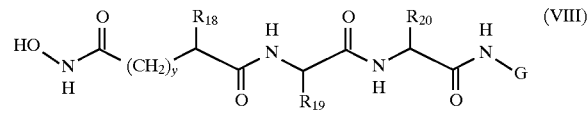

wherein $R_{18}$ is a straight or branched chain $C_{2-7}$ alkyl group; $R_{19}$ and $R_{20}$ are each an amino acid residue; y is 1 or 2; and G is hydrogen or —CH($R_{21}$)CONH$_2$ where $R_{21}$ is an amino acid residue.

Compounds of formula (VIII) are described as inhibitors of the activity of metalloproteases, including collagenase, having utility in the treatment of diseases in which the activity of such enzymes has been implicated.

European Patent Publication No. 236872 (Hoffman-La Roche) describes compounds of formula (IX):

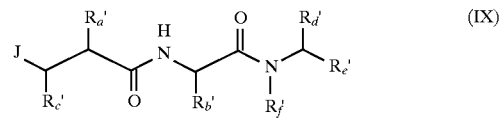

wherein $R_a'$ is $C_{2-5}$ alkyl; $R_b'$ is a side-chain of a natural α-amino acid in which any functional group is optionally protected, any amino group is optionally acylated and any carboxyl group is optionally amidated with the proviso that $R_b$ is not hydrogen or methyl; $R_c$ is hydrogen, amino, hydroxy, mercapto, $C_{1-6}$ alkyl, $C_{1-6}$ alkoxy, $C_{1-6}$ alkylamino-, $C_{1-6}$ alkylthio-, aryl $C_{1-6}$ alkyl-, amino $C_{1-6}$ alkyl-, hydroxy $C_{1-6}$ alkyl-, mercapto $C_{1-6}$ alkyl- or carboxy $C_{1-6}$ alkyl- wherein any amino, hydroxy, mercapto or carboxy group is optionally protected, any amino group is optionally acylated and any carboxy group is optionally amidated; $R_d'$ is hydrogen or methyl; $R_e'$ is hydrogen, $C_{1-6}$ alkyl, $C_{1-6}$ alkoxy $C_{1-6}$ alkyl, di-($C_{1-6}$ alkoxy)methyl, carboxy, $C_{2-7}$ alkanoyl, $C_{1-6}$ alkoxycarbonyl, arylmethoxycarbonyl, $C_{1-6}$ alkylaminocarbonyl or arylaminocarbonyl; $R_f'$ is hydrogen or methyl; or $R_b'$ and $R_d'$ together are —(CH$_2$)$_f$— where f is an integer from 4 to 11; or $R_d'$ and $R_e'$ together are (CH$_2$)$_3$; and J is —C(O)NHOH or —N(OH)CHO.

Compounds of formula (IX) are described as collagenase inhibitors having utility in the treatment of degenerative joint diseases such as rheumatoid arthritis and osteoarthritis.

European Patent Publication No. 126974 (Searle) describes compounds of formula (X):

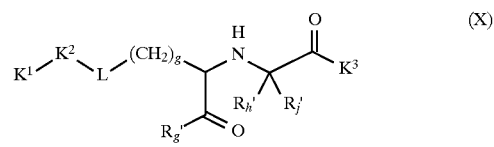

wherein g is an integer from 1 to 4; $R_g'$ represents hydroxy, alkoxy, aralkyloxy or hydroxyamino; $R_h'$ represents hydrogen or alkyl; $R_i'$ represents hydrogen, alkyl optionally substituted by one or more groups selected from hydroxy, alkoxy, aryloxy, aralkyloxy, mercapto, alkylthio, arylthio, alkylsuphinyl, alkylsulphonyl, carboxy, carboxamido, carboxyalkyl, carboxyaralkyl, aralkoxycarbonylamino, amino, dialkylamino, acylamino, aroylamino and trihalomethyl, aralkyl optionally substituted on the aryl moiety by one or more groups selected from halogen, alkyl hydroxy, alkoxy, aralkoxy, amino, aminomethyl, cyano, alkylamino, dialkylamino, carboxy, sulphonamido, alkylthio, nitro and phenyl, or heteroaralkyl; L represents NR$_j'$ wherein R$_j'$ represents hydrogen or alkyl, or L represents a direct chemical bond; when L represents NR$_j'$, K$^1$ represents a group $R_k'$ wherein $R_k'$ is hydrogen, alkyl, aralkyl, acyl, aroyl, aralkylacyl, alkoxycarbonyl, aralkoxycarbonyl, aryl optionally substituted by one or more groups selected from halogen, alkyl, hydroxy, alkoxy, aralkoxy, aralkoxyamino, aminomethyl, cyano, acylamino, dialkylamino, carboxy, sulphonamido, alkylthio, nitro and phenyl; or alternatively K$^1$ represents a group $R_z'R_m'N$—C($R_n'$)($R_o'$)—C(O)— wherein $R_z'$ is $R_k'$ as defined above, $R_m'$ and $R_n'$ independently represent hydrogen, alkyl or aralkyl or together represent an alkylene chain of 2 to 4 carbon atoms so as to form with the adjacent nitrogen a 4- to 6-membered ring, and $R_o'$ is $R_i'$ as defined above; K$_2$ represents N($R_p'$)—C($R_q'$)($R_r'$)—C(O)— wherein $R_p'$ and $R_q'$ independently represent those groups as defined for $R_m'$ above, or $R_p'$ and $R_q'$ together represent an alkylene chain of 2 to 4 carbon atoms so as to form with the adjacent nitrogen a 4- to 6-membered ring, and $R_r'$ is $R_o'$ as defined above; or alternatively K$^1$ and K$^2$ together represent hydrogen, alkyl, aralkyl, heteroaralkyl, alkysulphonyl, arylsulphonyl, aralkylsulphonyl, or a group $R_s'$CO— wherein $R_s'$ represents hydrogen, alkyl, aralkyl, aryl, alkoxy, aralkoxy, alkylamino, arylamino, aralkylamino, phenethenyl, phenethynyl, dialkylamino, substituted aryl as defined above for $R_k'$, substituted aralkyl as defined above for $R_i'$, or substituted aralkoxy wherein the substituent on the aromatic moiety is as for substituted aryl under $R_k'$ above; or alternatively when L represents a direct chemical bond, K$^1$ and K$^2$ together represent hydrogen, alkyl, aryl, alkoxy, aralkoxy, substituted aryl or substituted aralkoxy wherein the substituents on the aromatic moieties are as defined for substituted aralkyl under $R_i'$, hydroxy, mercapto, alkylthio, arylthio, aralkylthio, carboxy or carboxyalkyl; and $K^3$ represents $R_t'$ or a group —N($R_p'$)—C($R_9'$)($R_r'$)—C(O)—$R_u'$ wherein $R_t'$ represents amino, alkylamino, dialkylamino, hydroxyamino or aralkylamino, $R_p'$, $R_q'$ and $R_r'$ are as defined above under $K^2$, and $R_u'$ represents amino, alkylamino, dialkylamino, alkylamino optionally substituted by amino, hydroxy, alkoxy, carboxy, carboxamido, carboxyalkyl, alkylthio, alkylsuphinyl or alkysulphonyl, hydroxyamino, alkoxyamino, aralkylamino, alkoxy, aralkoxy or alkylaminoalkoxy; with the proviso that when $K^3$ is alkylamino, then one of $R_h'$ and $R_i'$ is not hydrogen when the other is alkyl or hydroxyalkyl.

Compounds of formula (X) are described as inhibitors of mammalian collagenase which are useful in the treatment of rheumatoid arthritis and associated diseases.

European Patent Publication No. 159396 (Searle) describes compounds of formula (XI):

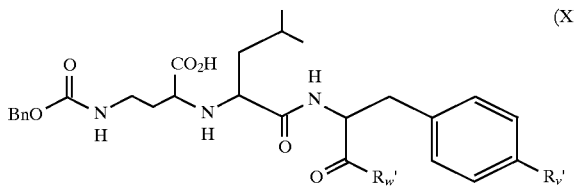

(XI)

wherein $R_v'$ represents hydroxy, alkoxy, cycloalkoxy, aralkoxy or alkoxy substituted by alkylaminocarbonyl or a group —C(O)—NH—CH)(alkyl)-C(O)—NH-alkyl; and $R_w'$ represents alkylamino or aralkylamino.

Compounds of formula (XI) wherein $R_v'$ is hydroxy, alkoxy or aralkoxy fall within the scope of compounds of formula (X) as defined above.

Compounds of formula (XI) are described as inhibitors of mammalian collagenase which are useful in the treatment of rheumatoid arthritis and related diseases.

European Patent Publication No. 232027 (ICI Americas Inc) describes compounds of formula (XII):

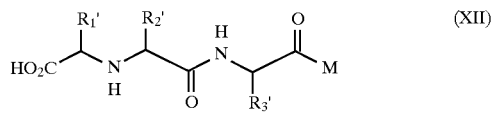

(XII)

wherein $R_1'$ is $C_{4-6}$ alkyl; $R_2'$ is $C_{4-6}$ alkyl; $R_3'$ is $C_{1-6}$ alkyl or $C_{6-10}$ aryl optionally substituted by $C_{1-4}$ alkyl or $C_{1-4}$ heteroalkyl having one or more heteroatoms independently selected from oxygen, sulphur and nitrogen; and 5A is selected from —NHR$_4'$, —OCH$_2$R$_4'$, —NH—CH(R$_5'$)—C(O)—NHR$_4'$, —NH—CH(R$_5'$)—C(O)—NH—CH—(R$_6'$)—C(O)NHR$_4'$, —NH—CH(R$_5'$)—C(O)—OCH$_2$R$_4'$, and —NH—CH(R$_5'$)—C(O)—NHCH(R$_6'$)—C(O)—OCH$_2$R$_4'$, where $R_4'$ is hydrogen, $C_{1-10}$ alkyl or $C_{6-10}$ aryl optionally substituted by $C_{1-4}$ alkyl or $C_{1-4}$ alkyl or $C_{1-4}$ heteroalkyl having one or more heteroatoms independently selected from oxygen, sulphur and nitrogen; and $R_5'$ and $R_6'$ are independently $C_{1-4}$ alkyl or $C_{6-10}$ aryl optionally substituted by $C_{1-4}$ alkyl or $C_{1-4}$ heteroalkyl having one or more heteroatoms independently selected from oxygen, sulphur and nitrogen, subject to the proviso that if the compound formula (XII) is a tripeptide terminating in —NHR$_4'$, then $R_5'$ may not be isobutyl, and if the compound of formula (XII) is a tetrapeptide terminating in —NHR$_4'$, then $R_6'$ may not be isobutyl.

Compounds of formula (XII) are described as selective, inhibitors of proteogylcanase, that are not inhibitors of collagenase which are useful whenever it is desired to inhibit the activity of proteoglycanase and particularly when it is desired to selectively inhibit the activity of proteoglycanase in the presence of collagenase.

European Patent Publication No. 320118 (Beecham) describes compounds of formula (XIII):

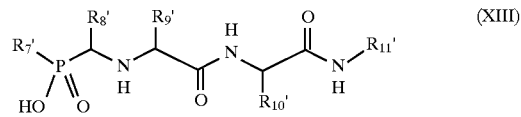

(XIII)

wherein $R_7'$ is hydrogen or hydroxy; $R_8'$ is hydrogen or alkyl; $R_9'$ is $C_{3-6}$ alkyl; $R_{10}'$ is hydrogen, alkyl —CH$_2$—Q where Q is optionally substituted phenyl or heteroaryl, or $R_{10}'$ is a group —CH($R_{12}'$)— OR$_{13}'$ where $R_{12}'$ is hydrogen or alkyl and $R_{13}'$ is hydrogen, alkyl or —CH$_2$—Ph where Ph represents optionally substituted phenyl; and $R_{11}'$ is hydrogen or alkyl.

Compounds of formula (XII) are described as collagenase inhibitors having utility in the treatment of disorders resulting from collagenolytic activity.

European Patent Publication No. 276436 (Hoffman-LaRoche) describes compounds of formula (XIV):

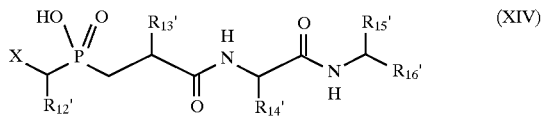

(XIV)

wherein $R_{12}'$ represents hydrogen, $C_{1-6}$ alkyl, or aryl $C_{1-6}$ alkyl; $R_{13}'$ represents $C_{2-5}$ alkyl; $R_{14}'$ represents the sidechain of a natural α-amino acid in which any functional group present is optionally protected, any amino group present is optionally acylated or sulphonylated, or any carboxyl group present is optionally amidated, subject to the proviso that $R_{14}'$ does not represent hydrogen or methyl; $R_{15}'$ represents hydrogen or methyl; or $R_{14}'$ and $R_{15}'$ together represent —(CH$_2$)$_n$— where n is an integer from 4 to 11; $R_{16}'$ represents hydrogen, $C_{1-6}$ alkyl, carboxy, $C_{1-6}$ alkoxycarbonyl or $C_{1-6}$ alkylaminocarbonyl; and X represents either a cyclic imido group derived from an aliphatic or aromatic dicarboxylic acid, from an N-carboxyamino acid, from an azadicarboxylic acid or from an O-carboxyhydroxy acid, or a group $R_{21}'$—NR$_{20}'$—CH($R_{19}'$)—C(O)—NR$_{18}'$—CH($R_{17}'$)—C(O)—NH— in which $R_{17}'$ represents the sidechain of a natural α-amino acid in which any functional group present is optionally protected, any amino acid group present is optionally acylated or sulphonylated, or any carboxyl group present is optionally amidated; $R_{18}'$ represents hydrogen or $R_{17}'$ and $R_{18}'$ together represent a trimethylene group; $R_{19}'$ represents the side-chain of a natural α-amino acid in which any functional group present is optionally protected, any amino group present is optionally acylated or sulphonylated, or any carboxyl group present is optionally amidated; $R_{20}'$ represents hydrogen; or $R_{19}'$ and $R_{20}'$ together represent a trimethylene group; and $R_{21}'$ represents a protecting group or an acyl, $C_{1-6}$ alkylsulphonyl or arylsulphonyl group, with L-stereochemistry at the chiral centres bearing $R_{17}'$ and $R_{19}'$.

Compounds of formula (XIV) are described as inhibitors of the enzyme collagenase having utility in the control or prevention of degenerative joint diseases such as rheumatoid arthritis and osteoarthritis.

EP application 0 497 192 discloses matrix metalloprotease inhibitors of formula (XV):

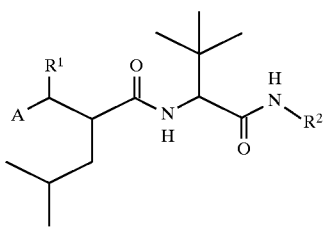

(XV)

wherein A represents the group

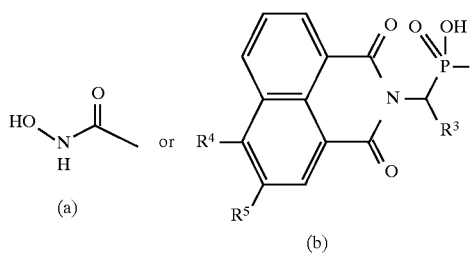

$R^1$ represents hydrogen, amino, protected amino, acylamino or lower alkyl optionally substituted by aryl, hydroxy, protected hydroxy, amino, protected amino, acylamino, maleimido, succinimido, naphthalimido, 2,3-dihydro-1,3-dioxo-1H-benz[d,e]isoquinol-2-yl, carboxy, protected carboxy, carbamoyl, mono(lower alkyl)carbamoyl, di(lower alkyl)carbamoyl, di(lower alkyl)amino, carboxy-lower alkanoylamino, pyrrolidino or morpholino; $R^2$ represents hydrogen or lower alkyl optionally substituted by aryl, amino, protected amino, di(lower alkyl)amino, guanidino, carboxyl, protected carboxyl, carbamoyl, mono(lower alkyl) carbamoyl, di(lower alkyl)carbamoyl, di(lower alkoxy) phosphinyl, dihydroxyphosphinyl, pyrrolidino, piperidino or morpholino; $R^3$ represents hydrogen or lower alkyl optionally substituted by hydroxy, protected hydroxy, amino or protected amino; $R^4$ represents hydrogen, hydroxyl, lower alkoxy or benzyloxy; and $R^5$ represents hydrogen or halogen; and pharmaceutically acceptable salts thereof.

PTC application WO 92/09565 discloses matrix metalloprotease inhibitors of formula (XVI):

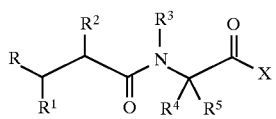

(XVI)

wherein R represents a —CONHOH, carboxyl(—CO$_2$H) or esterified carboxyl group; $R^1$ represents an optionally substituted alkyl, alkenyl, aryl, aralkyl heteroaryl or heteroarylthioalkyl group; $R^2$ represents an optionally substituted alkyl, alkenyl, cycloalkyl, cycloalkylalkyl, aryl, aralkyl, aralkoxy, or aralkylthio group, or an amino(—NH$_2$), substituted amino, carboxyl(—CO$_2$H) or esterified carboxyl group; $R^3$ represents a hydrogen atom or an alkyl group; $R^4$ represents a hydrogen atom or an alkyl group; $R^5$ represents a group —[Alk]$_n$R$^6$ where Alk is an alkyl or alkenyl group optionally interrupted by one or more —O— or —S— atoms or —N(R$^7$)— groups [where $R^7$ is a hydrogen atom or a C$_{1-6}$ alkyl group], n is zero or an integer 1, and $R^6$ is an optionally substituted cycloalkyl or cycloalkenyl group; X represents an amino(—NH$_2$), or substituted amino, hydroxyl or substituted hydroxyl group; and the salts, solvates and hydrates thereof.

EP application 0 498 665 discloses matrix metalloprotease inhibitors of formula (XVII):

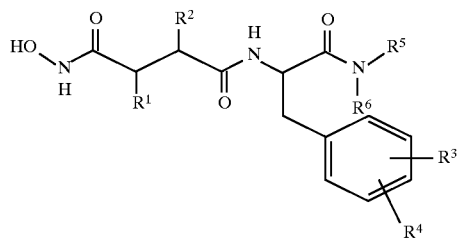

(XVII)

wherein:
$R^1$ is hydrogen, C$_1$–C$_6$ alkyl, phenyl, substituted phenyl, phenyl(C$_1$–C$_6$ alkyl), or heterocyclyl; or $R^1$ is ASO$_n$R$^7$ wherein A represents a C$_1$–C$_6$ hydrocarbon chain, optionally substituted with one or more C$_1$–C$_6$ alkyl, phenyl or substituted phenyl groups n=0, 1, 2; $R^7$ is C$_1$–C$_6$ alkyl, phenyl, substituted phenyl, phenyl(C$_1$–C$_6$ alkyl), heterocyclyl, (C$_1$–C$_6$ alkyl)acyl, thienyl or phenacyl; $R^2$ is hydrogen, C$_1$–C$_6$ alkyl, C$_2$–C$_6$ alkenyl, phenyl(C$_2$–C$_6$ alkyl) or cycloalkyl(C$_1$–C$_6$ alkyl); $R^3$ and $R^4$ are selected from hydrogen, halogen, cyano amino, amino(C$_1$–C$_6$)alkyl, amino di(C$_1$–C$_6$)alkyl, amino(C$_1$–C$_6$)alkylacyl, aminophenacyl, amino (substituted) phenacyl, amino acid or derivative thereof, hydroxy, oxy(C$_1$–C$_6$)alkyl, oxyacyl, formyl, carboxylic acid, carboxamide, carboxy(C$_1$–C$_6$) alkylamide, carboxyphenylamide, carboxy(C$_1$–C$_6$) alkyl, hydroxy(C$_1$–C$_6$)alkyl, (C$_1$–C$_6$)alkoxyoxy (C$_1$–C$_6$)alkyl or acyloxy(C$_1$–C$_6$)alkyl, (C$_1$–C$_6$) alkylcarboxylic acid, (C$_1$–C$_6$)alkylcarboxy(C$_1$–C$_6$) alkyl, amino(C$_{1-6}$)alkylacyl carboxylic acid or amino (C$_{1-6}$)alkylacyl(C$_{1-6}$)alkylcarboxylate; or $R^3$ is OCH$_2$COR$^8$ and $R^4$ is hydrogen; wherein $R^8$ is hydroxyl, C$_1$–C$_6$ oxyalkyl, C$_1$–C$_6$ oxyalkylphenyl, amino, C$_1$–C$_6$ aminoalkyl, C$_1$–C$_6$ aminodialkyl, C$_1$–C$_6$ aminoalkylphenyl, an amino acid or derivative thereof; or $R^3$ is OCH$_2$CH$_2$COR$^9$ and $R^4$ is hydrogen; wherein $R^9$ is C$_1$–C$_6$ alkyl, C$_1$–C$_6$ alkylphenyl, phenyl, substituted phenyl, (C$_1$–C$_6$ alkyl)acyl, or phenacyl; or $R^3$ is OCH$_2$CN and $R^4$ is hydrogen; $R^5$ is hydrogen or C$_1$–C$_6$ alkyl, or (C$_1$–C$_6$)alkylphenyl; $R^6$ is hydrogen or methyl; or a salt thereof; specifically excluded are compounds wherein: $R^3$=$R^4$=hydrogen or $R^3$=$R^4$=hydroxy or $R^3$=hydrogen and $R^4$=oxybenzyl or $R^3$=hydrogen and $R^4$=oxy(C$_1$–C$_6$ alkyl).

Other suitable inhibitors are of the formula:

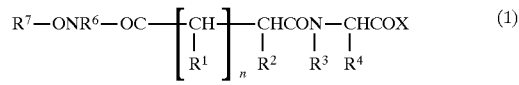
(1)

or

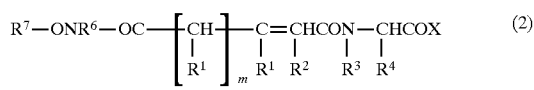
(2)

wherein each $R^1$ is independently H or alkyl(1–8C) and $R^2$ is H or alkyl(1–8C) or —NHZ wherein Z is —R$^{11}$, —COR$^{11}$, or —COOR$^{11}$ where $R^{11}$ is an alkyl(1–6) group; or wherein the proximal $R^1$ and $R^2$ taken together are —(CH$_2$)$_p$— wherein p=3–5;

$R^3$ is H or alkyl(1–4C);

$R^4$ is fused or conjugated unsubstituted or substituted bicycloaryl methylene;

n is 0, 1 or 2; m is 0 or 1; and

X is —OR$^5$, —NHR$^5$, —M or —NH(CH$_2$)$_q$M; wherein $R^5$ is H or substituted or unsubstituted alkyl(1–12C), aryl(6–12C), aryl alkyl(6–16C);

M is an amino acid residue or amide thereof or the residue of a cyclic amine or heterocyclic amine;

q is an integer of from 1–8; and $R^6$ is H or lower alkyl(1–4C) and $R^7$ is H, lower alkyl (1–4C) or an acyl group, and wherein the —$CONR^3$— amide bond shown is optionally replaced by a modified isosteric bond, such as —$CH_2NR^3$—, —$CH_2CHR^3$—, —$CH=CR^3$—, —$COCHR^3$—, —$CHOHCHR^3$—, —$NR^3CO$—, —$CF=CR^3$—, and the like.

Other compounds of the invention include compounds of the formulas

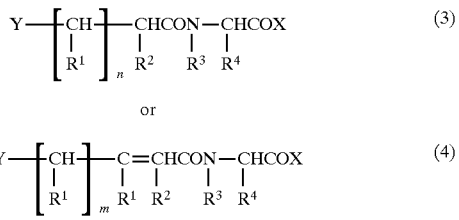

wherein each $R^1$ is independently H or alkyl(1–8C) and $R^2$ is H or alkyl(1–8C) or —NHZ wherein Z is —$R^{11}$, —$COR^{11}$ or —$COOR^{11}$ where $R^{11}$ is an alkyl(1–6C) group; or wherein the proximal $R^1$ and $R^2$ taken together are —$(CH_2)_p$— wherein p=3–5;

$R^3$ is H or alkyl(1–4C);

$R^4$ is fused or conjugated unsubstituted or substituted bicycloaryl methylene;

n is 0, 1 or 2; m is 0 or 1; and

X is —$OR^5$, —$NHR^5$, —M or —$NH(CH_2)_qM$; wherein $R^5$ is H or substituted or unsubstituted alkyl(1–12C), aryl(6–12C), aryl alkyl(6–16C);

M is an amino acid residue or amide thereof or the residue of a cyclic amine or heterocyclic amine;

q is an integer of from 1–8; and

Y is selected from the group consisting of $R^7ONR^6CONR^6$—, $R^6{}_2NCONR^7$—, and $R^6CONOR^7$— or —$COOR^{12}$, wherein each $R^6$ is independently H or lower alkyl(1–4C); $R^7$ is H, lower alkyl(1–4C) or an acyl group, and $R^{12}$ is H, alkyl (1–6C) or —$CH_2$—O-acyl group, and wherein the —$CONR^3$— amide bond shown is optionally replaced by a modified isosteric bond, such as —$CH_2NR^3$—, —$CH_2CHR^3$—, —$CH=CR^3$—, —$COCHR^3$—, —$CHOHCHR^3$—, —$NR^3CO$—, —$CF=CR^3$—, and the like.

Other compounds of the invention include compounds of the formula

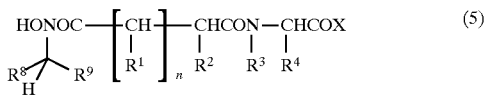

wherein each $R^1$ is independently H or alkyl(1–8C), aryl alkyl(1–4C) or aryl-S-alkyl(1–4C) and $R^2$ is H or alkyl (1–8C), alkenyl(2–6C), aryl alkyl(1–6C) or —NHZ wherein Z is —$R^{11}$, —$COR^{11}$ or —$COOR^{11}$ where $R^{11}$ is an alkyl group;

or wherein the proximal $R^1$ and $R^2$ taken together are —$(CH_2)_p$— wherein p=3–5;

n is 0, 1 or 2;

$R^3$ is H or alkyl(1–4C);

$R^4$ is fused or conjugated unsubstituted or substituted bicycloaryl methylene, unsubstituted or substituted aryl methylene, alkyl(1–12C);

X is —$OR^5$, —$NHR^5$, —M or —$NH(CH_2)_qM$; wherein $R^5$ is H or substituted or unsubstituted alkyl(1–12C), aryl(6–12C), aryl alkyl(6–16C);

M is an amino acid residue or amide thereof or the residue of a cyclic amine or heterocyclic amine;

q is an integer of from 1–8; and $R^8$ is H or $CH_3$;

$R^9$ is optionally substituted aryl, aryl alkyl(1–6C), substituted or unsubstituted alkyl(1–12C), —O-alkyl (1–6C), —S-alkyl(1–6C), —$OCOR^{10}$, —$OCOOR^{10}$, 5-methyl-2-oxo-1,3-dioxol-4-yl, —COOH, —$COOR^{10}$, —$CONH_2$; and $R^{10}$ is alkyl(1–12C).

A prodrug is defined as a chemically protected compound which is substantially biologically inactive, and wherein the biologically active form of the compound is released within the body of a patient preferably as a result of hydrolysis by enzymes such as esterases.

"Alkyl" has its conventional meaning as a straight chain, branched chain or cyclic saturated hydrocarbyl residue such as methyl, ethyl, isobutyl (i-Bu), cyclohexyl, t-butyl (t-Bu) or the like. The alkyl substituents of the invention are of the number of carbons noted which may be substituted with 1 or 2 substituents. Substituents are generally those which do not interfere with the activity of the compound, including hydroxyl, CBZO—, CBZNH—, amino, and the like. Aryl refers to aromatic ring systems such as phenyl, naphthyl, pyridyl, quinolyl, indolyl, and the like; aryl alkyl refers to aryl residues linked to the position indicated through an alkyl residue. In all cases the aryl portion may be substituted or unsubstituted. "Acyl" refers to a substituent of the formula RCO— wherein R is alkyl or arylalkyl as above-defined. The number of carbons in the acyl group is generally 1–15; however as the acyl substituent is readily hydroylsed in vivo the nature of the group is relatively unimportant. "Cyclic amines" refer to those amines where the nitrogen is part of a heterocyclic ring, such as piperidine, "heterocyclic amines" refer to such heterocycles which contain an additional heteroatom, such as morpholine. Bn refers to a benzyl group ($CH_2Ph$), Piv refers to a pivalyl group (CO-t-Bu), Φ refers to a phenyl group.

In the compounds of formulas 1 and 3, preferred embodiments for $R^1$ and $R^2$ include those wherein each $R^1$ is H or methyl and $R^2$ is alkyl of 3–8C, especially isobutyl, 2-methyl butyl, or isopropyl. Especially preferred is isobutyl. Preferred also are those compounds of all of formulas 1–4, wherein n=1 or m=1.

In all of formulas 1–4, preferred embodiments of $R^3$ are H and methyl, especially H.

$R^4$ is a fused or conjugated bicyclo aromatic system linked through a methylene group to the molecule. By "fused or conjugated bicyclo aromatic system" is meant a two-ringed system with aromatic character which may, further, contain one or more heteroatoms such as S, N, or O. When a heteroatom such as N is included, the system as it forms a part of formulas 1–4, may contain an acyl protecting group (1–5C) attached to the nitrogen. Representative bicyclo fused aromatic systems include naphthyl, indolyl, quinolinyl, and isoquinolinyl. Representative conjugated systems include biphenyl, 4-phenylpyrimidyl, 3-phenylpyridyl and the like. In all cases, any available position of the fused or conjugated bicyclic system can be used for attachment through the methylene. The fused or conjugated aromatic system may further be substituted by 1–2 alkyl(1–4C) residues and/or hydroxy or any ring nitrogens may be acylated. Preferred acylation is acetylation.

Preferred embodiments of $R^4$ include 1-(2-methyl naphthyl)methylene; 1-quinolyl methylene; 1-naphthyl methylene; 2-naphthyl methylene; 1-isoquinolyl methylene; 3-isoquinolyl methylene; 3-thionaphthenyl methylene; 3-cumaronyl methylene; 3-(5-methylindolyl)methylene; 3-(5-hydroxyindolyl)methylene; 3-(2-hydroxyindolyl) methylene; biphenyl methylene; and 4-phenylpyrimidyl methylene; and the substituted forms thereof.

Many of these substituents as part of an amino acid residue are described in Greenstein and Winitz, "Chemistry of the Amino Acids" (1961) 3:2731–2741 (John Wiley & Sons, New York).

A particularly preferred embodiment of $R^4$ is 3-indolylmethylene or its N-acylated derivative—i.e., that embodiment wherein the "C-terminal" amino acid is a tryptophan residue or a protected form thereof. A preferred configuration at the carbon to which $R^4$ is bound is that corresponding to L-tryptophan.

Preferred embodiments of X are those of the formula $NHR^5$ wherein $R^5$ is H, substituted or unsubstituted alkyl (1–12C) or aryl alkyl(6–12C). Particularly preferred substitutions on $R^5$ are a hydroxyl group, or a phenylmethoxycarbamyl (CBZNH—) residue. In addition, the compound may be extended by embodiments wherein X is an additional amino acid residue, particularly a glycyl residue, which may also be amidated as described.

In general, the compounds that are hydroxamates are obtained by converting a carboxylic acid or ester precursor of the formulas

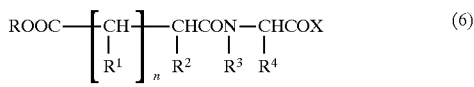
(6)

(7)

wherein R is H or alkyl(1–6C), to the corresponding hydroxamates by treating these compounds or their activated forms with hydroxylamine under conditions which effect the conversion.

With respect to starting materials, the components forming the $-NR^3-CHR^4COX$ moiety are readily available in the case of tryptophan and its analogs as esters or amides. As set forth above, many analogous fused bicyclo aromatic amino acids are described by Greenstein and Winitz (supra). Amino acids corresponding to those wherein $R^4$ is 1-(2-methyl naphthyl)methylene; 1-quinolyl-methylene; 1-naphthyl methylene; 1-isoquinolyl methylene; and 3-isoquinolyl methylene can be prepared from the bicyclo aromatic methylene halides using the acetamido malonic ester synthesis of amino acids, as is well understood in the art. The methylene halides themselves can be prepared from their corresponding carboxylic acids by reduction with lithium aluminum hydride and bromination of the resulting alcohol with thionyl bromide.

In general, the hydroxylamine reagent is formed in situ by mixing the hydroxylamine hydrochloride salt with an excess of KOH in methanol and removing the precipitated potassium chloride by filtration. The filtrate is then stirred with the precursor activated carboxylic acid or ester of formula 6 or 7 for several hours at room temperature, and the mixture is then evaporated to dryness under reduced pressure. The residue is acidified, then extracted with a suitable organic solvent such as ethyl acetate, the extract washed with aqueous potassium bisulfate and salt, and then dried with a solid drying agent such as anhydrous magnesium sulfate. The extract is then again evaporated to dryness and crystallized.

The substituted forms of the hydroxamate which include $-NHOR^7$ are synthesized in an analogous manner but substituting $H_2NOR^7$, wherein $R^7$ is lower alkyl or acyl (1–4C) for hydroxylamine per se. The resulting O-alkyl or acyl hydroxamate can then be further alkylated, if desired, to obtain the $R^7ONR^6-$ derivative of the carboxylic acid. Similarly, $HNR^6OH$ may be reacted with the carboxylic acid to obtain the $HONR^6-$ derivative. $CH_3NHOH$ and $H_2NOCH_3$ are commercially available.

To prepare the starting materials of formulas 6 and 7, the monoesterified carboxylic acid of the formula

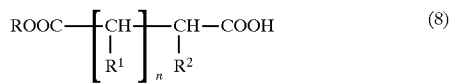
(8)

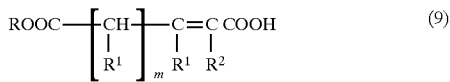
(9)

is reacted with the amino acid of the formula

wherein X is other than OH under conditions wherein the condensation to form the amide bond occurs. Such conditions typically comprise mixture of the two components in a nonaqueous anhydrous polar aprotic solvent in the presence of base and a condensing agent such as a carbodiimide. Thus, the formation of the amide linkage can be catalyzed in the presence of standard dehydration agents such as the carbodiimides, for example dicyclohexyl carbodiimide, or N,N-carbonyl diimidazole. The product is then recovered as a mixture of diastereomers of formula 6 or 7. This mixture is preferably used for the conversion to the hydroxamate and one of the resulting diastereomers is crystallized directly from the product mixture. Alternatively, the diastereomers are separated by flash chromatography before conversion to the hydroxamate and recovered separately. This process is less preferred as compared to the process wherein separation of the diastereomers is reserved until the final product is obtained.

In the notation used in the examples, the "A" isomer is defined as that which migrates faster on TLC; the "B" isomer as that which migrates more slowly. When the "L" form of tryptophan or other amino acid containing a fused bicycloaromatic ring system is used as the residue, and $R^1$ is H, in general, the "A" form is that which contains the corresponding configuration at the carbon containing the $R^2$ substituent in the final hydroxamate product. However, in Example 2, below, where D-tryptophan is included in the composition, the "B" isomer contains what would correspond to an "L" configuration at the carbon containing $R^2$ in the compounds of formula 1.

When $R^6$ and/or $R^7$=alkyl, the corresponding O- or N-alkyl hydroxylamine is reacted with the methyl ester 4A as performed for unsubstituted hydroxylamine in Example 1. Alternatively, the methyl ester 4A can be saponified to its corresponding carboxylic acid and activated with oxalyl chloride or other condensing agent. The alkyl hydroxylamine can then be reacted with the activated carboxylic acid to give the O- or N-substituted hydroxamic acid. O- and N-methylhydroxylamine can be purchased from the Aldrich Chemical Company.

Other N-alkyl hydroxylamines can be synthesized by conversion of aliphatic aldehydes to their oximes, followed by reduction to the N-alkyl hydroxylamine with borane-pyridine complex in the presence of 6N HCl (Kawase, M. and Kikugawa, Y. J., *Chem Soc. Perkin Trans* (1979) 1:643. Other O-alkyl hydroxylamines can be synthesized by the general methods given by Roberts, J. S., "Derivatives of Hydroxylamine," Chapter 6.4 in Barton, D., et al., eds., *Comprehensive Organic Chemistry* (1979) 2:187–188 (Pergamon Press, Oxford). The two general methods employed are displacement by $R^7O-$ of a leaving group from hydroxylamine sulfonic acid or chloramine, and O-alkylation of a hydroxamic acid with $R^7$-X followed by hydrolysis:

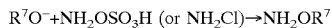

or

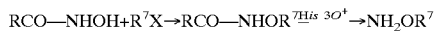

For $R^7$=acyl, a hydroxamic acid of this invention can be acylated with an acid chloride, anhydride, or other acylating agent to give the compounds of this class.

In some cases the derivatized maleic and succinic acid residues required for synthesis of the invention compounds are commercially available. If not, these can readily be prepared, in embodiments wherein $R^1$ is H or alkyl(1–8C) by reaction of a 2-oxocarboxylic ester of the formula $R^2COCOOR'$ in a Wittig reaction with an alkyl triphenylphosphoranylidene acetate or α-triphenylphosphoranylidene alkanoate. The methyl acetate or alkanoate is preferred, but any suitable ester can be employed. This reaction is conducted in a nonaqueous, nonpolar solvent usually at room temperature. The resultant compound is of the formula $ROOCCR^1=CR^2COOR'$, wherein R and R' are residues of esterifying alkyl or arylalkyl alcohols.

If the compounds of formula 7 are desired, this product is condensed with the appropriate tryptophan or analogous derivative; if the compounds of formula 6 are desired, the intermediate is reduced using hydrogen with a suitable catalyst. The sequence of reactions to obtain those embodiments wherein $R^1$ is H or alkyl, n is 1 and m is 0, and $R^2$ is alkyl are shown in Reaction Scheme 1.

Scheme 1

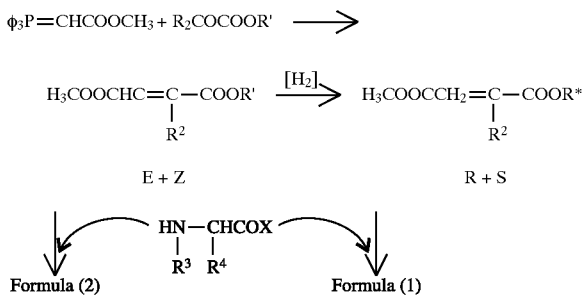

* The hydrogenation reaction will remove R' when R' is benzyl

For those embodiments wherein $R^1$ and $R^2$ taken together are $(CH_2)_p$, the compounds of the invention are prepared analogously to the manner set forth in Reaction Scheme 1, except that the intermediate of the formula $ROOCCHR^1CHR^2COOH$ is prepared from the corresponding 1,2-cycloalkane dicarboxylic acid—i.e., 1,2-cyclopentane dicarboxylic acid anhydride; 1,2-cyclohexane dicarboxylic anhydride or 1,2-cycloheptane dicarboxylic anhydride.

For compounds wherein $-CONR^3-$ is in modified isosteric form, these forms can be prepared by methods known in the art. The following references describe preparation of peptide analogs which include these alternative-linking moieties: Spatola, A. F., *Vega Data* (March 1983), Vol. 1, Issue 3, "Peptide Backbone Modifications" (general review); Spatola, A. F., in "Chemistry and Biochemistry of Amino Acids Peptides and Proteins," (1983) B. Weinstein, eds., Marcel Dekker, New York, p. 267 (general review); Morley, J. S., *Trends Pharm Sci* (1980) pp. 463–468 (general review); Hudson, D., et al., *Int J Pept Prot Res* (1979) 14:177–185 ($-CH_2NR^3-$, $-CH_2CHR^3-$); Spatola, A. F., et al., *Life Sci* (1986) 38:1243–1249 ($-CH_2-S-$); Hann, M. M., *J Chem Soc Perkin Trans I* (1982) 307–314 ($-CH=CR^3-$, cis and trans); Almquist, R. G., et al., *J Med Chem* (1980) 23:1392–1398 ($-COCHR^3-$); Jennings-White, C., et al., *Tetrahedron Lett* (1982) 23:2533 ($-COCHR^3-$); Szelke, M., et al., European application EP 45665 (1982) CA:97:39405 (1982) ($-CH(OH)CHR^3-$); Holladay, M. W., et al., *Tetrahedron Lett* (1983) 24:4401–4404 ($-C(OH)CH_2-$); and Hruby, V. J., *Life Sci* (1982) 31:189–199 ($-CH_2-S-$).

Preferred compounds of formula (1) or (2) include:
HONHCOCH$_2$CH(n-hexyl)-CO-L-Trp-NHMe;
HONHCOCH$_2$CH(n-pentyl)-CO-L-Trp-NHMe;
HONHCOCH$_2$CH(i-pentyl)-CO-L-Trp-NHMe;
HONHCOCH$_2$CH(ethyl)-CO-L-Trp-NHMe;
HONHCOCH$_2$CH(ethyl)-CO-L-Trp-NHCH$_2$CH$_3$;
HONHCOCH$_2$CH(ethyl)-CO-L-Trp-NHCH$_2$CH$_2$OH;
HONHCOCH$_2$CH(ethyl)-CO-L-Trp-NHcyclohexyl;
MeONHCOCH$_2$CH(iBu)-CO-L-Trp-NHEt;
EtONMeCOCH$_2$CH(iBu)-CO-L-Trp-NHEt;
MeONHCOCH$_2$CH(iBu)-CO-L-Ala(2-naphthyl)-NHEt;
EtONMeCOCH$_2$CH(iBu)-CO-L-Ala(2-naphthyl)-NHEt;
HONHCOCH$_2$CH(i-Bu)CO-L-Trp-NHMe;
HONHCOCH$_2$CH(i-Bu)CO-L-N-MeTrp-NHMe;
HONHCOCH$_2$CH(i-Bu)CO-L-Trp-NH(CH$_2$)$_2$OH;
HONHCOCH$_2$CH(i-Bu)CO-L-Trp-NH(S)CHMePh;
HONHCOCH$_2$CH(i-Bu)CO-L-Trp-NH(CH$_2$)$_6$NH—CBZ;
HONHCOCH$_2$CH(i-Bu)CO-L-Ala(2-naphthyl)NHMe;
HONHCOCH$_2$CH(i-Bu)CO-L-Trp-NH(CH$_2$)$_4$CH$_3$;
HONHCOCH$_2$CH(i-Bu)CO-L-Trp-piperidine;
HONHCOCH$_2$CH(i-Bu)CO-L-Trp-NH(CH$_2$)$_{11}$CH$_3$;
HONHCOCH$_2$CH(i-Bu)CO-L-Trp-NHcyclohexyl;
HONHCOCH$_2$CH(i-Bu)-L-Trp-OH;
HONMeCOCH$_2$CH(i-Bu)CO-L-Trp-NHMe;
HONEtCOCH$_2$CH(i-Bu)CO-L-Trp-NHMe;
CH$_3$COONHCOCH$_2$CH(i-Bu)CO-L-Trp-NHMe;
ΦCOONHCOCH$_2$CH(i-Bu)CO-L-Trp-NHMe;
CH$_3$COONMeCOCH$_2$CH(i-Bu)CO-L-Trp-NHMe; and
ΦOCOONEtCOCH$_2$CH(i-Bu)CO-L-Trp-NHMe.

The reverse hydroxamates and hydroxyureas of formulas 3 and 4 are more stable biologically than the corresponding hydroxamates per se. This has been confirmed in Carter, G. W., et al., *J Pharmacol Exp Ther* (1991) 256:929–937; Jackson, W. P., et al., *J Med Chem* (1988) 31:499–500; Young, P. R., et al., *FASEB J* (1991) 5:A1273; Hahn, R. A., et al., *J Pharmacol Ex Ther* (1991) 256:94–102; Tramposch, K. M., et al., *Agents Actions* (1990) 30:443–450; Argentieri, D. C., et al.; Kimball, E., et al., *5th Int Conf Inflammation Research Assoc.*, Whitehaven, Pa., Sep. 23–27, 1990, Abstract 100; and Huang, F., et al., *J Med Chem* (1989) 32:1836–1842. Thus, while somewhat more complicated to synthesize, these analogs offer physiological characteristics which are advantageous in the applications of these compounds to therapy.

The reverse hydroxamates and hydroxyureas of the invention are obtainable using the standard techniques of synthetic organic chemistry (see Challis, B. C., et al., "Amides and Related Compounds" in "Comprehensive Organic Chemistry," Barton, D., et al., eds. (1979) 2:1036–1045), Pergamon Press, Oxford, as further described below.

With respect to starting materials, the components forming the $-NR^3-CHR^4COX$ moiety are readily available in the case of tryptophan and its analogs as esters or amides. As set forth above, many analogous fused bicyclo aromatic amino acids are described by Greenstein and Winitz (supra). Amino acids corresponding to those wherein $R^4$ is 1-(2-methyl naphthyl)methylene; 1-quinolyl-methylene; 1-naphthyl methylene; 1-isoquinolyl methylene; and 3-isoquinolyl methylene can be prepared from the bicyclo aromatic methylene halides using the acetamido malonic ester synthesis of amino acids, as is well understood in the art. The methylene halides themselves can be prepared from their corresponding carboxylic acids by reduction with lithium aluminum hydride and bromination of the resulting alcohol with thionyl bromide.

Depending on the functional group symbolized by Y, the stage of synthesis at which this moiety is brought into the compound of the invention varies.

For those embodiments wherein Y is $R^7ONR^6CONR^6$— and wherein n=0, 1 or 2, the compounds are prepared by acylating an α, β or γ amino acid, respectively with methyl or ethyl chloroformate, condensing the resulting amino acid with a protected form of the moiety —$NR^3CHR^4COX$ and reacting the resulting carboethoxy "dipeptide" with hydroxylamine or a substituted hydroxylamine as described by Fieser, L. F., et al., "Reagents for Organic Synthesis" (1967) 1:479 (John Wiley & Sons, New York). This sequence of reactions is shown in Reaction Scheme 1A.

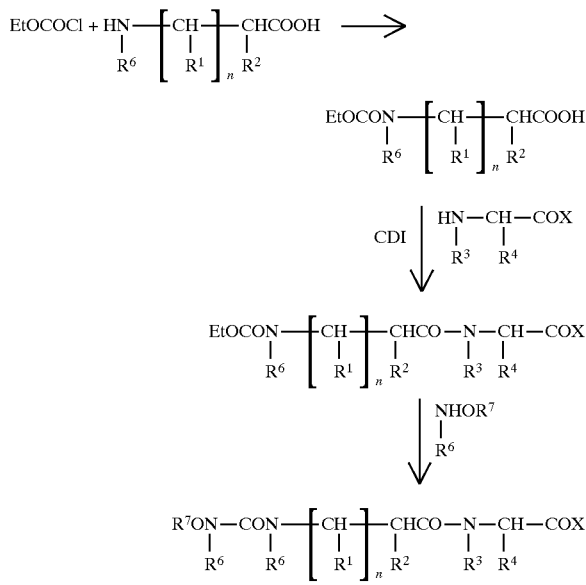

Alternatively, the α, β or γ amino acid is temporarily protected using, for example, carbobenzoxy or tertiary butyloxycarbonyl and coupling it to the carboxy-terminal-protected amino acid moiety containing $R^4$. The protecting group is then removed by hydrogenolysis or acidolysis as appropriate, and the deprotected α, β or γ amino group is reacted with an activated carbonic acid such as carbonyldiimidazole. The resultant is then reacted with hydroxylamine or substituted hydroxylamine to obtain the desired product. This sequence of reactions is summarized in Reaction Scheme 2. (In the formula Im-Co-Im, Im represents an imidazole residue.)

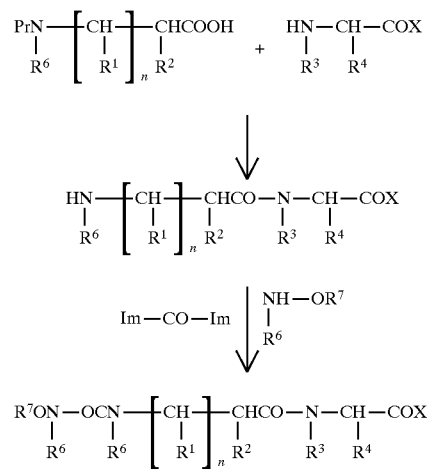

The appropriate α, β or γ amino acids are prepared by general methods as set forth by Jones, J. H., et al., in "Amino Acids," p. 834 (Barton, D., et al., eds.) ("Comprehensive Organic Chemistry" (1979) Vol. 2, Pergamon Press). Such methods include, for example, homologation by Arndt-Eistert synthesis of the corresponding N-protected α-amino acid and more generally the addition of nitrogen nucleophiles such as phthalimide to α,β-unsaturated esters, acids or nitriles.

In a second class of hydroxyureas, Y has the formula $R^6_2NCONOR^7$— and n is 0, 1 or 2. These compounds are prepared from the corresponding α, β or γ hydroxyamino acids of the formula $R^7ONH(CHR^1)_nCHR^2COOH$. When both $R^6$ are H, this intermediate is converted to the desired hydroxyurea by reaction with silicon tetraisocyanate, as described by Fieser and Fieser, "Reagents for Organic Synthesis" (1968) 1:479 (John Wiley & Sons, New York). The reaction is conducted with the hydroxyl group protected or substituted by $R^7$. The resulting hydroxyurea is then coupled to the component of the formula $HNR^3CHR^4COX$ to obtain the desired product. Alternatively, the amide is first formed and the N-hydroxyl dipeptide is treated with the reagent.

Alternatively, when Y is $R^6HNCO$—$NOR^7$, wherein $R^6$ is alkyl, the above O-protected α, β or γ N-hydroxyamino acid is reacted with the relevant alkylisocyanate $R^6NCO$ to produce the desired product.

When Y is of the formula $R^6_2NCO$—$NOR^7$— wherein both $R^6$ are alkyl, the α, β or γ N-hydroxyamino acid is reacted with an activated form of carbonic acid, for example, carbonyl-diimidazole or bis-p-nitrophenylcarbonate, and then with the diamine $R^6_2NH$ wherein both $R^6$ are alkyl groups. This is followed by deprotection, if desired.

Conditions for the foregoing can be found in the descriptions of analogous preparations for tripeptides as described by Nishino, N., et al., Biochemistry (1979) 18:4340–4346.

The β-N-hydroxyamino acids used as intermediates in the foregoing synthesis can be prepared by a malonic ester synthesis in which diethyl malonate is alkylated twice, one with $R^2$—Br and then with benzylchloromethyl ether, for example, for the case wherein $R^1$ is H. The product is saponified, decarboxylated, hydrogenated, and oxidized to give the β-aldehyde in a manner similar to the synthesis of a homologous aldehyde described by Kortylewicz, Z. P., et al., Biochemistry (1984) 23:2083–2087. The desired β-hydroxyamino acid is then obtained by addition of protected (or alkylated, if $R^7$ is alkyl or acylated if $R^7$ is acyl)hydroxylamine. The corresponding compound wherein $R^1$ is alkyl can be prepared in an analogous manner wherein the second alkylation utilizes benzyl-O—$CHR^1Cl$. The homologous ketone was described by Galardy, R. E., et al., *Biochemistry* (1985) 24:7607–7612.

Finally, those compounds wherein Y is of the formula $R^6CONR^7$—, i.e., the reverse hydroxymates, can be prepared by acylation of the corresponding α, β or γ N-hydroxy dipeptide. Alternatively, the N-hydroxyamino acid can be acylated, followed by condensation to form the amide bond in the compounds of the invention. The acylation method is described by, for example, Nishino, N., et al., *Biochemistry* (1979) 18:4340–4346, cited above.

Alternatively, for those compounds wherein n=1 and $R^1$ is H, the compounds can be prepared by condensing the ylide 1,1-dimethoxy-2-(triphenylphosphoranylidene)ethane prepared from triphenylphosphine and 1,1-dimethoxy-2-bromoethane with 4-methyl-2-oxopentanoic acid. The product is then hydrogenated to obtain 4,4-dimethoxy-2-isobutylbutanoic acid which is coupled to the moiety $R^3NHCHR^4COX$ to obtain 4,4-dimethoxy-2-isobutylbutanoyl-$NR^3CHR^4COX$. Treatment with aqueous acid yields the aldehyde 2-isobutyl-4-oxobutanoyl-$NR^3CHR^4COX$. The oxime is prepared by reaction with hydroxylamine and reduced to the corresponding N-substituted hydroxylamine. Acylation of both the hydroxaminol oxygen and nitrogen followed by hydrolysis of the O-acyl group provides the N-acyl reverse hydroxymates. (Summers, J. B., et al., *J Med Chem* (1988) 31:1960–1964.)

For compounds wherein —$CONR^3$— is in modified isosteric form, these forms can be prepared by methods known in the art, as set forth above. Preferred compounds of formulas (3) and (4) include:

EtONHCONMe-CH$_2$CH(iBu)-CO-L-Trp-NHEt;
EtCONOH-CH$_2$CH(iBu)-CO-L-Trp-NHEt;
n-PrCONOEt-CH$_2$CH(iBu)-CO-L-Trp-NHEt;
EtNHCONOMe-CH$_2$CH(iBu)-CO-L-Trp-NHEt;
MeNHCONOH-CH$_2$CH(iBu)-CO-L-Trp-NHEt;
EtONHCONMe-CH$_2$CH(iBu)-CO-L-Ala(2-naphthyl)-NHEt;
EtCONOH-CH$_2$CH(iBu)-CO-L-Ala(2-naphthyl)-NHEt;
n-PrCONOEt-CH$_2$CH(iBu)-CO-L-Ala(2-naphthyl)-NHEt;
EtNHCONOMe-CH$_2$CH(iBu)-CO-L-Ala(2-naphthyl)-NHEt;
MeNHCONOH-CH$_2$CH(iBu)-CO-L-Ala(2-naphthyl)-NHEt;
HONHCONHCH$_2$CH(iBu)-CO-L-TrpNHMe;
HONHCONHCH$_2$CH$_2$CH(iBu)-CO-L-TrpNHMe;
HONHCONHCH(iBu)CO-L-TrpNHMe;
H$_2$NCON(OH)CH(iBu)CO-L-TrpNHMe;
HN(OH)CH$_2$CH(iBu)CO-L-TrpNHMe;
H$_2$NCON(OH)CH$_2$CH$_2$CH(iBu)CO-L-TrpNHMe;
CH$_3$CON(OH)CH(iBu)CO-L-TrpNHMe;
CH$_3$CON(OH)CH$_2$CH(iBu)CO-L-TrpNHMe; and
CH$_3$CON(OH)CH$_2$CH$_2$CH(iBu)CO-L-TrpNHMe.

Administration and Use

As set forth in the Background section above, a number of diseases are known to be mediated by excess or undesired matrix-destroying metalloprotease activity. Thus the compounds of the invention can be applied to treat or prevent such diseases. These include tumor metastasis, rheumatoid arthritis, skin inflammation, ulcerations, particularly of the cornea or mouth, reaction to infection, and the like. Also intended to come within the definition of diseases that can be treated by the invention inhibitors are wounds, preferably chronic dermal wounds. The inhibitors of the invention are, however, useful in any ulcerative skin condition, including, for example, decubitus ulcers, ulcers of the mouth, or other conditions where wound healing is slow. Thus, the compounds of the invention are useful in therapy with regard to conditions involving this unwanted activity.

The compounds of the instant invention are particularly useful for treating or preventing psoriasis. Psoriasis is a common inflammatory skin disease of uncertain etiology, which is characterized by prominent epidermal hyperplasia, mixed inflammatory infiltrates and vascular alterations. The molecular mechanism(s) responsible for epidermal hyperplasia in psoriasis and other skin disorders remain unresolved. However, various growth factors, cytokines and proto-oncogenes have been implicated in the transduction of growth-promoting signals from the extracellular environment into the epidermal keratinocyte. Current treatment of psoriasis and other hyperproliferative skin disorders includes a variety of topical steroids, keratolytic, systemic chemotherapy and UV-light exposure. However, these available therapies are limited by toxicities as well as tachyphylaxis.

Still another condition responsive to the matrix metalloprotease inhibitors of the invention, particularly collagenase inhibitors, include restenosis following angioplasty. The healthy arterial wall is composted of an outer adventitial layer of fibroblasts, a central medial layer of smooth muscle cells and a luminal intimal layer of endothelial cells. It has been postulated that one cause of restenosis following balloon angioplasty is the production and release of collagenase by smooth muscle cells that causes degradation of the intima (Southgate, K. M. et al (1992) Biochem, J., 288:93–99). This, in turn, facilitates migration of the smooth muscle cells into the intima where they continue to proliferate to form the fibrous plaques that are characteristic of restenosis. Thus, matrix metalloprotease inhibitors of the invention would prevent or inhibit restenosis when administered before or after angioplasty.

Yet another application of the matrix metalloprotease inhibitors of the invention is the treatment or prevention of cancer, particularly metastatic and invasive cancers. Cancer cells migrate from their primary site of origin to remote secondary sites by extravasation into the blood, and subsequent extravasation out of the blood to the target organ. Thus, it would be possible to prevent or eliminate metastasis if extravasation of cancer cells could be controlled. Since a key process in extravasation is the breakdown of the extracellular matrix by enzymes secreted by cancer cells, particularly collagenases, the collagenase inhibitors of the invention have significant applications for the treatment or prevention of cancer.

As mentioned above, the collagenase inhibitors of the invention are useful in any ulcerative skin condition, including, for example, decubitus ulcers, ulcers of the mouth, or other conditions where wound healing is slow. Similar conditions susceptible to treatment by the compounds of the invention include corneal or scleral melting associated with keratomalacia, scleromalacia perforans and connective tissue diseases. An example of the latter is keratoconus which involves thinning and central protuberance of the cornea. Type IV collagenase is thought to be responsible, at least in part, for the disease.

Compounds which are synthetic inhibitors of mammalian metalloproteases are useful to inhibit angiogenesis. These compounds can therefore be formulated into pharmaceutical compositions for use in inhibiting angiogenesis in conditions characterized by an unwanted level of such blood vessel growth.

Still another condition responsive to the matrix metalloprotease inhibitors of the invention, particularly collagenase inhibitors, include treatment of shock, including for example, hypovolemic shock and septic shock. The mechanism of many diseases such as hypovolemic shock are complex and the result of multiple causes. Accordingly, "treating" as used herein indicates a methodology which interferes with one or more causes or events and thereby has a beneficial impact on the individual being treated. It is understood that to "treat" hypovolemic shock includes preventing, delaying or in some way reducing the onset of symptoms without perhaps actually removing the cause for shock completely. Accordingly, treatment with the present invention compositions may extend life and/or improve its quality even though the individual being treated ultimately succumbs to shock.

The invention compositions are also applicable to the prevention of such shock in patients that are at a high risk of developing the disease. For instance, certain conditions carry a high risk of developing hypovolemic shock including hemorrhage, trauma, burns, polyuria, vomiting, and diarrhea. See, *Circulatory Shock*, (1992) 91:7. Thus, a patient hospitalized for one of these conditions may be administered the compositions of the invention to prevent the development of hypovolemic shock. Consequently, while reference throughout the patent application is made to methods of treating hypovolemic shock it will be understood by the skilled practitioner of this art that such terminology encompasses preventing shock as well.

Standard pharmaceutical formulation techniques are used, such as those disclosed in *Remington's Pharmaceutical Sciences*, Mack Publishing Company, Easton, Pa., latest edition.

For indications to be treated systemically, it is preferred that the compounds be injected or administered orally. These conditions include tumor growth and metastasis. The compounds can be formulated for injection using excipients conventional for such purpose such as physiological saline, Hank's solution, Ringer's solution, and the like. Injection can be intravenous, intramuscular, intraperitoneal or subcutaneous. Dosage levels are of the order of 0.1 mg/kg of subject to 100 mg/kg of subject, depending, of course, on the nature of the condition, the nature of the subject, the particular embodiment of the invention compounds chosen, and the nature of the formulation and route of administration.

In addition to administration by injection, the compounds of the invention can also be formulated into compositions for transdermal or transmucosal delivery by including agents which effect penetration of these tissues, such as bile salts, fusidic acid derivatives, cholic acid, and the like. The compounds can also be used in liposome-based delivery systems and in formulations for topical and oral administration depending on the nature of the condition to be treated. Oral administration is especially advantageous for those compounds wherein the moiety —CONR³— is in a modified isosteric form or for prodrug forms. These compounds resist the hydrolytic action of the digestive tract. Oral formulations include syrups, tablets, capsules, and the like, or the compound may be administered in food or juice.

The inhibitors of the invention can be targeted to specific locations where vascularization occurs by using targeting ligands. For example, to focus the compounds to a tumor, the inhibitor is conjugated to an antibody or fragment thereof which is immunoreactive with a tumor marker as is generally understood in the preparation of immunotoxins in general. The targeting ligand can also be a ligand suitable for a receptor which is present on the tumor. Any targeting ligand which specifically reacts with a marker for the intended target tissue can be used. Methods for coupling the compounds to the targeting ligand are well known and are similar to those described below for coupling to carrier. The conjugates are formulated and administered as described above.

For localized conditions, topical administration is preferred. For example, to treat diabetes-induced retinopathy or neovascular glaucomas, direct application to the affected eye may employ a formulation as eyedrops or ointment or gel or aerosol. For this treatment, the compounds of the invention can also be formulated as gels or ointments, or can be incorporated into collagen or a hydrophilic polymer shield. The materials can also be inserted as a contact lens or reservoir or as a subconjunctival formulation.

In all of the foregoing, of course, the compounds of the invention can be administered alone or as mixtures, and the compositions may further include additional drugs or excipients as appropriate for the indication.

Conditions that benefit from angiogenesis inhibition thus include, generally, cancer, including angiosarcoma, Kaposi's sarcoma, glioblastoma multiforme, hemangioblastoma, including von Hippel-Lindan disease and hemangiopericytoma; eye conditions, such as diabetic retinopathy and neovascular glaucoma; immune system conditions, such as rheumatoid arthritis, angiolymphoid hyperplasia with eosinophilia; and skin conditions, such as cavernous hemangioma (including Kasabach-Merritt syndrome) and psoriasis.

The following examples are intended to illustrate but not to limit the invention. These examples describe the preparation of certain compounds of the invention and their activity in inhibiting mammalian metalloproteases.

In the examples below, TLC solvent systems are as follows: (A) ethyl acetate/methanol (95:5); (B) ethyl acetate/methanol (25:5); (C) ethyl acetate; (D) ethyl acetate/methanol (30:5); (E) ethyl acetate/hexane (1:1); (F) chloroform/methanol/acetic acid (30:6:2); (G) chloroform/methanol/acetic acid (85:10:1).

EXAMPLE 1

Preparation of N-[D,L-2-isobutyl-3-(N'-hydroxycarbonylamido)propanoyl]-tryptophan methylamide A suspension of 5 g (0.033 mol) of the sodium salt of 4-methyl-2-oxopentanoic acid and 5.65 g (0.033 mol) of benzyl bromide in 10 ml of anhydrous dimethylformamide was stirred for 4 days at room temperature. After evaporation of the solvent under reduced pressure the residue was diluted to 100 ml with hexane and washed with water (3×20 ml) and saturated sodium chloride and dried over anhydrous magnesium sulfate. Evaporation of solvent gave 6.4 g (88% yield) of the benzyl ester of 4-methyl-2-oxopentanoic acid (1) as a colorless oil.

A mixture of 6.4 g (0.029 mol) of (1) and 9.7 g (0.029 mol) of methyl(triphenylphosphoranylidene)acetate in 100 mL of dry methylene chloride was stirred for 12 hr at room temperature and evaporated to dryness. The residue was extracted with hexane (3×50 mL). The hexane solution was washed with 10% sodium bicarbonate (2×30 mL), water and saturated sodium chloride and dried over anhydrous magnesium sulfate. Evaporation of the solvent gave 8.01 g (100% yield) of benzyl 2-isobutyl-3-(methoxycarbonyl)-propionate (2) as a mixture of E and Z isomers.

A mixture of 8.01 g (0.029 mol) of (2) and 1 g of 10% palladium on carbon in 50 mL of methanol was hydrogenated at room temperature under 4 atmospheres of hydrogen gas for 8 hr. After removal of the catalyst by filtration the filtrate was evaporated to dryness under reduced pressure to give 4.7 g (86% yield) of 2-isobutyl-3-(methoxycarbonyl)-propionic acid (3) as a colorless oil.

To a mixture of 0.85 g (4.5 mmol) of (3) and 0.57 g (4.5 mmol) of oxalyl chloride in 10 mL of dry methylene chloride 0.1 mL of anhydrous dimethylformamide was added. After stirring for 1 hr at room temperature the solvent was evaporated under reduced pressure and the residue was diluted to 5 mL with anhydrous dimethylformamide and 1.06 g (4.1 mmol) of the hydrochloride salt of L-tryptophan methylamide (Kortylewicz and Galardy, *J Med Chem* (1990) 33:263–273) was added followed by addition of 1.3 mL (9.3 mmol) of triethylamine at −10° C. This was stirred for 7 hr at room temperature and evaporated to dryness at room temperature under reduced pressure. The residue was diluted to 150 mL with ethyl acetate and washed with water (2×15 mL), 10% potassium bisulfate (5×20 mL), 10% sodium bicarbonate (2×20 mL), saturated sodium chloride and dried over anhydrous magnesium sulfate and then evaporated to give 1.6 g (83% yield) of N-[D,L-2-isobutyl-3-(methoxycarbonyl)-propanoyl]-L-tryptophan methylamide 4 as a mixture of diastereomers, 4A and 4B.

Isomers 4A and 4B were separated by flash chromatography (silica gel, ethyl acetate).

Isomer 4A: mp=134°–137° C. $R_f(C)$=0.37.

Isomer 4B: mp=156°–158° C. $R_f(C)$=0.2.

Alternatively, the mixture of 4A and 4B was converted directly to its hydroxamate as described below. In this case, 5A was crystallized from the mixture of 5A and 5B.

A warm mixture of 0.22 g (3.96 mmol) of potassium hydroxide in 1 mL of methanol was added to a warm mixture of 0.184 g (2.65 mmol) of the hydrochloride salt of hydroxyl-amine. After cooling in ice under an argon atmosphere the potassium chloride was filtered off and 0.5 g (1.32 mmol) of (4A) was added to the filtrate. The resulting mixture was stirred for 7 hr at room temperature and evaporated to dryness under reduced pressure. The residue was suspended in 100 mL of ethyl acetate and washed with 10 mL of 10% potassium bisulfate, saturated sodium chloride and dried over anhydrous magnesium sulfate and evaporated to dryness under reduced pressure. The residue was crystallized from ethyl acetate to give 0.28 g (56% yield) of pure 5A.

Isomer 4B was converted to its corresponding hydroxamic acid 5B (72% yield) as described for 4A.

Isomer 5A: mp=176°–182° C. $R_f(D)$=0.45.

Isomer 5B: mp=157°–162° C. $R_f(D)$=0.39.

For the case wherein the 4A/4B mixture is used, the 5A can be crystallized directly from the residue as described above.

In a similar manner to that set forth above, but substituting for 4-methyl-2-oxopentanoic acid, 2-oxopentanoic acid, 3-methyl-2-oxobutyric acid, 2-oxohexanoic acid, 5-methyl-2-oxohexanoic acid, or 2-decanoic acid, the corresponding compounds of formula 1 are prepared wherein $R^1$ is H and $R^2$ is an n-propyl, i-propyl, n-butyl, 2-methylbutyl, and n-octyl, respectively. In addition, following the procedures set forth hereinabove in Example 1, but omitting the step of hydrogenating the intermediate obtained by the Wittig reaction, the corresponding compounds of formula 2 wherein $R^1$ is H and $R^2$ is as set forth above are obtained.

To synthesize the compounds containing acylated forms of the indolyl residue, the intermediate ester of formula 3 or 4 is deesterified and acylated prior to conversion to the hydroxamate. For illustration, 4A is deesterified with sodium hydroxide in ethanol and then acidified to give N-(L-2-isobutyl-3-carboxypropanoyl)-L-tryptophan methylamide, which is treated with the anhydride of an alkyl(1–4C) carboxylic acid to obtain N-(L-2-isobutyl-3-carboxypropanoyl)-L-((N-acyl)indolyl)-tryptophan methylamide. This intermediate is then treated with oxalyl chloride followed by hydroxylamine at low temperature to give the corresponding hydroxamate.

EXAMPLE 2

Preparation of N-[2-isobutyl-3-(N'-hydroxycarbonylamido)propanoyl]-D-tryptophan methylamide (7B)

The mixture of the two diastereoisomers of N-[2-isobutyl-3-(methoxycarbonyl)-propanoyl]-D-tryptophan methyl amide 6A,B was prepared as described for 4A,B in Example 1. The mixture was crystallized from ethyl acetate to give, after two recrystallizations, 0.26 g (49%) of the pure diastereomer 6B: mp 155°–157° C., $R_f(C)$=0.32. 6B was converted into its hydroxamic acid 7B by the method described in Example 1 in 50% yield (119 mg): mp 157°–159° C., $R_f(D)$=0.39.

EXAMPLE 3

Preparation of N-[2-isobutyl-3-(N'-hydroxyamidocarbonyl)propanoyl]-N-methyl-L-trypophan methylamide (9A)

The reaction of N-methyl-L-tryptophanmethylamide, prepared as described in Example 1 for L-tryptophan methylamide, with 3 performed as described for 4 gave crude N-[D,L-2-isobutyl-3-(methoxycarbonyl)-propanoyl]-N-methyl-L-tryptophan methylamide 8A,B which was crystallized from ethyl acetate to give 76 mg (19% yield) of 8A: mp 171°–174° C., $R_f(C)$=0.40.

8A was converted into 9A by the method described in Example 1 in 45% yield (34 mg): mp 180°–183° C., $R_f(D)$=0.54.

EXAMPLE 4

Preparation of N-[2-isobutyl-3-(N-hydroxyamidocarbonyl)prolanoyl]-L-3-(2-naphthyl)-alanine methylamide (11A)

N-[D,L-isobutyl-3-(methoxycarbonyl)-propanoyl]-L-3-(2-naphthyl)-alanine 10A was prepared as described in Example 1 from L-3-(2-naphthyl)-alanine methylamide and 3. The crude product was chromatographed on 60 g of silica gel in ethyl acetate:hexane 1:1 to yield 12 mg (5% yield) of 10A: mp 151°–158° C., $R_f(C)$=0.69.

10A was converted into the hydroxamate 11A as in Example 1 in 30% yield (3 mg): mp 179°–181° C., $R_f(D)$ =0.17. MS-FAB (m/z) 400 ($M^+$ +H).

EXAMPLE 5

Preparation of N-[2-isobutyl-3-(N'-hydroxyamidocarbonyl)propanoyl]-L-tryptophan 2-hydroxyethylamide (13A)

The hydrochloride salt of L-tryptophan-2-hydroxyethylamide was prepared and coupled with 3 as described for the hydrochloride salt of L-tryptophan methylamide in Example 1 except that 3 was activated with 1,1'-carbonyldiimidazole for 20 minutes in methylene chloride at room temperature. The crude product was a mixture of 0.7 g (67% yield) of the diastereoisomers 12A,B: $R_f(C)$ 12A 0.38, $R_f(C)$ 12B 0.19.

12A crystallized from ethyl acetate in 35% yield (0.18 g): mp 161°–163° C., $R_f(C)$=0.38.

12A was converted into N-[2-isobutyl-3-(N'-hydroxyamidocarbonyl)propanoyl]-L-tryptophan 2-hydroxyethylamide 13A as in Example 1 in 35% yield (62 mg): $R_f(D)$=0.17, mp 162°–163° C. MS-FAB (m/z) 419 (M$^+$ +H).

EXAMPLE 6

Preparation of N-[2-isobutyl-3-(N'-hydroxyamidocarbonyl)propanoyl]-L-tryptophan amylamide (15A)

The hydrochloride salt of L-tryptophan amylamide was prepared as described in Example 1 for L-tryptophan methylamide and was reacted with 3 that had been activated with 1,1'-carbonyldiimidazole for 20 minutes in dichloromethane at room temperature. The mixture of the two diastereomers of N-[D,L-2-isobutyl-3-(methoxycarbonyl)-propanoyl]-L-tryptophan amylamide 14A,B (90% yield) was converted to its corresponding hydroxamic acids as described for 4A. Slow evaporation of the ethyl acetate solution gave 0.343 g (71%) of 15A,B: mp 160°–163° C. MS-FAB (m/z) 445 (M$^+$ +H).

EXAMPLE 7

Preparation of N-[2-isobutyl-3-(N'-hydroxyamidocarbonyl)propanoyl]-L-tryptophan piperidinamide (17A,B)

L-tryptophan piperidinamide was reacted with 3 as performed in Example 1 for L-tryptophan methylamide to give 1.14 g (89% yield) of N-[D,L-2-isobutyl-3-(methoxycarbonyl)-propanoyl]-L-tryptophan piperidinamide 16A,B as a foam; $R_f(C)$ (16A) 0.74, (16B) 0.67.

16A,B was converted into crude 17A,B identically to 4A in Example 1 in 88% yield (570 mg): $R_f(D)$ (17A) 0.41, (17B) 0.30. Crude 17A,B was chromatographed on 180 g of silica gel in 12% isopropanol in ethyl acetate to give 140 mg (25% yield) of 17A,B after crystallization from ethyl acetate: mp 169°–170° C. MS-FAB (m/z) 443 (M$^+$ +H).

EXAMPLE 8

Preparation of N-[2-isobutyl-3-(N'-hydroxyamidocarbonyl)propanoyl]-L-tryptophan dodecylamide (19A)

The reaction of L-tryptophan dodecylamide was prepared in a manner analogous to that described for L-tryptophan methylamide in Example 1. This ester was reacted with 3 as described in Example 1 to give crude N-[D,L-isobutyl-3-(methoxycarbonyl)-propanol]-L-tryptophan dodecylamide 18A,B in 93% yield as a mixture of isomers 18A and 18B. This mixture was chromatographed on 150 g of silica gel in ethyl acetate:hexane, 1:2, to yield 0.62 g of the mixture of the two isomers: $R_f(E)$ 18A 0.37, $R_f(E)$ 18B 0.29.

Crystallization by slow evaporation from ethyl acetate gave 0.38 g of 18A contaminated by approximately 10% of 18B by TLC and NMR analysis: mp 133°–135° C. 18A was converted to its corresponding hydroxamic acid as described in Example 1, except that the potassium salt of 19A crystallized from the alkaline reaction mixture in 81% yield (222 mg). The potassium salt of 19A (54 mg) was dissolved in 2 mL of boiling methanol, a few drops of water were added, and the solution was acidified to pH 6 with 0.1N hydrochloric acid and diluted with water to give 50 mg (100% yield) of 19A: mp 155°–159° C., $R_f(D)$=0.49. MS-FAB (m/z) 543 (M$^+$ +H).

EXAMPLE 9

Preparation of N-[2-isobutyl-3-(N'-hydroxyamidocarbonyl)propanoyl]-L-tryptophan (S)-methylbenzylamide (21A)

The reaction of L-tryptophan (S)-methylbenzylamide with 3 was performed as described in Example 1 to give, after crystallization from ethyl acetate, 330 mg (51% yield) of N-[2-isobutyl-3-(methoxycarbonyl)-propanoyl]-L-tryptophan (S)-methylbenzylamide 20A: mp 160°–162° C., $R_f(C)$=0.77.

20A was converted into hydroxamate 21A by the identical method used in Example 1 in 38% yield (76 mg): mp 165°–166° C., $R_f(D)$=0.73. MS-FAB (m/z) 479 (M$^+$ +H).

EXAMPLE 10

Preparation of N-[L-2-isobutyl-3-(N'-hydroxyamidocarbonyl)-propanoyl]-L-tryptophan(6-phenyl-methoxycarbonyl-1-aminohexyl)amide (27A)

To prepare 1-amino-6-phenylmethoxycarbonylaminohexane (23), an equimolar mixture (0.01 mol) of 1,6-diaminohexane and benzaldehyde. in 25 mL of methylene chloride was stirred for 5 hr in the presence of 1.5 g of anhydrous magnesium sulfate at room temperature. After removing the drying agent by filtration the filtrate was evaporated to dryness under reduced pressure to give 2 g (100% yield) of crude 1-amino-6-phenylamino-hexane 22 as a colorless oil; NMR(CDCl$_3$) 1.1–1.9 (m, 10H, hexane CH$_2$-2,-3,-4,-5, NH$_2$); 2.6 (m, 2H, CH$_2$-1); 3.51 (m, 2H, hexane CH$_2$-6); 7.1–7.8 (m, 5H, aromatic); 8.16 (s, 1H, imine CH). To a mixture of 2 g (0.01 mol) of 22 and 1.4 mL (0.01 mol) of triethylamine in 20 mL of dichloromethane. Then 1.78 g (0.01 mol) of benzylchloroformate was added dropwise at −5° C. The resulting mixture was stirred for 0.5 hr at 0° C. and for 2 hr at room temperature then diluted to 50 mL with methylene chloride and washed with water (20 ml), 2% sodium bicarbonate (20 ml), water and saturated sodium chloride and dried over anhydrous magnesium sulfate. After evaporation of solvent under reduced pressure the residue was dissolved in 5 mL of ethanol and 10 mL of 2N hydrochloric acid was added. The resulting mixture was stirred for 6 hr at room temperature then evaporated to dryness under reduced pressure. The residue was diluted to 50 mL with water and washed with ethyl ether (2×15 ml). The water phase was evaporated under reduced pressure and the product 23 was purified by crystallization from a small portion of water with a yield of 42%; mp 175°–178° C.

To prepare the dipeptide analog (N-(L-2-isobutyl-3-methoxycarbonyl)propanoyl-L-tryptophan (25A)), for derivatization to 23: To a mixture of 1.754 g (9.32 mmol) of 2-isobutyl-3-methoxycarbonylpropionic acid 3 in 4 mL of 50% anhydrous DMF in methylene chloride 1.66 g (10.2 mmol) of N,N'-carbonyldiimidazole (CDI) was added at room temperature. After 15 minutes of stirring at room temperature, 3.08 g (9.31 mmol) of the hydrochloride salt of L-tryptophan benzyl ester was added. The resulting mixture was stirred overnight at room temperature, then diluted to 60 mL with ethyl acetate and washed with 5% sodium bicarbonate (2×15 ml), water (2×15 ml), saturated sodium chloride solution and dried over magnesium sulfate. Evaporation of the solvent under reduced pressure gave 4.32 g (100% yield) of 24, the benzyl ester of 25 as a colorless foam, which was used in the next step without further purification.

Hydrogen gas was bubbled through a mixture of 4.32 g (9.31 mmol) of 24 and 0.5 g of 10% palladium on carbon in 15 mL of methanol for 2 hr while methanol was added to keep the volume of the reaction mixture constant. The catalyst was filtered off and washed with a fresh portion of methanol (15 ml) and the filtrate was evaporated to dryness under reduced pressure. Evaporation of the solvent under reduced pressure and drying of the residue in vacuo gave 3.08 g (88% yield) of acid 25A,B as a mixture of two diastereoisomers, in the form of a colorless glassy solid. This was separated to give isomers 25A and 25B by flash chromatography (silica gel; ethyl acetate; $R_f$(25A)=0.24, $R_f$(25B)=0.1).

The compound 25A was converted to N-[L-2-isobutyl-3-methoxycarbonylpropanoyl]-L-tryptophan (carbonylaminohexyl)amide (26) as follows. A mixture of 0.55 g (1.47 mmol) of 25A and 0.24 g (1.48 mmol) of CDI in 1 mL of 2% dimethylformamide in methylene chloride was stirred for 0.5 hr at room temperature and 0.42 g (1.47 mmol) of 23 was added. After stirring overnight at room temperature, the mixture was diluted to 50 mL with chloroform and washed with 2% potassium bisulfate (2×10 ml), water (10 ml), 5% sodium bicarbonate (2×10 ml), water (2×10 ml) and saturated sodium chloride and dried over anhydrous magnesium sulfate. Evaporation of the solvent under reduced pressure gave 0.8 g of the crude 26A which was purified by flash chromatography (silica gel; ethyl acetate/hexane 25:5): Yield 56%; $R_f$(E)=0.57.

When the product 26A is substituted for 4A in Example 1, the identical process afforded the title compound 27A, melting at 102°–108° C., in 46% yield; $R_f$(D)=0.63.

EXAMPLE 11

Preparation of N-[L-2-Isobutyl-3-(N'-hydroxyamidocarbonyl)propanoyl]-L-tryptophan cyclohexylamide (28A)

When cyclohexylamine is substituted for 23 in Example 10, the identical process afforded the title compound 28A melting at 199°–203° C., in 49% yield; $R_f$(D)=0.51.

EXAMPLE 12

Preparation of N-[(±)cis-2-(N'-hydroxyamidocarbonyl)cyclohexylcarbonyl]-L-tryptophan methylamide (29A,B)

A mixture of 2 g (0.013 mol) of cis-1,2-cyclohexanedicarboxylic anhydride in 15 mL of methanol was refluxed for 5 hr, then evaporated to dryness under reduced pressure to give 2.41 g (100% yield) of cis-2-methoxycarbonylcyclohexane-carboxylic acid. When this was substituted for 3 in Example 1, the identical process afforded the title compound, melting at 140°–144° C., in 36% yield; $R_f$(D)=0.53, 0.47.

EXAMPLE 13

Preparation of N-[(±)trans-2-(N'-hydroxyamidocarbonyl)-cyclohexylcarbonyl]-L-tryptophan methylamide (30A,B)

When (±)trans-1,2-cyclohexanedicarboxylic anhydride was substituted for cis-1,2-cyclohexanedicarboxylic anhydride in Example 12, the identical process afforded the title compound 30A,B, melting at 167°–174° C., in 37% yield; $R_f$(D)=0.57.

EXAMPLE 14

Preparation of N-[2-Isobutyl-3-(N'-hydroxyamidocarbonyl)propanoyl]-L-tryptophan (31 A)

31A was prepared from 25A in Example 10 in a similar manner to the preparation of 5A in Example 1 in 75% yield (128 mg) and isolated as a foam from ethyl acetate: $R_f$(F) =0.55, MS-FAB (m/z) (M$^+$ +H). A small sample of 31A recrystallized from ethyl acetate had a melting point of 116°–120° C.

EXAMPLE 15

Preparation of N-(D,L-2-Isobutyl-3-carboxypropanoyl)-L- tryptophan(6-aminohexyl-1) amide (32A)

A mixture of 0.5 g (8.24 mmol) of 26A in 0.4 mL of 2N potassium hydroxide in methanol was stirred overnight at room temperature, then evaporated to dryness under reduced pressure. The residue was diluted to 15 mL with water and acidified to pH=2 with 1N hydrochloric acid. The crude free acid of 26A was taken up with ethyl acetate (3×15 ml) and the organic phase was dried over anhydrous magnesium sulfate and evaporated to dryness to give 0.45 g (92% yield) of 26A as a colorless foam.

Hydrogen gas was bubbled through a mixture of 0.395 g (6.6 mmol) of the free acid of 26A in 15 mL of methanol for 2 hr, in the presence of 0.12 g of 10% palladium on carbon at room temperature. The catalyst was filtered off, washed with ethanol (2×20 ml) and the filtrate was evaporated to dryness under reduced pressure to give 0.3 g (92% yield) of the title compound 32A as a colorless foam; $R_f$(G)=0.08.

EXAMPLE 16

Preparation of N-[N-(2-Isobutyl-3-carboxypropanoyl)-L-tryptophanyl]glycine (34A,B)

The reaction of L-tryptophanyl-glycine methyl ester with acid 3, performed as described for 25A gave crude N-[N-(D,L-2-isobutyl-3-methoxycarbonylpropanoyl)-L-tryptophanyl]-glycine methyl ester 33 in 87% yield as a mixture of diastereomers 33A and 33B. Isomers 33A and 33B were separated by flash chromatography (silica gel; ethyl acetate). Isomer 33A mp=154°–155° C.; $R_f$(C)=0.46.

Esters 33A,B were transformed to free acids 34A,B by saponification with two equivalent of methanolic potassium hydroxide, as described for 25A.

Isomer 34A yield 92%; mp=96°–102° C.; $R_f$(G)=0.31.

Isomer 34B yield 93%; mp=99°–105° C.; $R_f$(G)=0.25.

EXAMPLE 17

Preparation of N-[(+)cis-2-carboxy-cyclohexylcarbonyl]-L-tryptophan methylamide (35)

To a mixture of 0.281 g (1.82 mmol) of cis-1,2-cyclohexanedicarboxylic anhydride and 0.47 g of the hydrochloride salt of L-Trp-NHMe in 0.5 mL of dimethylformamide 0.51 mL of triethylamine was added at room temperature. After 2 hr of stirring the resulting mixture was diluted to 10 mL with water and 25 mL of ethyl acetate was added. The resulting mixture was acidified to pH=2 with 10% potassium bisulfate and the organic phase was washed with water (2×15 ml), saturated sodium chloride and dried over anhydrous magnesium sulfate and evaporated to dryness. The title compound 35 was purified by crystallization from an ethyl acetate-hexane mixture. Yield 48%; mp=105°–112° C.; $R_f(G)$=0.65, 0.61.

EXAMPLE 18

Preparation of N-[(+)trans-2-carboxy-cyclohexylcarbonyl]-L-tryptophan methylamide (36)

When (±)trans-1,2-cyclohexanedicarboxylic anhydride is substituted for cis-1,2-cyclohexanedicarboxylic anhydride in Example 17, the identical process afforded the title compound 36 in 56% yield: mp=167°–174° C.; $R_f(G)$=0.67, 0.61.

EXAMPLE 19

Preparation of N-[2-Isobutyl-3-(N'-acetoxycamidocarbonyl)-propanoyl]-L-tryptophan methylamide (37A)

To 97.5 mg (0.25 mmol) of 5A (Example 1) in 0.5 ml of dimethylformamide was added 25.5 mg (0.25 mmol) of acetic anhydride and 37 mg (0.25 mmol) of 1 8-diazabicyclo[5.4.0]-undec-7-ene (DBU) at room temperature. After standing overnight, the DMF was evaporated under high vacuum and the residue taken up in a mixture of equal volumes of ethyl acetate and 2% potassium bisulfate. The ethyl acetate layer was washed with 2% potassium bisulfate, water, and brine, dried over magnesium sulfate, and evaporated to give a solid. The solid was dissolved in a 1:1 mixture of hot ethyl acetate:hexane, which upon standing at room temperature gave 71 mg (66% yield) of solid product 37A: mp=184°–186° C.; $R_f(G)$=0.68.

EXAMPLE 20

Preparation of N-[2-Isobutyl-3-(N'-benzoxyamidocarbonyl)propanoyl]-L-tryptophan methylamide (38A)

To 30.5 mg (0.25 mmol) of benzoic acid in 1 ml of tetrahydrofuran was added 40.5 mg (0.25 mmol) of carbonyl-diimidazole. After 10 minutes, 97 mg (0.25 mmol) of compound 5A from Example 1 was added in 1 ml of dimethylformamide. After 10 minutes, the reaction mixture was evaporated to dryness under high vacuum, and dissolved in a mixture of equal volumes of ethyl acetate and water. The ethyl acetate layer was washed with 5% sodium bicarbonate, water, 2% sodium bisulfate, water, and brine, and dried over magnesium sulfate. Evaporation of the ethyl acetate layer to a small volume gave 50 mg (41%) of the title compound, 38A: mp=187°–187.5° C.; Fr(G)=0.54.

EXAMPLE 21

Preparation of N-(2R-2-Carboxymethyl-4-methylpentanoyl)-L-tryptophan (S)-methylbenzyl amide (39A)

N-tBoc-L-Tryptophan (10.04 g, 32.99 mmole) was dissolved in tetrahydrofuran (100 ml) and carbonyldiimidazole (5.35 g, 32.99 mmole) was added. After stirring for 1 hour at room temperature, (S)-methylbenzylamine (4.25 ml, 32.99 mmole) was added. The reaction was stirred at room temperature for 16 hours after which the solvent was removed and the residue was dissolved in ethyl acetate (100 ml). The resulting mixture was washed with 0.1N HCl (3×60 ml), saturated aqueous sodium bicarbonate (2×50 ml), and brine (2×20 ml). After drying over anhydrous magnesium sulfate, the solution was filtered and concentrated to dryness to give Boc-L-tryptophan (S)-1-phenethyl amide N-tert-butyl carbamate (40, 13.78 g, 100% yield).

The compound 40 (2.00 g, 4.91 mmole) was dissolved in methanol (40 mL) and 6N aqueous hydrochloric acid (20 mL) was added. The reaction was stirred at room temperature for 2 hours and concentrated to dryness to provide L-tryptophan (S)-1-phenethyl amide hydrochloride salt (41, 1.69 g, 95% yield) as a colorless solid.

The compound 41 was coupled with 3A (see Examples 23 and 24 for the synthesis and structure of 3A) in the presence of carbonyl diimidazole as described above to yield N-(2R-2-methoxy-carbonylmethyl-4-methylpentanoyl)-L-tryptophan (S)-methylbenzyl amide (42A).

The compound 42A (10.04 g, 21.05 mmoles) was dissolved in tetrahydrofuran (200 mL), 6N hydrochloric acid (200 mL) was added to the solution and the reaction was stirred at room temperature for 6 hours after which it was washed with chloroform (3×200 mL). The combined organic extracts were washed with 0.1N sodium hydroxide (3×150 mL). The chloroform layer was concentrated to 150 mL and washed again with 0.1N sodium hydroxide (3×50 mL). The combined aqueous extracts were acidified to pH=2 with concentrated hydrochloric acid and washed with ethylacetate (3×50 mL). The combined ethyl acetate extracts were dried over anhydrous magnesium sulfate, filtered, and concentrated to dryness. The residue is recrystallized from ethylacetate (75 mL) to yield N-(2R-carboxymethyl-4-methylpentanoyl)-L-tryptophan (S)-methylbenzyl amide (39A). After filtration and concentration of the mother liquor, a second crop of 39A was obtained by recrystallization from dichloromethane (75 mL) and the combined crops of 39A (3.72 g, 38%) were dried under vacuum.

It is noteworthy that Compound 42A was recovered from the chloroform layer which was dried over anhydrous magnesium sulfate, filtered, and concentrated. The residue was purified on silica gel (50% ethylacetate/hexane) to give recovered 42A (2.48 g, 25%).

EXAMPLE 22

Preparation of N-(2RS-2-Methoxycarbonylmethyl-4-methylpentanoyl)-L-tryptophan (43)

L-Tryptophan (1.22 g, 6.0 mmole) was dissolved in water (5.00 mL) and 6N aqueous sodium hydroxide (0.90 mL). The resulting solution was cooled to 0° C.

D,L-2-Isobutyl-3-(methoxycarbonyl)-propionic acid (3, 0.94 g, 5.0 mmole) was dissolved in dichloromethane (3.00 mL) and oxalyl chloride (0.44 mL, 5.0 mmole) was added. The resulting solution was cooled to 0° C. and added to the L-tryptophan solution over 1 hour. During the addition, the reaction was vigorously stirred and the pH was maintained above 9 by the periodic addition of 100 μl portions of 6N aqueous sodium hydroxide. After the addition, the reaction was stirred at room temperature overnight and subsequently diluted with water and ethyl acetate. After acidifying the reaction to pH 2 with 10% aqueous potassium bisulfite, the aqueous layer was removed and the ethyl acetate layer was washed with 2% potassium bisulfite (2×10 ml), water (2×10 ml), and brine. The organic phase was dried over magnesium sulfate, filtered, and concentrated. Purification of the residue on silica gel (chloroform then chloroform/methanol) gave 3 (0.28 g, 29% recovered yield) and 43 (1.11 g, 60% yield).

It is noteworthy that compound 43 can be converted to 42A by coupling with S-methylbenzylamine and the resultant product can be resolved by crystallizing from ethanol. 39A can be produced from compound 42A by hydrolysis as described above in Example 21.

EXAMPLE 23

Preparation of D,L-2-Isobutyl-3-(Methoxycarbonyl) Propionic Acid (3)

This method describes an improved method for the synthesis of D,L-2-isobutyl-3-(methoxycarbonyl)-propionic acid (3). Maleic anhydride (750 g, 7.65 moles) was dissolved in hot toluene (500 mL), filtered, and allowed to cool thus producing a finely divided crystalline precipitate. The resulting mixture was further cooled in a refrigerator. 2-Methylpropene was condensed into cold toluene (1 L). The cold maleic anhydride suspension was transferred, with the aid of additional toluene (300 mL), to the glass liner of a Parr 2 gallon stirred autoclave. The 2-methylpropene solution was then added followed by 4-tert-butyl catechol (2 g). The autoclave was sealed and heated, with stirring, to 170° C. over 45 minutes and maintained at that temperature for an additional 9.5 hours. The reaction was then allowed to cool to 60° C. over 7 hours after which, the autoclave was vented. After an additional 1.5 hours, the internal temperature had reached 45° C. and the autoclave was opened. The solvent was removed and the residue was distilled under aspirator pressure through a 10 inch vacuum jacketed Vigreux column fitted with a partial take off head to give unreacted maleic anhydride (139.4 g, 18.6% yield) and β-methallylsuccinic anhydride (765.3 g, 79.8% yield).

β-Methallylsuccinic anhydride (539 g, 3.50 mole) was dissolved in toluene (800 mL) in a 1700 mL Parr stainless steel bottle fitted with a heating jacket. 10% Pd/C (3.60 g) was added and the bottle was connected to a Parr 2 L shaker fitted with two 4 L hydrogen tanks. After several evacuations and refilling with hydrogen, the shaker was started with the heater controlled for 60° C. The initial pressure was 60 lbs. When the pressure fell to 10 lbs, the tanks were repressurized to 60 lbs. After two hours, the controller was reset to 70° C. and the reaction was continued for another 12 hours. The heat was then turned off and after another 5 hours, the shaker was stopped. The reaction vessel was evacuated and the reaction mixture was filtered and concentrated. Distillation of the residue through the Vigreux column described above (P=9–10 mm Hg, T=180° C.) gave isobutylsuccinic anhydride (532.9 g, 97.6% yield).

Isobutylsuccinic anhydride (501 g, 3.21 mole) was dissolved in anhydrous methanol (500 mL) and allowed to stand at room temperature for 5 days. The methanol was removed and the residue was mixed with petroleum ether (500 mL) and refrigerated overnight. The solids were filtered and the filtrate was put in a freezer. After prolonged storage, the solids were filtered and the combined solids were recrystallized from petroleum ether to give the Compound 3 (337.5 g, 55.9% yield).

After concentrating the combined petroleum ether filtrates from above, 188 g (1 mole) of the crude material [mostly consisting of (R,S)3-methoxycarbonyl-5-methylhexanoic acid] was mixed with sodium hydroxide (120 g, 3 moles) and water (700 mL). The mixture was stirred on a steam bath for 14 hours. The mixture was filtered and acidified with concentrated sulfuric acid (90 mL) and refrigerated. The suspension of sodium sulfate and the diacid was filtered and the solids were thoroughly washed with ethyl acetate (500 mL). The aqueous solution was washed with ethyl acetate and the combined ethyl acetate phases were concentrated and dried under vacuum to give the diacid (162.8 g, 93.6% yield). The diacid was heated with acetic anhydride (150 mL) under a 10 inch vacuum jacketed Vigreux column. Acetic acid was removed over several hours at 118°–120° C. When the temperature began to fall, the pressure was gradually reduced to remove the excess acetic anhydride. Isobutylsuccinic anhydride (138 g, 88.5% yield) was collected by distillation (P=10 mm Hg, T=144° C.) and recycled back into the final step of this preparation.

EXAMPLE 24

Resolution of (3) to (3A)

D,L-2-Isobutyl-3-(methoxycarbonyl)-propionic acid (3, 17.55 g, 93.35 mmole) was dissolved in diethyl ether (85 mL) and S-methyl benzylamine (13.24 mL, 102.69 mmole) was added. The reaction was stirred at room temperature for 24 hours and the solids were removed by filtration. Recrystallization of the solids from ethanol/diethyl ether gave the salt 44A (9.24 g, 32% mass recovery, 64% yield) as a single diastereomer.

44A (1.29 g, 4.18 mmole) was dissolved in saturated aqueous sodium bicarbonate and washed, three times, with ethyl acetate. The combined ethyl acetate layers were washed with saturated aqueous sodium bicarbonate and the combined aqueous layers were acidified with aqueous 6N hydrochloric acid and washed three times with ethyl acetate. The combined ethyl acetate layers were washed with aqueous saturated sodium chloride, dried over anhydrous magnesium sulfate, filtered and concentrated to give 3A (0.77 g, 98% yield, $[\alpha]_D$=+19.8 deg.).

EXAMPLE 25

Preparation of N-[2R-Isobutyl-3-(N'-hydroxyamidocarbonyl)propanoyl]-L-tryptophan-3 (4-morpholinyl)-n-propylamide (50)

A suspension of t-BOC-tryptophan (6 g) in dichloromethane (20 ml) was mixed with carbonyl diimidazole (3.26 g) and stirred at room temperature for 20 minutes. 4-Morpholinyl-n-propylamine (2.88 ml) was added to this mixture and this was stirred overnight at room temperature, quenched with water (100 ml), and extracted with ethyl acetate (300 ml). The organic layer was washed with brine, dried over sodium sulfate, filtered and concentrated to provide the crude morpholine amide (45).

The compound 45 was dissolved in a solvent mixture containing dichloromethane (30 ml), trifluoroacetic acid (30 ml) and anisole (6 ml), and stirred at room temperature for 2 hours. The solution was mixed with hexane (60 ml) followed by diethylether (120 ml), the supernatent was decanted and the residue was evaporated to dryness to yield the trifluoroacetic acid salt (46).

A solution of 4-(t-butoxy)-2R-isobutylsuccinic acid (0.46 g) (see European Patent Application No. 92301051.8, filed on Jul. 2, 1992) and carbonyl diimidazole (0.32 g) in dichloromethane (3 ml) was stirred at room temperature for 20 minutes, and added to a solution of 46 (1.18 g) and diisopropylethylamine (0.74 ml) in dimethylforamide (3 ml). This mixture was stirred overnight at room temperature and extracted with ethylacetate (2×50 ml) and washed with sodium bicarbonate (30 ml). The crude was purified on a silica gel column (dichloromethane:methanol, 95:5) to provide the t-butyl ester (47, 1.0 g).

The compound 47 was dissolved in dichloromethane (3 ml), trifluoroacetic acid (3 ml) and anisole (1.2 ml), stirred at room temperature for 2 hours and evaporated to dryness. The residue (0.2 g) was mixed with solid sodium bicarbonate (0.1 g), dissolved in water (2 ml) and purified on a C18 column by a gradient of water to 20% acetonitrile in water to provide the sodium salt (48).

A solution of the free acid of 48 (0.1 g) in tetrahydrofuran (1 ml) at −12° C. was mixed with N-ethylmorpholine (0.05 ml) and isobutylchloroformate (0.046 ml) and stirred for 30 minutes. This was added to a solution of O-benzylhydroxyamine hydrochloride salt (0.028 g) and N-ethylmorpholine (0.05 ml) in dimethylforamide (1 ml) and stirred overnight gradually increasing the temperature from −12° C. to room temperature. The reaction mixture was quenched with water (20 ml), extracted with ethyl acetate (50 ml) and washed with sodium bicarbonate solution (20 ml), dried and evaporated. The crude mixture was purified on a silica gel column (dichloromethane:methanol, 9:1) to provide the O-benzylhydroxamide (49, 0.06 g).

The compound 49 (1 g) was dissolved in methanol (20 ml), 5% palladium on carbon (50 mg) was added and the reaction mixture was stirred under hydrogen atmosphere (balloon pressure) for 6 hrs. The mixture was diluted with methanol (20 ml), filtered through celite and concentrated. The residue was crystallized with methanol and ethyl acetate to provide the Compound 50 (640 mg).

EXAMPLE 26

Preparation of N-[2-Isobutyl-3-(N'-hydroxyamidocarbonyl)propanoyl]-L-tryptophan-3 (4-morpholinyl)-n-ethylamide (52)

When 4-morpholinyl ethylamine is substituted for 4-morpholinyl-n-propylamine in Example 25, the identical process afforded the sodium salt (51) and the Compound 52.

EXAMPLE 27

Preparation of N-[2-Isobutyl-3-hydroxycarbonylpropanoyl]-L-tryptophan-(4-pyridyl)methylamide (53)

N-t-Boc-L-tryptophan (5.07 g, 16.66 mmoles) was dissolved in tetrahydrofuran (20 mL) and carbonyldiimidazole (2.70 g, 16.66 mmole) was added to the solution. The reaction was stirred for 1 hour at room temperature, 4-aminomethylpyridine (1.69 mL, 16.66 mmole) was added and the reaction was stirred at room temperature for 3 hours. The solvent was removed and the residue was thoroughly washed with water and dried under vacuum to provide N-t-Boc-L-tryptophan-(4-pyridyl)-methylamide 54 (6.38 g, 97% yield).

The compound 54 (6.38 g, 16.19 mmole) was dissolved in 2N HCl, stirred at room temperature for 24 hours, and concentrated to dryness to give L-tryptophan-(4-pyridyl)-methylamide 55 (5.90 g, 99% yield).

A solution of 4-(t-butoxy)-2R-isobutylsuccinic acid (1.19 g, 5.16 mmole) in tetrahydrofuran (20 mL) was mixed with carbonyldiimidazole (0.84 g, 5.16 mmoles); the reaction was stirred at room temperature for 1 hour and 55 (1.89 g, 5.16 mmole) was added followed by triethylamine (1.44 mL, 10.32 mmole). The reaction was stirred at room temperature for 18 hours, diluted with ethyl acetate (50 mL), washed with saturated aqueous sodium bicarbonate (3×10 mL) and brine (10 mL). The organic phase was dried over anhydrous magnesium sulfate, filtered, concentrated, and the residue was recrystallized from ethyl acetate/hexane to give the t-butyl ester 56 (1.15 g, 44% yield).

The compound 56 (0.12 g, 0.24 mmole) was dissolved in dichloromethane (1 mL), trifluoroacetic acid (1 mL) was added and the reaction was stirred at room temperature for 2.5 hours and then concentrated to dryness. The residue was combined with saturated aqueous sodium bicarbonate (5 mL) and extracted with ethyl acetate (3 mL). The ethyl acetate was dried over anhydrous magnesium sulfate, filtered, concentrated, and the residue was recrystallized from ethyl acetate (1 mL) to yield the Compound 53 (22.6 mg, 21% yield).

EXAMPLE 28

Preparation of N-[2-Isobutyl-3-hydroxycarbonylpropanoyl]-L-tryptophan-benzylamide (57)

When benzylamine is substituted for 4-morpholinyl-n-propylamine in Example 25, the identical process afforded the Compound 57.

EXAMPLE 29

Preparation of N-[2-Isobutyl-3-hydroxycarbonylpropanoyl]-L-tryptophan-2(phenyl)ethylamide (58)

When 2-phenylethylamine is substituted for 4-morpholinyl-n-propylamine in Example 25, the identical process afforded the Compound 58.

EXAMPLE 30

Preparation of N-[2-Isobutyl-3-hydroxycarbonylpropanoyl]-L-tryptophan-2-(4-benzenesulfonamide)ethylamide (60)

When 4-(2-aminoethyl)benzenesulfonamide is substituted for 4-morpholinyl-n-propylamine in Example 25, the identical process afforded the corresponding carboxylic acid 59 and the Compound 60.

EXAMPLE 31

Preparation of N-[D,L-3-isobutyl-3-(hydroxycarbonyl)propanoyl]-L-tryptophan methylamide (61)

N-[D,L-2-isobutyl-3-(hydroxycarbonyl)-propanoyl]-L-tryptophan methylamide (4, 10 g) was dissolved in tetrahydrofuran. The solution was cooled in an ice-bath, and 6N HCl (200 ml) was added. The resulting mixture was stirred at 20°–25° C. for 16–18 hours. The reaction mixture was cooled in an ice-bath and 6N NaOH was added until a pH of 2 was attained. The organic layer was separated and the aqueous layer was extracted with ethyl acetate (200 ml). The organic layers were combined, dried, filtered and concentrated to dryness to yield the Compound 61 (10.5 g). The crude product was purified by flash chromatography using methanol: ethyl acetate gradient at 2%, 5% and 10% to yield pure 61(6.8 g).

EXAMPLE 32

Preparation of N-[D,L-2-Isobutyl-3-(hydroxycarbonyl)propanoyl]-L-tryptophan methylamide (62)

N-[D,L-2-isobutyl-3-(hydroxycarbonyl)-propanoyl]-L-tryptophan methylamide (4, 20 g) was dissolved in methanol (300 ml) and lithium hydroxide (4.33 g) and water (100 ml) was added to the solution at room temperature. The reaction mixture was stirred at 20°–25° C. for 12–16 hours, neutralized with 1N HCl (100 ml, pH 2). The excess methanol was removed in vacuo and the aqueous layer was extracted with ethyl acetate (2×300 ml). The combined organic layers were dried over magnesium sulfate, filtered and concentrated to dryness to yield the title compound 62 (25.7 g). The crude product was recrystallized from acetonitrile (200 ml) to yield pure 62 (6.5 g).

EXAMPLE 33

Preparation of N-[D,L-2-isobutyl-3-(N'-hydroxyamidocarbonyl)propanoyl]-tryltophan methylamide (5A,5B)

N-(2RS-2-Methoxycarbonylmethyl-4-methylpentanoyl)-L-tryptophan (42) was prepared as described above in Example 22. The compound 42 was coupled with methylamine in tetrahydrofuran at room temperature, overnight, using carbonyldiimidazole to yield a mixture of 4A and 4B.

The mixture of 4A and 4B was converted directly to its hydroxamic acid as described in Example 1 above. The compound 5A was crystallized from the mixture of 5A and 5B.

Base hydrolysis of the mother liquor containing 5B on neutralization to pH 5, followed by partial evaporation, yields crystalline L-tryptophan which is recycled for use in the synthesis of 43.

EXAMPLE 34

Preparation of N-[R-2-Isobutyl-3-(N'-hydroxycarbonylamido)-4-phenyl-butanoyl]-L-tryptophan-methylamide (65)

A solution of 4-(t-butoxy)-2R-isobutyl succinic acid (2.3 g, 10 mmol) in tetrahydrofuran was added to a solution of lithium diisopropylamide in tetrahydrofuran (25 mmol) at −45° C. The mixture was gradually warmed to 0° C. and stirred for 3 hours. Benzyl bromide (1.5 ml) was added and the mixture was stirred overnight at room temperature. The mixture was evaporated and the residue was partitioned between dilute sodium bicarbonate solution and ethyl acetate. The aqueous layer was acidified with 1N hydrochloric acid and extracted with ethyl acetate (2×100 ml). The combined organic layers were washed with water (50 ml), brine, dried and concentrated to yield the benzyl derivative 63 (2.3 g).

A solution of 63 in dimethylformamide (6 ml) was mixed with carbonyldiimidazole (1.24 g) and stirred at room temperature for 30 min. L-tryptophan-methylamide hydrochloride (2.2 g) was added and the mixture was stirred overnight at room temperature. The mixture was diluted with ethyl acetate (200 ml), washed with water (50 ml), followed by sodium bicarbonate solution and brine, dried and concentrated. The crude was purified on a silica gel column (95:5 dichloromethane-methanol) to yield the t-butyl ester 64 (1.8 g, 35%).

The t-butyl ester 64 was converted to the Compound 65 according to the procedure described in Example 25.

EXAMPLE 35

Preparation of N-[R-2-Isobutyl-3-hydroxycarbonylpropanoyl]-L-tryptophan-3-(N'N'-dimethyl)-n-propylamide (66)

When 3-N'N'-dimethylamino propylamine is substituted for 4-morpholinyl-n-propylamine in Example 25, the identical process afforded the Compound 66.

EXAMPLE 36

Preparation of N-[R-2-Isobutyl-3-(N'-benzyloxyamidocarbonyl)propanoyl]-tryptophan methylamide (67)

A suspension of 5A (4.9 g, 12.62 mmol), benzyl bromide (1.8 ml, 12.62 mmol) and potassium carbonate (2.6 g, 18.88 mmol) in dimethylformamide (20 ml) was stirred overnight at room temperature. The mixture was poured into ethyl acetate (300 ml), the organic layer was washed with water (2×50 ml), brine, dried and concentrated. The crude was crystallized in ethyl acetate to yield the Compound 67 (3.7 g, 61%).

EXAMPLE 37

Preparation of N-[R-2-Isobutyl-3-(N'-benzyl-N'-hydroxy-amidocarbonyl)propanoyl]-L-tryptophan methylamide (69)

A suspension of 5A (800 mg, 2.06 mmol), benzyl bromide (0.7 ml) and potassium carbonate (1.1 g) in dimethylformamide (5 ml) was stirred overnight at room temperature. The mixture was poured into ethyl acetate (100 ml), the organic layer was washed with water (2×50 ml), brine, dried and concentrated. The crude was purified on a silica gel column (2:1 ethyl acetate:hexane) to yield compound 68 (363 mg, 32%), the N,O-bis-benzyl derivative of 67.

A solution of compound 68 (50 mg) and 5% palladium-on-carbon (5 mg) in methanol (5 ml) was stirred under an hydrogen atmosphere (balloon pressure) for 10 hours. The mixture was filtered over celite, followed by purification on a silica gel column (95:5 chloroform-methanol) to yield the Compound 69 (38 mg).

EXAMPLE 38

Preparation of N-[R-2-Isobutyl-3-(N'-p-fluorophenylmethyl-N'-hydroxyaminocarbonyl)-propanoyl]-L-tryptophan methylamide (71)

A suspension of 67 (200 mg, 0.42 mmol), p-fluorobenzyl bromide (64 μl, 0.51 mmol) and potassium carbonate (87 mg) in dimethylformamide (1 ml) was stirred overnight at room temperature. The mixture was poured into ethyl acetate (30 ml), the organic layer was washed with water (2×10 ml), brine, dried and concentrated. The crude was purified on a silica gel column (95:5 chloroform-methanol) to yield the benzyl derivative 70 (100 mg, 41%).

A solution of Compound 70 (100 mg) and 5% palladium-on-carbon (10 mg) in methanol (5 ml) was stirred overnight under an hydrogen atmosphere (balloon pressure). The mixture was filtered over celite, followed by purification on a silica gel column (95:5 chloroform-methanol) to yield the Compound 71 (50 mg).

EXAMPLE 39

Preparation of N-[R-2-Isobutyl-3-(N'-methoxymethyl-N'-hydroxyamidocarbonyl)-propanoyl]-L-tryptophan methylamide (73)

A suspension of 67 (1 g, 2.1 mmol), iodomethyl pivalate (760 mg, 3 mmol) and potassium carbonate (430 mg) in dimethylformamide (5 ml) was stirred overnight at room temperature. Additional iodomethyl pivalate (760 mg) and potassium carbonate (430 mg) were added and the mixture was stirred overnight at room temperature. The mixture was poured into ethyl acetate (200 ml), the organic layer was washed with water (2×50 ml), brine, dried ($Na_2SO_4$) and concentrated. The crude was purified on a silica gel column (95:5 chloroform-methanol) to yield the ester 72 (300 mg, 24%).

A solution of Compound 72 (300 mg) and 5% palladium-on-carbon (100 mg) in methanol (10 ml) was stirred overnight under an hydrogen atmosphere (balloon pressure). The mixture was filtered over celite, followed by purification on a silica gel column (95:5 chloroform-methanol) to yield the Compound 73 (60 mg).

EXAMPLE 40

Preparation of N-[R-2-Isobutyl-3-(N'-pivalylmethyl-N'-hydroxyamidocarbonyl)-propanoyl]-L-tryptophan methylamide (74)

A solution of compound 72 (300 mg) and 5% palladium-on-carbon (100 mg) in ethyl acetate (10 ml) was stirred overnight under an hydrogen atmosphere. The mixture was filtered over celite, followed by purification on a silica gel column (95:5 chloroform-methanol) to yield the Compound 74 (100 mg).

EXAMPLE 41

Preparation of N-[R-2-Isobutyl-3-(N'-carboxylmethyl-N'-hydroxyamidocarbonyl)-propanoyl]-L-tryptophan methylamide (76)

A suspension of 67 (180 mg) and potassium carbonate (100 mg) in dimethyl-formamide (3 ml) was stirred at room temperature for 30 min. Bromoacetic acid benzyl ester (72 μl) was added and the mixture was stirred for 4 hours. The mixture was poured into ethyl acetate (10 ml), the organic layer was washed with water (2×20 ml), brine, dried and concentrated. The crude was purified on a silica gel column (1% methanol in dichloromethane) to yield the ester 75 (50 mg).

A solution of compound 75 (50 mg) and 5% palladium-on-carbon (5 mg) in methanol (2 ml) was stirred under an hydrogen atmosphere for 2 hours. The mixture was filtered over celite, followed by purification on a silica gel column (95:5 chloroform-methanol) to yield the Compound 76 (18 mg).

EXAMPLE 42

Preparation of Boc-D-gamma-Hydroxamidoglutamyl-L-tryptophan-(S)-methylbenzylamide (79)

Boc-D-glutamic acid gamma benzyl ester was coupled to L-tryptophan-(S)-methylbenzylamide using carbonyldiimidazole in a mixture of dichlomethane and dimethylformamide. The reaction mixture was diluted with ethyl acetate and water and the orgainc phase was washed with sodium bicarbonate, potassium hydrogen sulfate, water and brine. Evaporation of the the ethyl actate layer gave the fully protected intermediate 77.

Deprotection of the intermediate 77 by hydrogenolysis with palladium-on-charcoal in methanol, followed by filtration of the catalyst and evaporation yielded the carboxylic acid 78.

Hydroxaminolysis of the acid 78, using potassium salt of the hydroxylamine hydrochloride in methanol gave the Compound 79.

EXAMPLE 43

Preparation of Boc-D-beta-hydroxamidoaspartyl-1-tryptophan-(S)-methylbenzylamide (82)

Boc-D-aspartic acid gamma benzyl ester was coupled to L-tryptophan-(S)-methylbenzylamide using carbonyldiimidazole in a mixture of dichlomethane and dimethylformamide. The reaction mixture was diluted with ethyl acetate and water and the orgainc phase was washed with sodium bicarbonate, potassium hydrogen sulfate, water and brine. Evaporation of the the ethyl actate layer gave the fully protected intermediate 80.

Deprotection of the intermediate 80 by hydrogenolysis with palladium-on-charcoal in methanol, followed by filtration of the catalyst and evaporation yielded the carboxylic acid 81.

Hydroxaminolysis of the acid 81, using potassium salt of the hydroxylamine hydrochloride in methanol gave the Compound 82.

EXAMPLE 44

Preparation of N-[D,L-2-Isobutyl-3-(N'-hydroxyamidocarbonyl)propanoyl]-tryptophan methylamide (5A,5B)

L-tryptophan is reacted with phosgene to yield the N-carboxyanhydride derivative 83. Compound 83 is reacted with methylamine (1 equivalent) followed by treatment with hydrochloric acid to yield the salt 84.

Isobutyl succinic anhydride in tetrahydrofuran is treated at room temperature with 84, in the presence of a base, to yield a mixture of carboxylic acids 85 and 86. These are esterified with methanol under mild conditions to yield the respective esters 4 and 87.

The mixture of 4 and 87 is converted directly to its hydroxamate as described in Example 1 above. The compound 5A is crystallized from the mixture of 5A and 5B.

Alternatively the acids 85 and 86 can be reacted with acetic anhydride or other coupling agents to yield succinimide derivative 89, which on further hydroxaminolysis gives 5A in high yield.

EXAMPLE 45

Applying the methods set forth above, the following invention compounds are synthesized:
HONHCOCH$_2$CH(n-hexyl)-CO-L-Trp-NHMe;
HONHCOCH$_2$CH(n-pentyl)-CO-L-Trp-NHMe;
HONHCOCH$_2$CH(i-pentyl)-CO-L-Trp-NHMe;
HONHCOCH$_2$CH(ethyl)-CO-L-Trp-NHMe;
HONHCOCH$_2$CH(ethyl)-CO-L-Trp-NHCH$_2$CH$_3$;
HONHCOCH$_2$CH(ethyl)-CO-L-Trp-NHCH$_2$CH$_2$OH;
HONHCOCH$_2$CH(ethyl)-CO-L-Trp-NHcyclohexyl;
MeONHCOCH$_2$CH(iBu)-CO-L-Trp-NHEt;
EtONMeCOCH$_2$CH(iBu)-CO-L-Trp-NHEt;
MeONHCOCH$_2$CH(iBu)-CO-L-Ala(2-naphthyl)-NHEt;
EtONMeCOCH$_2$CH(iBu)-CO-L-Ala(2-naphthyl)-NHEt;
EtONHCONMe-CH$_2$CH(iBu)-CO-L-Trp-NHEt;
EtCONOH-CH$_2$CH(iBu)-CO-L-Trp-NHEt;
n-PrCONOEt-CH$_2$CH(iBu)-CO-L-Trp-NHEt;
EtNHCONOMe-CH$_2$CH(iBu)-CO-L-Trp-NHEt;
MeNHCONOH-CH$_2$CH(iBu)-CO-L-Trp-NHEt;
EtONHCONMe-CH$_2$CH(iBu)-CO-L-Ala(2-naphthyl)-NHEt;
EtCONOH-CH$_2$CH(iBu)-CO-L-Ala(2-naphthyl)-NHEt;
n-PrCONOEt-CH$_2$CH(iBu)-CO-L-Ala(2-naphthyl)-NHEt;

EtNHCONOMe-CH₂CH(iBu)-CO-L-Ala(2-naphthyl)-NHEt;
MeNHCONOH-CH₂CH(iBu)-CO-L-Ala(2-naphthyl)-NHEt;
HONHCONHCH₂CH(iBu)-CO-L-TrpNHMe;
HONHCONHCH₂CH₂CH(iBu)-CO-L-TrpNHMe;
HONHCONHCH(iBu)CO-L-TrpNHMe;
H₂NCON(OH)CH(iBu)CO-L-TrpNHMe;
N(OH)CH₂CH(iBu)-CO-L-TrpNHMe;
H₂NCON(OH)CH₂CH₂CH(iBu)-CO-L-TrpNHMe;
CH₃CON(OH)CH(iBu)-CO-L-TrpNHMe;
CH₃CON(OH)CH₂CH(iBu)-CO-L-TrpNHMe;
CH₃CON(OH)CH₂CH₂CH(iBu)-CO-L-TrpNHMe;
HNOHCOCH₂CH(i-Bu)CO-L-Trp-NHMe;
HONHCOCH₂CH(i-Bu)CO-L-TrpNH(CH₂)₃-(4-morpholinyl);
HONHCOCH₂CH(i-Bu)CO-L-TrpNH(CH₂)₂-(4-morpholinyl);
HOOCCH₂CH(i-Bu)CO-L-TrpNHCH₂Ph;
HOOCCH₂CH(i-Bu)CO-L-TrpNHCH₂CH(-4-pyridyl);
HOOCCH₂CH(i-Bu)CO-L-TrpNH(CH₂)₂Ph;
HOOCCH₂CH(i-Bu)CO-L-TrpNH(CH₂)₂-(4-benzenesulfonamide);
HOOCCH(i-Bu)CH₂CO-L-TrpNHMe;
HOOCCH₂CH(i-Bu)CO-L-TrpNHMe;
HONHCOCH(i-Bu)CH₂CO-L-TrpNHMe;
BnONHCOCH₂CH(i-Bu)CO-L-TrpNHMe;
HON(Bn)COCH₂CH(i-Bu)CO-L-TrpNHMe;
HON(p-fluoro-Bn)COCH₂CH(i-Bu)CO-L-TrpNHMe;
BnON(CH₂OCH₃)COCH₂CH(i-Bu)CO-L-TrpNHMe;
HON(CH₂OPiv)COCH₂CH(i-Bu)CO-L-TrpNHMe;
HON(CH₂COOH)COCH₂CH(i-Bu)CO-L-TrpNHMe;
HONHCOCH(Bn)CH(i-Bu)CO-L-TrpNHMe;
HOOCCH₂CH(i-Bu)CO-L-TrpNH(CH₂)₃NCH₃;
HOOC(CH₂)₂CH(NHCOO-t-Bu)CO-L-TrpNCH(CH₃)Ph;
HONHOC(CH₂)₂CH(NHCOO-t-Bu)CO-L-TrpNCH(CH₃)Ph;
HOOCCH₂CH(NHCOO-t-Bu)CO-L-TrpNCH(CH₃)Ph; and
HONHOCCH₂CH(NHCOO-t-Bu)CO-L-TrpNCH(CH₃)Ph.

Determination of the inhibitory activity of certain of the compounds prepared is conducted as described above, and provides the results shown in Table 1 and Table 2.

TABLE 1

| No. | | Compound | $K_i$(nM) |
|---|---|---|---|
| 1 | 5A | NHOHCOCH₂CH(i-Bu)CO-L-Trp-NHMe | 10 |
| | 5B | NHOHCOCH₂CH(i-Bu)CO-L-Trp-NHMe | 150 |
| 2 | 7A | NHOHCOCH₂CH(i-Bu)CO-D-Trp-NHMe | 70,000 |
| 3 | 9A | NHOHCOCH₂CH(i-Bu)CO-L-N-MeTrp-NHMe | 500 |
| 4 | 11A | NHOHCOCH₂CH(i-Bu)CO-L-Ala(2-naphthyl)NHMe | 15 |
| 5 | 13A | NHOHCOCH₂CH(i-Bu)CO-L-Trp-NH(CH₂)₂OH | 20 |
| 6 | 15A | NHOHCOCH₂CH(i-Bu)CO-L-Trp-NH(CH₂)₄CH₃ | 30 |
| 7 | 17A, B | NHOHCOCH₂CH(i-Bu)CO-L-Trp-piperidine | 200 |
| 8 | 19A | NHOHCOCH₂CH(i-Bu)CO-L-Trp-NH(CH₂)₁₁CH₃ | 300 |
| 9 | 21A | NHOHCOCH₂CH(i-Bu)CO-L-Trp-NH(S)CHMePh | 3 |
| 10 | 27A | NHOHCOCH₂CH(i-Bu)CO-L-Trp-NH(CH₂)₆NH-CBZ | 13 |
| 11 | 28A | NHOHCOCH₂CH(i-Bu)CO-L-Trp-NHcyclohexyl | 50 |
| 12 | 29A, B | cis-HNOCO—[cyclohexyl]—C(O)—L—Trp—NHMe | >10,000 |
| 13 | 30A, B | trans-HNOCO—[cyclohexyl]—C(O)—L—Trp—HMe | >10,000 |
| 14 | 31A | NHOHCO-CH₂CH(i-Bu)-L-Trp-OH | 200 |
| 15 | 32A | HOOC-CH₂CH(i-Bu)CO-L-Trp-NH(CH₂)NH₂ | >10,000 |
| 16 | 34A | HOCO-CH₂CH(i-Bu)CO-L-Trp-Gly-OH | >10,000 |
| | 34B | HOCO-CH₂CH(i-Bu)CO-L-Trp-Gly-OH | >10,000 |
| 17 | 35 | cis-HOCO—[cyclohexyl]—C(O)—L—Trp—NHMe | >10,000 |

TABLE 1-continued

| No. | Compound | $K_i$(nM) |
|---|---|---|
| 18 | 36 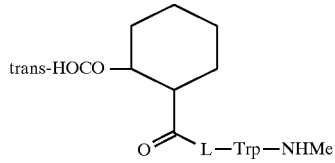 | >10,000 |

TABLE 2

| Comp# | 72kD G[a] | 92kD G[b] | Strom[c] | NC[d] | HGFC[e] |
|---|---|---|---|---|---|
| 5A | 0.26 | 0.22 | 27 | 0.12 | — |
| 5B | 298 | — | >1000 | 54 | 23 |
| 9A | 32 | — | >1000 | 29 | 5 |
| 11A | — | — | — | — | 0.3 |
| 13A | — | — | — | — | 1 |
| 15A | — | — | — | — | 0.3 |
| 17 | — | — | — | — | — |
| 19A | 0.37 | 1.29 | 40 | 0.62 | 0.001 |
| 20A | — | — | — | — | 0.2 |
| 21A | — | — | — | — | 0.001 |
| 27A | 2.9 | — | 94 | 21 | 0.1 |
| 28A | 4.0 | — | 78 | 1.0 | 0.1 |
| 29 | — | — | — | — | — |
| 30 | — | — | — | — | — |
| 31A | — | — | — | — | — |
| 32A | — | — | — | — | — |
| 34A | — | — | — | — | — |
| 34B | — | — | — | — | — |
| 35 | — | — | — | — | — |
| 36 | — | — | — | — | — |
| 48 | 145 | 65 | 19331 | 32 | — |
| 50 | — | — | — | — | — |
| 51 | — | — | — | — | 32 |
| 52 | 0.81 | 0.97 | 57 | 0.19 | 0.6 |
| 53 | — | — | — | — | — |
| 57 | 57 | 37 | 5145 | 20 | 2.2 |
| 58 | 79 | — | 10587 | 26 | — |
| 59 | 265 | — | 38178 | 85 | — |
| 60/61 | — | — | — | — | 3 |
| 78 | >10000 | >10000 | >10000 | >10000 | 2000 |
| 79 | >10000 | 21098 | >10000 | >10000 | 60 |
| 81 | >10000 | >10000 | >10000 | >10000 | 500 |
| 82 | 9262 | 3585 | >10000 | 3265 | 80 |

Units for all the above measurements are in nmoles.
[a]Natural human 72kD gelatinase
[b]92kD gelatinase
[c]Stromelysin
[d]Recombinant neutrophil collagenase
[e]Human gingival fibrblast collagenase

EXAMPLE 46

Inhibition of Angiogenesis

A crude extract (30 mg/mL protein) of Walker 256 carcinoma, a rat malignant tumor, was incorporated into Hydron, a slow release polymer, in 1.5 mm diameter pellets. Pellets were implanted in the stroma of the corneas of anesthetized albino rats. A cannula was chronically implanted in the inferior vena cava, through which 10 mg/mL of compound 5A in 55% DMSO in water was infused continuously for six days at the rate of 0.8 mL/24 hr. Controls received only the DMSO solution. After six days, the animals were re-anesthetized and perfused intra-arterially with India ink in order to visualize the corneal vessels. The eyes were then enucleated and fixed in 5% formalin. Control eyes which received only the DMSO solution show massive vessel growth toward the pellet from the limbus. The animals receiving compound 5A show vessels much shorter and/or much finer than in the controls, barely filling with ink.

EXAMPLE 47

Treatment of Psoriasis

The effect of the compound 5A on psoriasis was studied using a phorbol ester induced epidermal hyperplasia mouse model. The 12-O-tetradecanoylphorbol-13-acetate (TPA) hyperplasia model was chosen as it is a widely accepted model for screening antiproliferative agents. A single, topical application of TPA produces a pronounced epidermal hyperplasia and a strong inflammatory response in mice as is observed in psoriasis (Argyris, T. S. (1980) Am. J. Pathol. 98: pages 639–648).

In this model system, epidermal hyperplasia is clearly evident histologically at 3 to 5 days following TPA treatment. In addition to TPA other, more stable, phorbol esters produce the same effect including phorbol-12,13 dibutyroyl (PdiBu).

The following procedures was carried out to test the effects of the invention compounds in the above described epidermal hyperplasia animal model.

The phorbol ester, PdiBu (20 nmol in 20 μl if acetone) was applied to both ears of hairless mice (h/h) (approximately 1 cm² each). The test compounds (in total volume of 20 μl) were then applied to the right ear immediately (15 to 30 min) following PdiBu. The left ear of each animal received an equivalent amount (20 μl) of vehicle. Test compounds (and vehicle) were reapplied at 6 and 18 hours following PdiBu. Treatment times were staggered to allow exact time intervals to be obtained. At 30 hours after PdiBu, animals were anesthetized, and ear thickness values were obtained using a microcaliper. The weights of punch biopsies (6 mm) were then obtained. Histology was performed on selected samples taken at 30 hours.

Test compounds included 5A (10 mg/ml in ETOH), a negative control, acetohydroxamic acid (AHA; 2 mg/ml in ETOH), and fluocinonide (Lidex[R]) as a positive control (0.05% in vehicle of alcohol [35%], diisopropyl adipate, citric acid and propylene glycol).

Left ear in each animal served as vehicle-treated controls (PdiBu+ETOH). Thus, the controls for this series include: 1) Untreated controls; 2) PdiBu plus vehicle alone (included for each mouse tested); 3) PdiBu plus AHA; 4) PdiBu plus Lidex[R] as a positive control.

Table 3 shows the results.

TABLE 3

Effects of Compound 5A on PdiBu-Induced Epidermal Hyperplasia

Ear Thickness: Topical 5A (0.51 μmol/ear; 20 μl of 10 mg/ml = 200 μg/cm²) applied at each of three timepoints (0.25, 6.0, and 24 hours) significantly inhibited PdiBu-induced ear thickness:

|  | Thickness (inch × 10⁻³) | % of Control | n |
|---|---|---|---|
| Control (untreated)[a] | 13.3 ± 0.1 | (100%) | 12 |
| PdiBu + Vehicle | 30.4 ± 2.1 | 229% | 8[b] |
| PdiBu + 5A | 18.6 ± 1.6 | 140% | 8[b] |

Skin Biopsy Weight: Topical 5A (0.51 μmol/ear applied at each of two timepoints: 0.25, and 24 hours) significantly inhibited PdiBu-induced increase in punch biopsy weight (6 mm):

|  | Weight (mg) | % of Control | n |
|---|---|---|---|
| Control (untreated)[a] | 9.2 ± 0.2 | (100%) | 12 |
| PdiBu + Vehicle | 22.9 ± 1.8 | 249% | 7[c] |
| PdiBu + 5A | 13.4 ± 1.5 | 146% | 7[c] |

[a]Untreated control values were pooled from three experiments
[b]Results represent mean ± S.E. for three experiments (6 hr dosage was omitted).
[c]Results represent mean ± S.E. for three experiments (6 hr dosage was omitted).

Histology: Analysis of stained skin samples revealed that topical 5A inhibited the PdiBu-induced:
1) migration of inflammatory cells both into dermis and epidermis;
2) extravasation of RBC's;
3) epidermal hyperplasia; and
4) resulted in more normal appearing epidermal morphology (i.e. reduction of PdiBu-induced parakeratosis, and reduction of irregular basaloid, spinous and granular cell shape and distribution).

Note: Histologic analysis were performed both on ear and flank samples with similar results; both sites received 20 nmol PdiBu; however, ear received 20 μl 6001 (200 μg) over an area of approximately 1 cm², while flank received 50 μl (500 μg) over an area of approximately 4 cm². Skin samples were prepared using standard histologic methods and stained with hematoxylin/eosin.

Figures 1A, 1B:
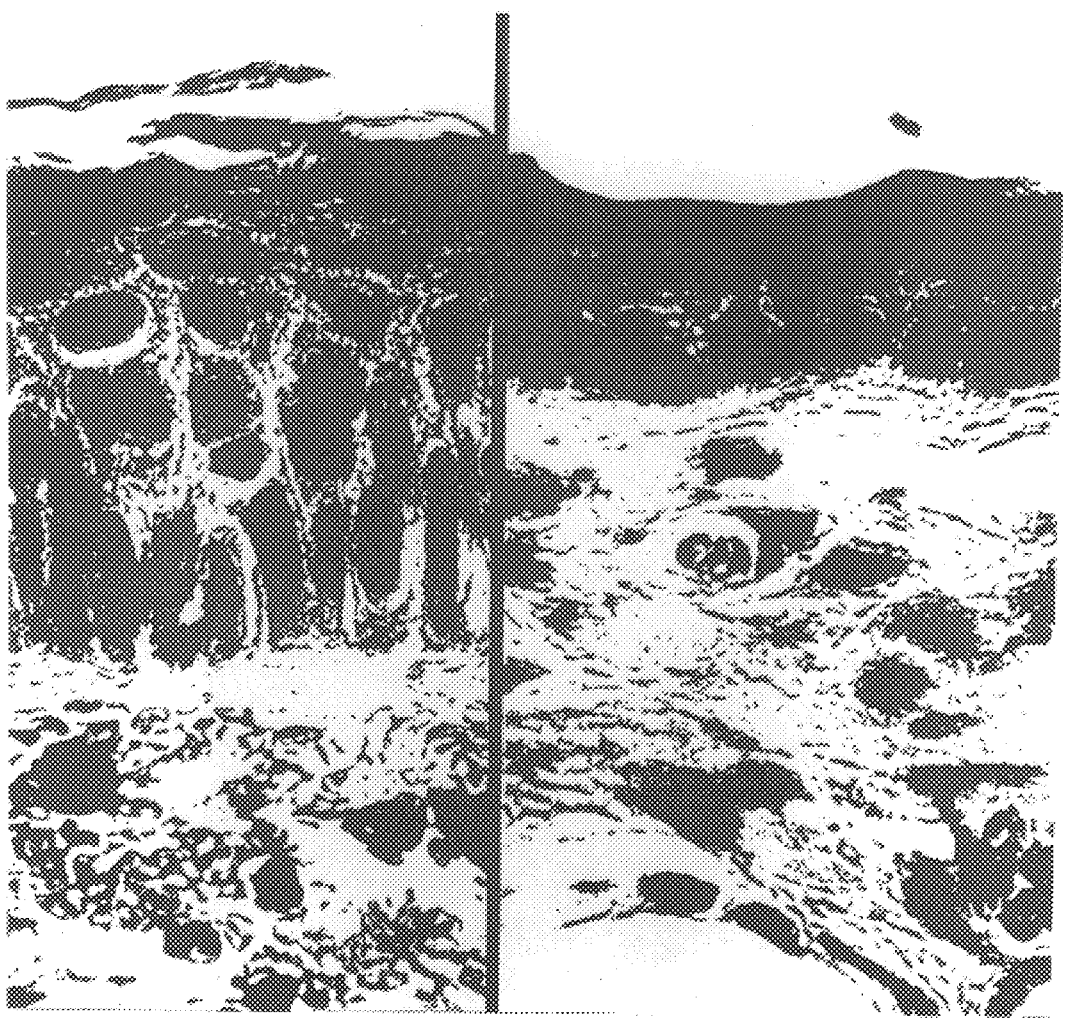
FIG. 1 shows light microscopic photographs of mouse skin exposed to PdiBu (panel A), or PdiBu and compound 5A (panel B) and stained with hematoxylin and eosin three days later.

FIG. 1 shows typical sections of mouse skin exposed to PdiBu (Panel A) or PdiBu and 5A (Panel B). It is clear that 5A completely prevents PdiBu-induced epidermal hyperplasia.

AHA Control: Topical AHA (0.53 μmol/ear applied at each of three timepoints: 0.25, 6.0, and 24 hours) did not alter the PdiBu-induced increase in ear thickness and biopsy weight:

|  | Thickness (inch × 10⁻³) | Weight | n |
|---|---|---|---|
| Control (untreated)[d] | 13.3 ± 0.1 | 9.2 ± 0.2 | 12 |
| PdiBu + Vehicle | 35.5 ± 1.3 | 25.9 ± 0.8 | 6[e] |
| PdiBu + AHA | 36.8 ± 1.3 | 24.1 ± 1.2 | 6[e] |

[d]Untreated control values were pooled from three experiments.
[e]Results represent mean ± S.E. for two experiments.

Positive Control: Lidex[R] (fluocinonide) significantly inhibited the PdiBu-induced increase in ear thickness and biopsy weight:

|  | Thickness | Weight | n |
|---|---|---|---|
| Control (untreated)[f] | 13.3 ± 0.1 | 9.2 ± 0.2 | 12 |
| PdiBu + Vehicle | 33.6 ± 1.2 | 24.4 ± 1.1 | 6[g] |
| PdiBu + AHA | 15.8 ± 0.4 | 9.7 ± 0.3 | 6[g] |

[f]Untreated control values were pooled from three experiments.
[f]Results represent mean ± S.E. for single experiment.

To summarize, 5A demonstrated potent anti-inflammatory activity in this standard in vivo model for psoriasis. The extent of anti-inflammatory activity was nearly comparable to that observed with Lidex[R], the positive control. The reduction of PdiBu-induced ear weight was accompanied by similar inhibition of ear thickening. Moreover, decreased inflammation and epidermal hyperplasia were evident by histologic analysis. Acetohydroxamic acid (AHA) was used as a negative control since it is devoid of inhibitory effects on MMPs. It did not alter PdiBu-induced effects on ear thickness or weight.

EXAMPLE 48

Treatment of Chronic Dermal Wounds

Experiments were done to show the presence of matrix metalloproteinase activity in certain types of wounds, and the inhibition of such protease activity with the appropriate invention inhibitor.

Fluids were collected from 3 types of human wounds termed closed spontaneously healing wounds, open slowly healing wounds, and open chronic wounds. In the first category were fluids collected from the chest wall of women following mastectomy surgery. Fluids from non-infected wounds that were left open for valid surgical reasons were considered open slowly healing wounds. An occlusive dressing was placed over the wound bed, and fluids were collected after 2–6 hours of occlusion. Finally, fluids were also collected from chronic open wounds by covering the wounds with occlusive dressings. Wounds were considered to be chronic if they were not clinically infected and had been open and not healing for more than 4 weeks.

The various wound fluids were assayed for matrix metalloproteinase activity using the Azocoll assay essentially as described by Chavira, et al., *Analytic Biochemistry* (1984), 136:446.

The fluids were centrifuged, and the supernatants filtered using a 0.45 u sterile Gelman filter. The filtrates were stored frozen at −80° C. until tested for protease activity.

The effects of four inhibitors on the protease activity present in wound fluids were determined. The inhibitors were: compounds 5A [NHOHCOCH2CH(i-Bu)CO-tryptophan-NHMe], 21A [NHOHCOCH2CH(i-Bu)CO-tryptophan-NHCHMePh], 39A [HOOCCH2CH(i-Bu)CO-tryptophan-NHCHMePh], and S1209 [NHOHCOCH2CH(i-Bu)CO-tyrosine-OMeNHMe].

These inhibitors were compared to certain other inhibitors and these were UL001 [HSCH₂CH(CH₂CH(CH₃)₂)CO-Phe-Ala-NH₂] obtained from Peptides International and MP506, obtained from Elastin Products. EDTA (ethylenediamine tetraacetic acid) and PMSF (phenylmethylsulfonyl fluoride) were also studied.

Stock solutions of the four inhibitors were all prepared at a concentration of 800 µg/ml. Due to different solubility properties of the inhibitors, different techniques were utilized. 5A was dissolved in an amount of warmed propylene glycol to give a final concentration of 2.4%, then dissolved in 10 mM citrate, pH 5.5, containing 0.05% methyl cellulose. S1209 was dissolved in 1% DMSO then dissolved in 10 mM citrate, pH 5.5, containing 0.05% methyl cellulose. 39A was dissolved in propylene glycol (to give a final concentration of 2.4%) then dissolved in 1 mM $CaCl_2$, 50 mM Tris-Cl, pH 7.8. 21A was dissolved in propylene glycol (2.4%) methyl cellulose (0.05%) and 10 mM citrate, pH 8.

The protease substrate, Azocoll, was obtained from Sigma Chemical Corporation and it is a substrate for collagenase/gelatinase-like metalloproteinase enzymes and general proteases. *Clostridium histolyticum* collagenase (the crude form of the enzyme) was from Worthington Biochemicals. General chemicals including TRIS buffer, DMSO, and $CaCl_2$ were from Sigma Chemical Corporation.

Briefly, 900 µl of the Azocoll substrate suspension in buffer (5 µg/ml in 50 mM TRIS, pH 7.8, 1 mM $CaCl_2$) was added to 1.5 ml microcentrifuge tubes then 50 µl of inhibitor (or buffer) and 50 µl of chronic wound fluid (or collagenase standard) were added to the reaction tube. The reaction tubes were placed at 37° C. in a shaker that inverted the tubes 30 times per minute. After 24 hours of incubation, the reaction tubes were centrifuges at 10,000×g and the absorbance of the supernatant solution was measured at 520 nm with a Milton-Roy spectrophotometer. Proteolysis of Azocoll substrate generates soluble colored fragments from the insoluble Azocoll substrate. Wound fluid samples were incubated alone or with the inhibitors. Controls included incubation of the Azocoll substrate with the assay buffer to measure spontaneous degradation of the substrate. A standard curve for digestion of the Azocoll substrate was generated by incubation of the Azocoll with crude bacterial collagenase. Protease levels were expressed as net µg of collagenase equivalent per ml of chronic wound fluid. In the figures, certain of the wound fluids are referred to by an individual name.

Figure 2:
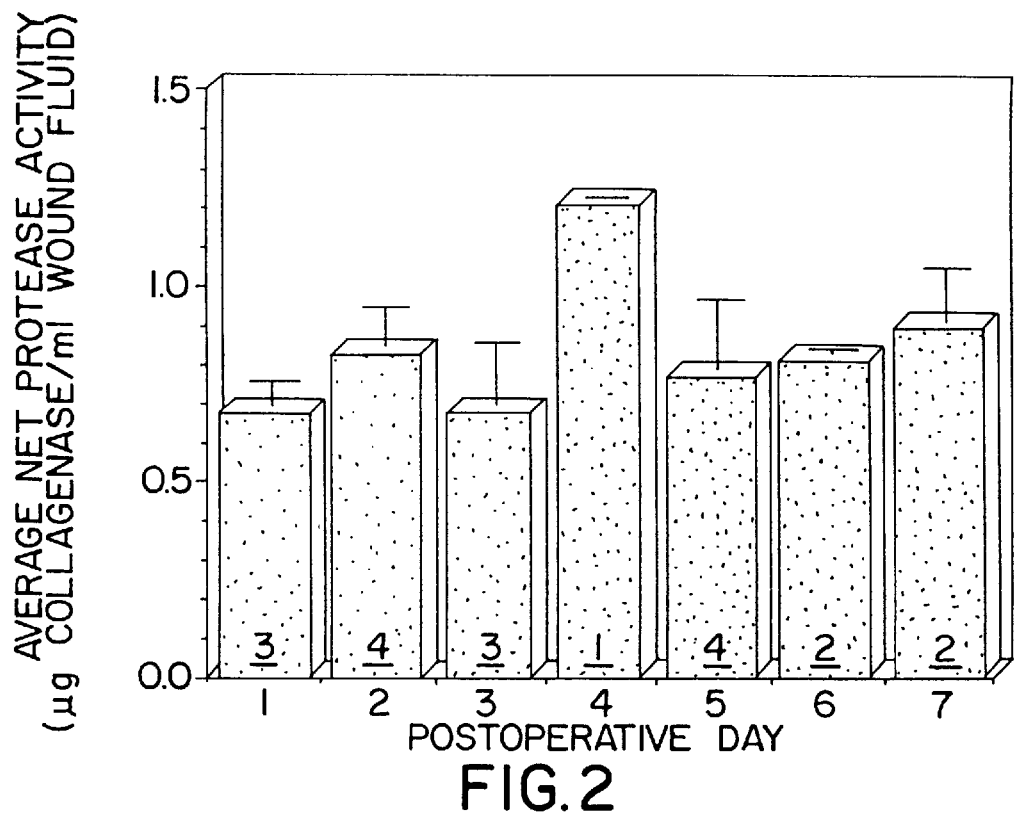
FIG. 2 shows that the protease levels present in mastectomy fluid samples collected on days 1 to 7 after surgery were an average of 0.75±0.06 μg equivalents of collagenase/ml of wound fluid.

FIG. 2 shows the results. Mastectomy fluid samples collected on days 1 to 7 after surgery contained low levels of protease activity with an average of 0.75±0.06 µg equivalents of collagenase/ml of wound fluid. In contrast, FIG. 3 shows that wound fluids collected. from open wounds contained an average protease level of 199±59 µg/ml of wound fluid, and fluids collected from chronic wounds contained an average protease level of 125±95 µg/ml. Only one of the thirteen samples of fluids, L. Smith, from chronic or open wounds did not contain measurable levels of Azocoll hydrolysis activity. The protease levels of the remaining twelve samples of open and chronic wounds were all higher than the levels measured in mastectomy fluids and ranged from 2 to 585 µg/ml wound fluid.

Thus it is clear that fluids collected from chronic and open wounds contain very high levels of Azocoll-degrading protease activity compared to fluid collected from mastectomy drains. This suggests that the in vivo environment of open or chronic wounds contains proteases that have the ability to degrade extracellular matrix proteins of wounds.

Having established the levels of protease activity in various wound fluids, the effect of three protease inhibitors were measured. As shown in FIG. 4, 5A very effectively inhibited proteolytic degradation of Azocoll (approximately 96% of initial proteolytic activity) by a chronic wound fluid when added at final concentrations of 40 µg/ml (100 µM) or 4 µg/ml (10 µM). Lower concentrations of 5A [4 µg/ml (1 µM) and 0.4 µg/ml (0.1 µM)] inhibited approximately 92% of nontreated protease levels. Addition of EDTA, which is a nonspecific inhibitor of metalloproteinases, also effectively reduced protease activity (inhibited approximately 96%). However, the effective concentrations of 5A were µM while the concentrations of EDTA were mM. Addition of PMSF, a nonspecific inhibitor of serine proteases, reduced proteolytic activity approximately 65% when added to a concentration of 500 µM. Lower concentrations of PMSF (500 µM and 50 µM) actually slightly increase the levels of protease activity. CW in the figure refers to wound fluid not treated with protease inhibitor.

To conclude, both 5A and EDTA effectively inhibited the protease activity of a chronic wound fluid, but 5A was much more potent that EDTA. PMSF was not an effective inhibitor except at the highest concentration. This indicates that much of the proteolytic activity present in the chronic wound fluid was due to metalloproteinases. The inhibition observed with high concentration of PMSF was most likely due to nonspecific inhibition of non-serine proteases which has been reported at high concentrations of PMSF (see, for example, Arch. Biochem. Biophys. 124:70).

Additional experiments were conducted to ascertain the effects of certain inhibitors on open and chronic wounds, and the results are shown in FIG. 5. 5A and EDTA were very effective inhibitors while PMSF did not significantly reduce proteolytic activity of the wound fluids.

To summarize, 5A and EDTA consistently reduced proteolytic activity by 95% in open or chronic wound fluids with high levels of Azocoll-degrading protease activity. PMSF did not reduce the levels of proteolytic activity. This supports the general concept that open and chronic wounds consistently have elevated levels of matrix metalloproteinases which can effectively be inhibited by 5A.

A further experiment was performed to determine the effects of a series of matrix metalloprotease inhibitors on the proteolytic degradation of Azocoll by wound fluids. In this experiment, 5A, S1209, UL001, and EDTA inhibited proteolytic activity of wound fluids very effectively. For example, these inhibitors reduced proteolytic activity of Christi wound fluid by 97% to 94% (from 404 µg collagenase/ml to 9 to 18 µg collagenase/ml wound fluid). However, MP506 was substantially less effective than the other inhibitors. In 3 of the 4 open and chronic wounds, MP506 did not reduce the levels of protease activity. FIG. 6 summarizes the results.

Based on the above results, 5A and S1209 are very effective inhibitors of Azocoll-degrading proteases in a larger series of wound fluids. MP506 was a somewhat less effective inhibitor than 5A or S1209.

Finally, experiments were conducted to ascertain the effects of 5A, 21A, 39A, and S1209 on the protease activity present in chronic wound fluid.

For these experiments, due to the different solubility properties of the inhibitors, different techniques were utilized. 5A was dissolved in an amount of warmed propylene glycol to give a final concentration of 2.4%, then dissolved in 10 mM citrate, pH 5.5, containing 0.05% methyl cellulose. S1209 was dissolved in 1% DMSO then dissolved in 10 mM citrate, pH 5.5, containing 0.05% methyl cellulose. 39A was dissolved in propylene glycol (to give a final concentration of 2.4%) then dissolved in 1 mM $CaCl_2$, 50 m Tris-Cl, pH 7.8. 21A was dissolved in propylene glycol (2.4%) methyl cellulose (0.05%) and 10 mM citrate, pH 8.

As shown in FIG. 7, the chronic wound fluid contained a high level of protease activity with an average of 284±52 µg collagenase equivalents/ml of wound fluid. Addition of 5A at 800 µg/ml reduced the level of protease activity by 84% to 45±1 µg collagenase equivalents/ml of wound fluid. Lower concentrations of 5A resulted in slightly higher levels of protease activity up to 90±6 µg collagenase equivalents/ml of wound fluid. 21A and S1209 also effectively inhibited the protease activity of the chronic wound fluid, with the highest concentration (800 µg/ml) inhibiting 94% and 70%, respectively (see Table 3). In contrast, even the highest level of 39A only inhibited 23% of the protease activity, and 13% and 30% increases were measured at the 8 µg/ml and 0.8 µg/ml concentrations.

To summarize, all three inhibitors at the highest concentration reduced the proteolytic degradation of Azacoll. However, 39A was significantly less potent that 5A, 21A, or S1209 and lower concentrations of 39A actually increased the level of proteolytic activity of the chronic wound fluid.

EXAMPLE 49

Thioglycollate Induced Peritonitis Assay

The effect of 5A on preventing thioglycollate induced infiltration of neutrophils in the peritoneal cavity was measured by the following procedure.

6–8 week old Balb/c male mice were used (n=10 each for the treated and control groups). Thioglycollate suspension (5.9 g/l in deionized water) was boiled until the color was golden, then cooled yielding a pink color. The lavage solution consisted of saline supplemented with 0.1% bovine serum albumin (100 mg/100 ml) and 5 U heparin/ml.

Thioglycollate (1 ml/animal) was injected intraperitoneally (i. p.) at time T=0. 5A (800 µg/ml, 1 ml/animal) was injected i. p. at time T=0.5, 1.0, and 2.0 hr. post thioglycollate injection. Cells were collected by lavage at T=3.0 hr. post thioglycollate administration. The animals were euthanized by $CO_2$ asphyxiation, and the abdominal skin was cut with surgical scissors to reveal the peritoneal cavity. Five ml of lavage fluid was injected into the peritoneum, and a suspension was made by gentle massage. The fluid was removed by syringe, recovering about 80% of the injected fluid. Total cell counts in the lavage fluid were determined by Coulter Counter.

The average number of cells in the peritoneum of mice treated with 5A was significantly reduced (p=0.0141) from the average number of cells in the peritoneum of mice injected with vehicle alone. FIG. 8 shows the effects of the inhibitor 5A on thioglycollate induced peritonitis assay.

EXAMPLE 50

Metastasis Assay In C57 Mice

This assay was performed to determine the antimetastatic potential of 5A in an in vivo experimental metastasis assay in C57 mice. Female C57 BL/6 mice, 4–6 weeks old (15–20 grams), from Simonsen Laboratories (Gilroy, Calif.) were used for this assay.

The B16-F10 murine melanoma was obtained from the American Type Tissue Culture Collection, and routinely propagated in DMEM (Dulbecco's modified eagles medium)+10% fetal calf serum in plastic tissue culture flasks in a humidified 5% $CO_2$ incubator at 37° C. B16-F10 tumor cells were harvested with trypsin-EDTA (ethylenediamine-tetraacetic acid), washed with PBS (phosphate buffered saline, 2×), resuspended at a concentration of $5\times10^5$ cells/ml, and held on ice prior to injection. Animals were challenged with $5\times10^4$ cells in a volume of 0.1 ml intravenously (10 animals/treatment group). Animals were randomly distributed prior to assignment to treatment groups.

5A suspension (0.1 ml, 4% (w/v) in filter sterilized carboxy methyl cellulose) or suspension vehicle was injected into the peritoneum (ip) of C57 BL/6 mice 24 hours prior to tumor cell challenge. 30 minutes prior to challenge animals were dosed with 5A or suspension vehicle, and 50,000 B16-F10 tumor cells injected iv. in a solution of 5A in ophthalmic vehicle (800 µg/ml) or ophthalmic vehicle alone, after incubation for 30 minutes at room temperature prior to injection (0.1 ml/mouse). Animals were then dosed with 5A (150 mg/kg/d, ip) suspension or vehicle for 4 additional days.

Survival times were recorded for animals in the various treatment groups, and results were evaluated using Chi-Squared statistical analysis.

Results of the assay are shown in FIG. 9. There was a significant increase in the survival of mice treated with 5A versus vehicle control on days 35–37 (p<0.05).

EXAMPLE 51

Effect of 5A on Hypovolemic Shock in a Non-Heparinized Animal

This assay was performed to determine the effect of 5A on cardiovascular function, hepatocellular function and microcirculation following trauma-hemorrhage and resuscitation.

This experiment relates to metalloprotease inhibitors in treating hypovolemic shock when administered systemically (via i.v. injection, infusion or other appropriate route) during resuscitation following hemorrhage-induced shock in a non-heparinized animal. See, Chaudry et al., *Circ. Shock* (1989) 27:318. 5A was prepared as a suspension at 100 µg/ml in Ringer's lactate.

Sprague-Dawley rats (weighing approximately 300 g, 6 in each group: sham, saline and 5A) were lightly anesthetized with ether and various blood vessels were cannulated for the study (Wang, P. et al, Am. J. Physiol. (1990) 259:R645). Following hemorrhage, Ringer's lactate (3× maximum bleedout volume) was given over 45 minutes followed by Ringer's lactate (2× maximum bleedout volume) over 60 minutes. A dose of 5A suspension (0.75 ml, 40 mg/ml) was given subcutaneously at the time of completion of the 3× Ringer's lactate. Two times Ringer's lactate containing 5A (0.1 mg/ml) was provided as a second portion of the fluid resuscitation (total dose of approximately 107 mg/kg body weight). Sham-operated animals underwent blood vessel cannulation and midline incision, but hemorrhage and resuscitation was not induced. These rats did not receive 5A. Saline-treated underwent trauma-hemorrhage and fluid resuscitation plus vehicle (an equal volume of normal saline) treatment.

Figure 13A:
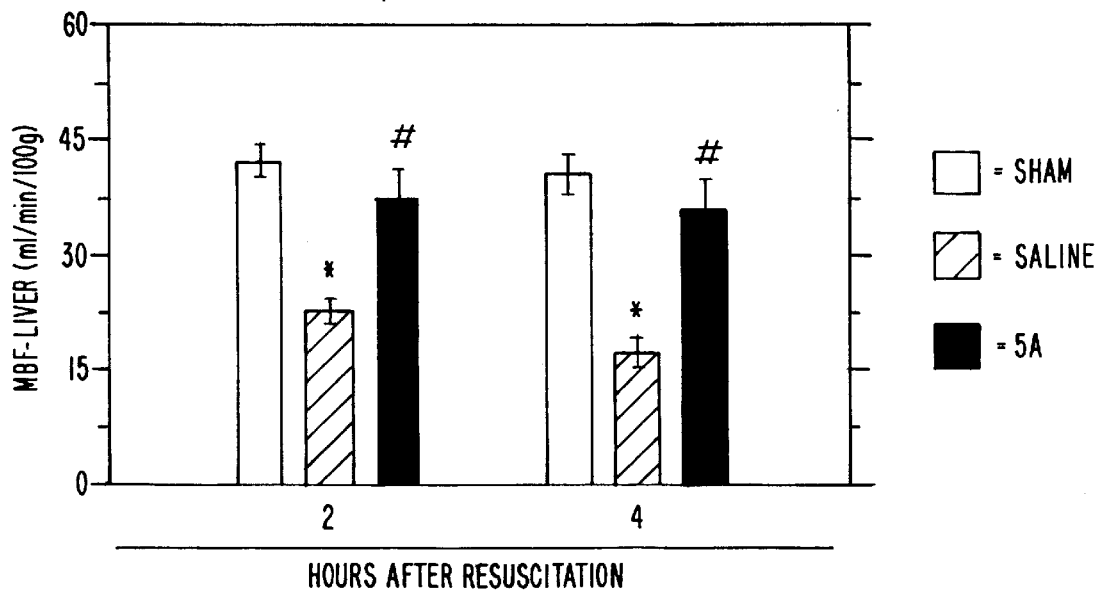
Figure 13B:
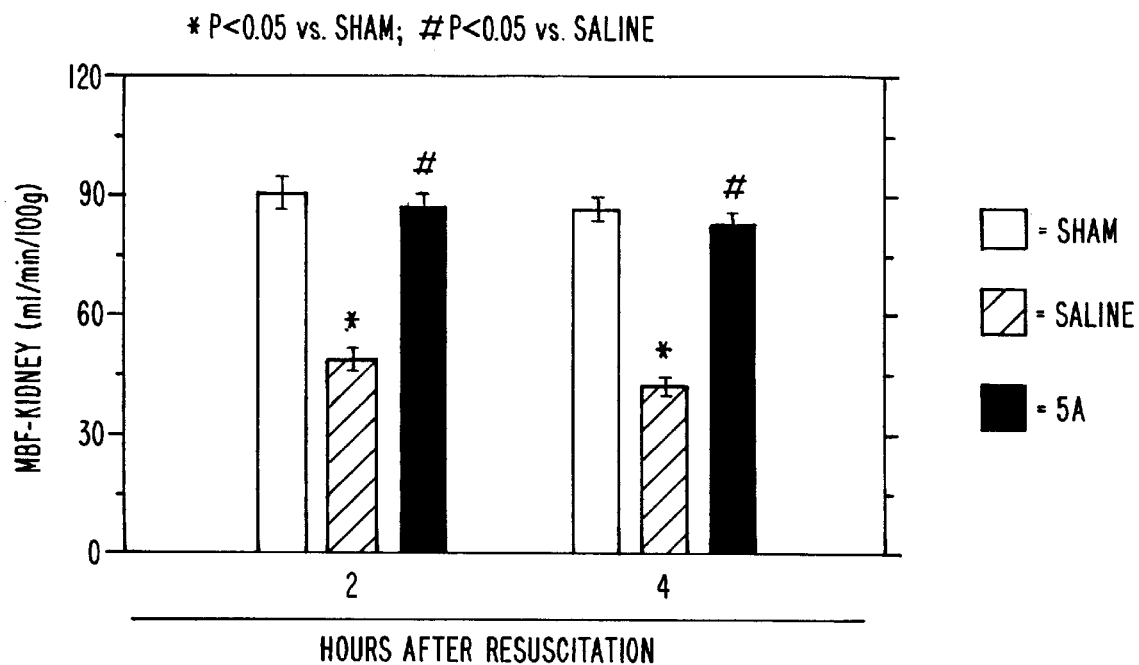
Figure 13C:
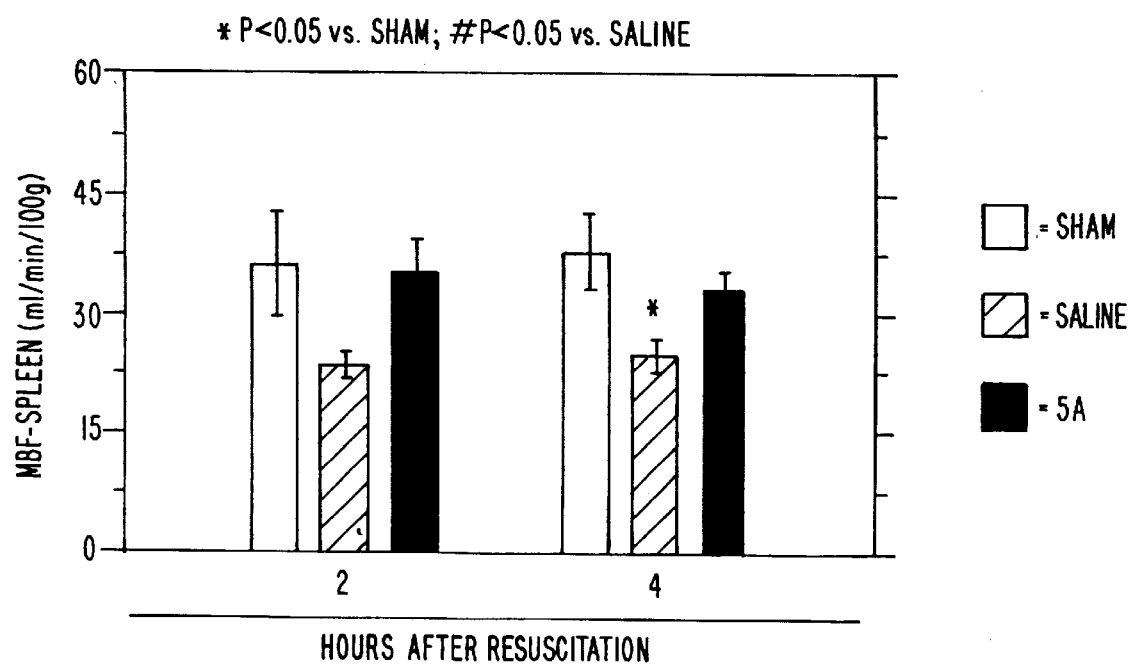
Figure 13D:
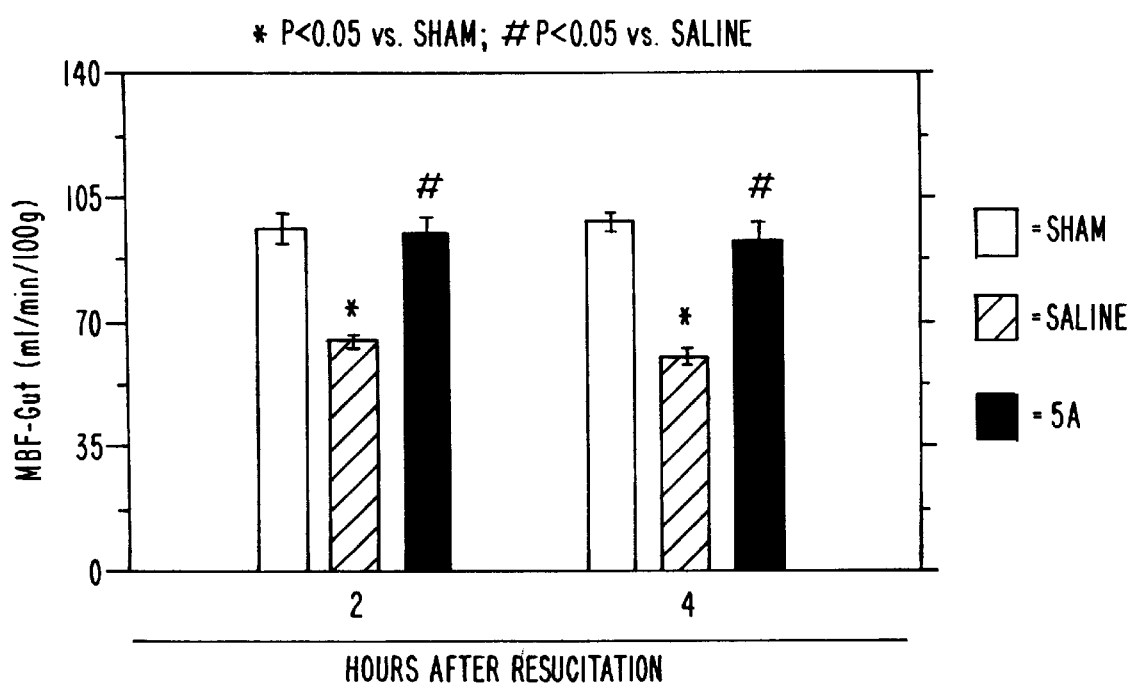

At 2 and 4 hours after the completion of Ringer's lactate resuscitation, the following parameters were monitored: (1) hepatocellular function ($K_m$ and $V_{max}$ associated with indocyanine green clearance in (FIGS. 10A and B), Wang, P. et al, Am. J. Physiol. (1990) 259:R645, Wang, P. et al, J. Surg. Res. (1990) 48:464); (2) mean arterial pressure (MAP) and heart rate (HR) (FIGS. 11A and B); cardiac function (Wang, P. et al, J. Surg. Res. (1991) 50:163), {cardiac output (CO), stroke volume (SV) and total peripheral resistance (TPR) FIGS. 12A, B and C}; and (4) microvascular blood flow (MBF) in liver, kidney, spleen and small intestine (FIGS. 13A, B, C and D, respectively). In FIGS. 10–13, data are presented for three different experimental groups consisting of (1) sham operated (positive control), (2) saline treated (negative control) and (3) 5A.

Hepatocellular function was monitored using indocyanine clearance kinetics, where the $K_m$ and $V_{max}$ correlate with the efficiency of active transport, and rate of clearance, respectively. The maximal clearance rate ($V_{max}$, FIG. 10) at 2 h after initiating resuscitation was significantly higher in the 5A group than the saline group, and was about 85% of sham level. The effect was slightly reduced, but significant at 4 h, and still two-fold that of saline treated animals. The efficiency of active transport ($K_m$) at 2 h for the 5A group was higher (150–160%) than in the sham and saline groups. At 4 h the 5A group had decreased (125%) to values nearer sham and about three-fold higher than the saline treated group. These results suggest an improved hepatic function relative to saline group.

Cardiac function of the 5A group was improved relative to saline treated negative control animals. The mean arterial pressure (FIG. 11A) for 5A and saline treated animals was not significantly different, and were about 60–70% of the sham group. Heart rate (FIG. 11B) for all three groups were about the same indicating that neither challenge nor treatment significantly affected heart rate. Cardiac output (FIG. 12A) in the 5A group was significantly elevated relative to the saline group and was about 80% of sham group. Similarly, stroke volume (FIG. 12B) for the 5A group was elevated relative to saline group and was about 85% of sham group. TPR (FIG. 12C) was lower following resuscitation in 5A group versus saline or sham treatment. The enhanced cardiac output and stroke volume in the 5A treated group, relative to saline treated group, and the lower total peripheral resistance, all indicate improved cardiac function, blood supply and reduced resistance to blood flow.

The microvascular blood flow (MBF) was measured at 2 h and 4 h after onset of resuscitation, as shown in FIGS. 13A–D. All the data show the 5A group to have MBF elevated relative to the saline group. Generally, the MBF recovered to within 80–100% of sham using 5A versus 45–65% for saline. The improved microvascular blood flow for 5A treated animals supports improved tissue perfusion for the respective organs.

The results indicate that administration of 5A during crystalloid resuscitation followed by severe hemorrhage restores or significantly improves cardiac output, hepatocellular function ($V_{max}$ and $K_m$) and surface microvascular blood flow in the liver, kidney, spleen and small intestine at 2 and 4 hours after the completion of the fluid resuscitation. Treatment with 5A decreases total peripheral resistance. Administration of 5A has no significant effects on mean arterial pressure, heart rate or systemic hematocrit as compared with saline treated group. Thus, administration of 5A as an adjunct following trauma-hemorrhage and fluid resuscitation significantly improves cardiovascular and hepatocellular function even in the absence of blood resuscitation.

EXAMPLE 52

Anti Restenotic Activity of 5A 4 day balloon catheter injury—5A administration

Male Sprague-Dawley rats (3–3.5 months old) were subject to balloon catheter injury of the common carotid artery (Clowes et al. *Lab. Invest.* (1983) 49:208–215). Immediately before surgery, rats (n=6) were injected i.p. with 5A at a dose of 100 mg/kg (total volume injected: 1 ml), and rats (n=5) were injected with an equal volume of 4% carboxymethylcellulose vehicle (CMC). Rats were treated for the next four days with daily injections of either 100 mg/kg 5A, or CMC vehicle. Rats were sacrificed at 4 days after injury. They were injected with 25 mg/kg BrdU subcutaneously at 17, 9 and 1 hours before sacrifice to label replicating vascular smooth muscle cells. A catheter was inserted into the aorta, and the carotids were fixed by perfusion with 4% paraformaldehyde at physiologic pressure. After carefully dissecting out the common carotid, the vessels were embedded in paraffin, cross-sectioned and stained with anti-BrdU antibody and hematoxylin, and an index of medical smooth muscle cell replication was obtained by expressing the % labelled SMCs (Lindler et al., *J. Clin. Invest.* (1992) 9:2044–2049).

After fixation, the common carotids were pinned out with the intimal surface facing upwards, and cells present on teh intimal surface were stained with an antibody to histone proteins. With this procedure, only the surface cells are stained; the antibody does not penetrate past the internal elastic lamina. The surface cells were counted and the number of cells per unit area was determined. Administration of 5A caused a significant decrease in number of cells per unit area when compared to CMC treated controls (FIG. 14). There was a very large decrease in cell migration into the intima at 4 days after balloon injury.

10 day balloon catheter injury—5A administration

Surgery was performed, and 5A was administered daily for 10 days as described above fort the 4 day animals (n=5 for both groups). The animals were injected with BrdU before sacrifice to label replicating cells in the media and intima. By 10 days after injury, the normal vessel forms a thickened neointima; smooth muscle migration in to the intima and subsequent proliferation contribute to this thickening. Cross-sections of the vessel were cut and stained with anti-BrdU and hematoxylin. Intimal cross-sectional areas were measured using a computer digitizing system. Administration of 5A caused a significant decrease in intimal cross-sectional area when compared to CMC treated controls (FIG. 15). Intimal cell replication rate was significantly higher in the 5A treated rats than in the controls. Despite the increased rate on intimal cell replication, lesion thickness was dramatically reduced in the 5A treated group, suggesting that smooth muscle cell migration into the intima was inhibited.

All data are presented as mean±SEM, and the data were analyzed by student's test.

What is claimed is:

1. A process for the synthesis of an N-acyl-L-amino acid carboxamide which process comprises the steps of
   (a) acylating the α-amino group of an L-amino acid with a acylating agent selected from the group consisting of
      (i) carboxylic acid anhydrides and
      (ii) compounds comprising two carboxylic acid derivatives
         (A) wherein the first carboxylic acid derivative is an activated acyl, and
         (B) wherein the second carboxylic acid derivative is selected from the group consisting of carboxylic acids and carboxylic esters to yield an N-acyl-L-amino acid comprising a carboxylic acid or carboxylic eater derived from said acylating agent;
   (b) amidating the C-terminal carboxylic acid of said N-acyl L-amino acid with an amine to yield an intermediate N-acyl-L-amino acid carboxamide comprising a carboxylic acid or carboxylic ester derived from said acylating agent;
   (c) converting said carboxylic acid or carboxylic ester to a hydroxamic acid; or
   (d) hydrolyzing said carboxylic ester.

2. A process according to claim 1, wherein said N-acyl-L-amino acid carboxamide is N-((2R)-2-isobutyl-3-carboxypropanoyl)-L-tryptophan-(S)-1-phenylethylamide;
   wherein said L-amino acid is L-tryptophan;

wherein said acylating agent is an alkyl ester of racemic 2-isobutyl-3-(alkoxycarbonyl)propanoic acid;

wherein said N-acyl-L-amino acid is an N-((RS)-2-isobutyl-3-(alkoxycarbonyl)propanoyl)-L-tryptophan;

wherein said amine is (S)-1-phenylethylamine;

wherein said intermediate N-acyl-L-amino acid carboxamide is N-((2R)-2-isobutyl-3-(alkoxycarbonyl)propanoyl)-L-tryptophan-(S)-1-phenylethylamide; and wherein said amidation of said C-terminal carboxylic acid of said intermediate N-acyl-L-tryptophan is followed by the step of (d) hydrolyzing said N-((2R)-2-isobutyl-3-(alkoxycarbonyl)propanoyl)-L-tryptophan-(S)-1-phenylethylamide to yield N-((2R)-2-isobutyl-3-carboxypropanoyl)-L-tryptophan-(S)-1-phenylethylamide.

3. The process according to claim 2 wherein said acylating agent reacted with said L-tryptophan is racemic 2-isobutyl-3-(methoxycarbonyl)propanoic acid; and wherein said hydrolysis further comprises treating with aqueous 6N hydrochloric acid.

4. A process for the synthesis of racemic 2-isobutyl-3-(methoxycarbonyl)propanoic acid which process comprises the steps of (a) reacting maleic anhydride with 2-methylpropene to yield β-methallylsuccinic anhydride;

(b) reducing the carbon-carbon double bond of said β-methallylsuccinic anhydride to yield isobutylsuccinic anhydride; and (c) treating said isobutylsuccinic anhydride with anhydrous methanol to yield racemic 2-isobutyl-3-(methoxycarbonyl)propanoic acid; and (d) recovering said racemic 2-isobutyl-3-(methoxycarbonyl)propanoic acid.

5. A process for resolving and isolating racemic 2-isobutyl-3-(methoxycarbonyl)propanoic acid comprising the steps of (a) reacting racemic 2-isobutyl-3-(methoxycarbonyl)propanoic acid with a resolving agent to form a diastereomeric mixture;

(b) separating from said diastereomeric mixture at least one stereochemically pure diastereomer through a difference in physical properties;

(c) releasing said resolving agent from said stereochemically pure diastereomer; and (d) isolating enantiomerically pure 2-isobutyl-3-(methoxycarbonyl)propanoic acid.

6. A process of claim 5 wherein said enantiomerically pure 2-isobutyl-3-(methoxycarbonyl)propanoic acid is (2R)-2-isobutyl-3-(methoxycarbonyl)propanoic acid wherein said resolving agent is (S)-1-phenylethylamine;

wherein said diastereomeric mixture is a diastereomeric salt mixture;

wherein said separation comprises recrystallization of said diastereomeric salt mixture from ethanol/diethyl ether to yield a single diastereomeric salt; and wherein said release of said enantiomerically pure resolving agent comprises treatment of said single diastereomeric salt with saturated aqueous sodium bicarbonate solution followed by aqueous 6N hydrochloric acid to provide (2R)-2-isobutyl-3-(methoxycarbonyl)propanoic acid.

7. A process for the synthesis of an N-acyl-L-amino acid carboxamide derivatives which process comprises the steps of (a) amidating the C-terminal carboxylic acid of an L-amino acid with an amine to yield an L-amino acid carboxamide;

(b) acylating the α-amino group of said L-amino acid carboxamide with an acylating agent selected from the group consisting of
(i) carboxylic acid anhydrides
(ii) compounds comprising two carboxylic acid derivatives
(A) wherein the first carboxylic acid derivative is an activated acyl, and
(B) wherein the second carboxylic acid derivative is selected from the group consisting of carboxylic acids and carboxylic esters to yield an intermediate N-acyl-L-amino acid carboxamide comprising a carboxylic acid or carboxylic ester derived from said acylating agent;

(c) converting said carboxylic acid or carboxylic ester into a hydroxamic acid; or (d) acid hydrolysis of said ester.

8. The process of claim 7 wherein said N-acyl-L-amino acid carboxamide is N-((RS)-2-isobutyl-3-(hydroxyaminocarbonyl)propanoyl)-L-tryptophan-methylamide;

wherein said L-amino acid is L-tryptophan;

is wherein said amine is methylamine;

wherein said L-amino acid carboxamide is L-tryptophan-methylamide;

wherein said acylating agent is racemic 2-isobutyl-3-(methoxycarbonyl)propanoic acid;

wherein said intermediate N-acyl-L-amino acid carboxamide is N-((RS)-2-isobutyl-3-(methoxycarbonyl)propanoyl)-L-tryptophan-methylamide; and wherein said N-((RS)-2-isobutyl-3-(methoxycarbonyl)propanoyl)-L-tryptophan-methylamide is converted to the hydroxamic acid N-((RS)-2-isobutyl-3-(hydroxyaminocarbonyl)propanoyl)-L-tryptophan-methylamide.

9. The process of claim 7 wherein said N-acyl-L-amino acid carboxamide is N-((RS)-2-isobutyl-3-(hydroxyaminocarbonyl)propanoyl)-L-tryptophan-methylamide;

wherein said amidation of said C-terminal carboxylic acid of said L-amino acid with said amine further comprises the steps of (e) reacting said C-terminal carboxylic acid of L-tryptophan with phosgene to yield L-tryptophan anhydride;

(f) reacting said L-tryptophan anhydride with methylamine to form L-tryptophan-methylamide and treating said L-tryptophan-methylamide with hydrochloric acid to yield the salt of said L-tryptophan-methylamide;

wherein said acylation of the α-amino group of said salt of said L-tryptophan-methylamide further comprises the step of (g) reacting isobutylsuccinic anhydride in tetrahydrofuran with said salt of L-tryptophan-methylamide in the presence of a base to yield an isomeric mixture of carboxylic acids of N-((RS)-2-isobutyl-3-carboxypropanoyl)-L-tryptophan-methylamide and N-((RS)-3-isobutyl-3-carboxypropanoyl)-L-tryptophan-methylamide;

wherein the conversion of said carboxylic acids derived from isobutylsuccinic anhydride to said hydroxamic acid further comprises the steps of (h) esterification of said carboxylic acids derived from isobutylsuccinic anhydride with methanol under mild conditions to yield an isomeric mixture of the esters of N-((RS)-2-isobutyl-3-(methoxycarbonyl) propanoyl)-L-tryptophan-methylamide and N-((RS)-3-isobutyl-3-(methoxycarbonyl)propanoyl)-L-tryptophan-methylamide;

(i) converting said isomeric mixture of esters to an isomeric mixture of their respective hydroxamic acids of N-((RS)-2-isobutyl-3-(hydroxyaminocarbonyl)propanoyl)-L-tryptophan-methylamide and N-((RS)-3-isobutyl-3-(hydroxyaminocarbonyl)propanoyl)-L-tryptophan-methylamide; and (j) crystallizing and recovering the isomer N-((RS)-2-isobutyl-3-(hydroxyaminocarbonyl)propanoyl)-L-tryptophan-methylamide from said mixture of hydroxamic acids.

10. The process of claim 7 wherein said N-acyl-L-amino acid carboxamide is N-((RS)-2-isobutyl-3-(hydroxyaminocarbonyl)propanoyl)-L-tryptophan-methylamide;

wherein said amidation of said C-terminal carboxylic acid of L-amino acid with an amine further comprises the steps of (e) reacting said C-terminal carboxylic acid of L-tryptophan with phosgene to yield L-tryptophan anhydride;

(f) reacting said L-tryptophan anhydride with methylamine is to form L-tryptophan-methylamide and treating said L-tryptophan-methylamide with hydrochloric acid to yield the salt of said L-tryptophan-methylamide;

wherein said acylation of the α-amino group of said salt of said L-tryptophan-methylamide further comprises the step of (g) reacting isobutylsuccinic anhydride in tetrahydrofuran with said salt of said L-tryptophan methylamide in the presence of a base, to yield a isomeric mixture of the carboxylic acids of N-((RS)-2-isobutyl-3-carboxypropanoyl)-L-tryptophan-methylamide and N-((RS)-3-isobutyl-3-carboxypropanoyl)-L-tryptophan-methylamide;

wherein said conversion of said carboxylic acid derived from said isobutylsuccinic anhydride to said hydroxamic acid group further comprises the steps of (h) reacting said carboxylic acids of—N-((RS)-2-isobutyl-3-carboxypropanoyl)-L-tryptophan-methylamide and N-(RS)-3-isobutyl-3-carboxypropanoyl)-L-tryptophan-methylamide— with a coupling agent to yield the succinimide derivative, N-((RS)-2-isobutylsuccinimidyl)-L-tryptophan-methylamide; and (i) converting said N-((RS)-2-isobutylsuccinimidyl)-L-tryptophan-methylamide by hydroxylaminolysis to yield a isomeric mixture of N-((RS)-2-isobutyl-3-(hydroxyaminocarbonyl)propanoyl)-L-tryptophan-methylamide and N-((RS)-3-isobutyl-3-(hydroxyaminocarbonyl)propanoyl)-L-tryptophan-methylamide.

11. The process of claim 10 further comprising the step of (j) crystallizing and recovering said N-((RS)-2isobutyl-3-(hydroxyaminocarbonyl)propanoyl)-L-tryptophan-methylamide from said isomeric mixture.

12. The process according to claim 1 or claim 7, wherein said amino acid is L-tryptophan.

13. A process for the synthesis of an N-acyl-L-tryptophan carboxamide of the formula:

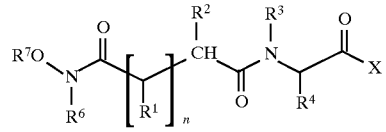

wherein $R^1$ is selected from the group consisting of H and alkyl;

$R^2$ is selected from the group consisting of H, alkyl, and —NHZ, wherein

Z is selected from the group consisting of —$R^{11}$, —$COR^{11}$, and —$COOR^{11}$ where $R^{11}$ is alkyl, or wherein the $R^1$ and $R^2$ taken together are —$(CH_2)_p$—, wherein p is 3–5;

$R^3$ is selected from the group consisting of H and $C_{1-4}$ alkyl;

$R^4$ is selected from the group consisting of —$CH_3$ and fused or conjugated, optionally substituted bicycloaryl methylenes;

n is 0, 1 or 2;

X is selected from the group consisting of —$OR^5$, —$NHR^5$, —$NR^5R^5$, —$NH(CH_2)_q$ and —M, wherein $R^5$ is independently selected from the group consisting of H, optionally substituted alkyl, optionally substituted aryl, and optionally substituted aryl alkyl;

q is 1–8;

M is selected from the group consisting of amino acids, amides of amino acids, cyclic amines, and heterocyclic amines;

$R^6$ is selected from the group consisting of H and lower alkyl; and $R^7$ is selected from the group consisting of H, lower alkyl, and acyl;

which process comprises the steps of (a) acylating the α-amino group of an L-amino acid with a carboxylic acid derivative selected from the group consisting of

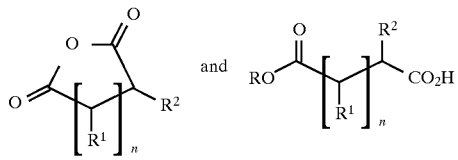

to yield an N-acyl-L-amino acid of the formula:

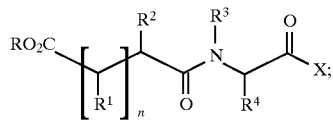

(b) amidating the C-terminal carboxylic acid of said N-acyl-L-amino acid with an amine to yield an N-acyl-L-amino acid carboxamide of the formula:

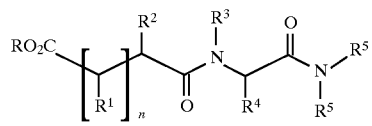

and followed by the step of (c) converting said —COOR group to a hydroxamic acid group; or (d) acid hydrolyzing said —COOR group to a carboxylic acid wherein said —COOR group is an ester.

14. A process for the synthesis of a compound of the formula:

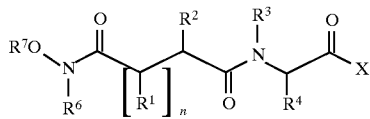

wherein $R^1$ is selected from the group consisting of H and alkyl;

$R^2$ is selected from the group consisting of H, alkyl, and NHZ, wherein
   Z is selected from the group —$R^{11}$, —$COR^{11}$, and —$COOR^{11}$ where $R^{11}$ is alkyl, or wherein the $R^1$ and $R^2$ taken together are —$(CH_2)_p$—, wherein p is 3–5;

$R^3$ is selected from the group consisting of H and $C_{1-4}$ alkyl;

$R^4$ is selected from the group consisting of —$CH_3$ and fused or conjugated, optionally substituted bicycloaryl methylene;

n is 0, 1 or 2;

X is selected from the group consisting of —$OR^5$, —$NHR^5$, —$NR^5R^5$, —$NH(CH_2)_q$ and —M, wherein
   $R^5$ is independently selected from the group consisting of H, optionally substituted alkyl, optionally substituted aryl, and optionally substituted aryl alkyl;
   q is 1–8;
   M is selected from the group consisting of amino acids, amides of amino acids, cyclic amines, and heterocyclic amines;

$R^6$ is selected from the group consisting of H and lower alkyl; and $R^7$ is selected from the group consisting of H, lower alkyl, and acyl;

which process comprises the steps of (a) amidating the C-terminal carboxylic acid of an L-amino acid with an amine to yield an L-amino acid carboxamide of the formula:

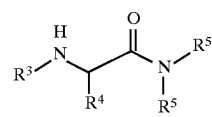

(b) acylating the α-amino group of said L-amino acid carboxamide with a carboxylic acid derivative selected from the group consisting of

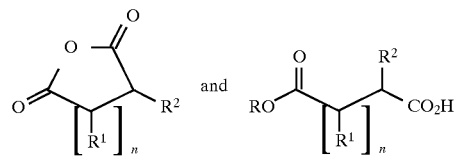

to yield an N-acyl-L-amino acid carboxamide of the formula:

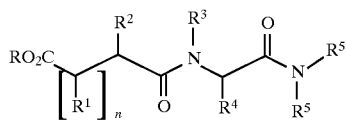

and followed by the step of (c) converting said —COOR group to an hydroxamic acid group; or (d) acid hydrolyzing of said —COOR group to a carboxylic acid wherein said —COOR group is an ester.

* * * * *